United States Patent
Gharabegian (12)

(10) Patent No.: US 10,334,921 B2
(45) Date of Patent: Jul. 2, 2019

(54) SHADING SYSTEM INCLUDING VOICE RECOGNITION OR ARTIFICIAL INTELLIGENT CAPABILITIES

(71) Applicant: Shadecraft, Inc., Pasadena, CA (US)

(72) Inventor: Armen Sevada Gharabegian, Glendale, CA (US)

(*) Notice: Subject to any disclaimer, the term of this patent is extended or adjusted under 35 U.S.C. 154(b) by 0 days.

(21) Appl. No.: 15/838,022

(22) Filed: Dec. 11, 2017

(65) Prior Publication Data
US 2018/0199683 A1 Jul. 19, 2018

Related U.S. Application Data

(63) Continuation of application No. 15/418,380, filed on Jan. 27, 2017, now Pat. No. 9,839,267, which is a (Continued)

(51) Int. Cl.
*A45B 25/16* (2006.01)
*E04H 15/28* (2006.01)
(Continued)

(52) U.S. Cl.
CPC .............. *A45B 25/16* (2013.01); *A45B 23/00* (2013.01); *E04H 15/28* (2013.01); *G06F 3/167* (2013.01);
(Continued)

(58) Field of Classification Search
CPC ....... E04H 15/28; A45B 25/165; A45B 23/00; A45B 2200/1018; A45B 2023/0012
See application file for complete search history.

(56) References Cited

U.S. PATENT DOCUMENTS 2,744,672 A 5/1956 Christ
5,273,062 A * 12/1993 Mozdzanowski ........ A45B 3/00
135/16

(Continued)

FOREIGN PATENT DOCUMENTS

CN 202974544 6/2013
CN 104469162 3/2015
(Continued)

OTHER PUBLICATIONS

International Search Report, PCT Application No. PCT/US2017/068771, dated May 10, 2018, Federal Institute of Industrial Property, Authorized Officer, A. Chekalkina.
(Continued)

*Primary Examiner* — Noah Chandler Hawk

(57) ABSTRACT

An intelligent umbrella system, comprises one or more shading elements; a support assembly, coupled to the one or more shading elements, to provide support for the one or more shading elements; and a base assembly, coupled to the support assembly, to provide contact with a surface. The intelligent umbrella also includes one or more microphones to capture spoken or audio commands; one or more processors; one or more memory modules; and one or more wireless communication transceivers. The intelligent umbrella system includes computer-readable instructions stored in the one or more memory modules that are executed by the one or more processors to convert the captured audio commands into audio files; and perform voice recognition on the converted audio files to generate instructions or commands based, at least in part, on the converted audio files.

15 Claims, 26 Drawing Sheets

Related U.S. Application Data continuation-in-part of application No. 15/394,080, filed on Dec. 29, 2016, now Pat. No. 9,951,541.

(51) Int. Cl.

| | | |
|---|---|---|
| *A45B 23/00* | (2006.01) | |
| *G08C 17/02* | (2006.01) | |
| *G10L 15/22* | (2006.01) | |
| *H04N 7/18* | (2006.01) | |
| *G06F 3/16* | (2006.01) | |
| *G08B 3/10* | (2006.01) | |
| *A45B 25/00* | (2006.01) | |
| *G01N 33/00* | (2006.01) | |
| *G01L 7/12* | (2006.01) | |
| *G08B 15/00* | (2006.01) | |
| *G08B 21/12* | (2006.01) | |

(52) U.S. Cl.
CPC ............... *G08B 3/10* (2013.01); *G08C 17/02* (2013.01); *G10L 15/22* (2013.01); *H04N 7/183* (2013.01); *A45B 2023/0006* (2013.01); *A45B 2023/0012* (2013.01); *A45B 2025/003* (2013.01); *G01L 7/12* (2013.01); *G01N 33/0027* (2013.01); *G06F 3/165* (2013.01); *G08B 15/00* (2013.01); *G08B 21/12* (2013.01); *G08C 2200/00* (2013.01); *G10L 2015/223* (2013.01)

(56) References Cited

U.S. PATENT DOCUMENTS

| | | | |
|---|---|---|---|
| 6,923,193 B2* | 8/2005 | Chen | A45B 23/00 135/20.1 |
| 7,407,178 B2* | 8/2008 | Freedman | A45B 11/00 135/20.3 |
| 8,413,671 B2 | 4/2013 | Li | |
| 8,983,534 B2 | 3/2015 | Patel | |
| 9,345,295 B2* | 5/2016 | Li | A45B 3/02 |
| 9,526,306 B2* | 12/2016 | Fitzgerald | A45B 19/00 |
| 9,629,426 B1 | 4/2017 | Dai | |
| 2002/0161476 A1 | 10/2002 | Panofsky | |
| 2003/0000559 A1 | 1/2003 | Wu | |
| 2005/0016571 A1 | 1/2005 | Wu | |
| 2005/0156027 A1 | 7/2005 | Munari | |
| 2007/0040647 A1 | 2/2007 | Saenz et al. | |
| 2007/0283987 A1* | 12/2007 | Reyes | A45B 3/04 135/16 |
| 2007/0285053 A1 | 12/2007 | Noguchi | |
| 2007/0286463 A1 | 12/2007 | Ritzau et al. | |
| 2008/0076379 A1* | 3/2008 | Li | A45B 3/04 455/344 |
| 2008/0172938 A1 | 7/2008 | Butler | |
| 2010/0204841 A1 | 8/2010 | Chemel et al. | |
| 2010/0245032 A1 | 9/2010 | Li | |
| 2010/0268792 A1 | 10/2010 | Butler et al. | |
| 2011/0066297 A1 | 3/2011 | Saberi | |
| 2011/0173568 A1 | 7/2011 | Royal, Jr. | |
| 2011/0203754 A1 | 8/2011 | Mullet | |
| 2012/0104785 A1 | 5/2012 | Hixson | |
| 2012/0318406 A1 | 12/2012 | Cajiga | |
| 2012/0330461 A1 | 12/2012 | Doom | |
| 2013/0048829 A1* | 2/2013 | Herniak | G01S 3/781 250/203.4 |
| 2013/0073283 A1 | 3/2013 | Yamabe | |
| 2013/0325448 A1 | 12/2013 | Levien | |
| 2014/0041555 A1* | 2/2014 | Ramberg | F16M 13/022 108/50.12 |
| 2014/0078652 A1 | 3/2014 | Kamen | |
| 2014/0116870 A1 | 5/2014 | Kamen | |
| 2014/0279541 A1 | 9/2014 | Castrechini | |
| 2014/0317168 A1 | 10/2014 | Suresh | |
| 2015/0043202 A1 | 2/2015 | Kosedag | |
| 2015/0144653 A1 | 5/2015 | Kline | |
| 2015/0216273 A1* | 8/2015 | Akin | B23P 15/26 135/16 |
| 2015/0255853 A1 | 9/2015 | Kwong et al. | |
| 2015/0366405 A1 | 12/2015 | Manchuliantsau | |
| 2016/0058236 A1 | 3/2016 | Meyers | |
| 2016/0119699 A1* | 4/2016 | Caban | H04R 1/025 381/120 |
| 2016/0306605 A1 | 10/2016 | Smith | |
| 2016/0326765 A1 | 11/2016 | Barbret | |
| 2016/0335929 A1 | 11/2016 | Meisels | |
| 2016/0338457 A1 | 11/2016 | Gharabegian | |
| 2016/0280526 A1 | 12/2016 | O'Laughlin | |
| 2016/0364989 A1 | 12/2016 | Spealsl | |
| 2017/0158108 A1 | 6/2017 | Elbaz | |
| 2017/0228958 A1 | 8/2017 | Shimmerlik | |
| 2018/0053369 A1 | 2/2018 | High | |
| 2018/0136648 A1 | 5/2018 | Su | |
| 2018/0259973 A1 | 9/2018 | Maruo | |

FOREIGN PATENT DOCUMENTS

| | | |
|---|---|---|
| CN | 104835334 | 8/2015 |
| CN | 106163041 | 11/2016 |
| WO | WO2011/115418 | 9/2011 |
| WO | WO2016/174312 | 11/2016 |
| WO | WO 2017/127845 | 7/2017 |

OTHER PUBLICATIONS

Written Opinion and International Search Report for PCT International Application No. PCTUS2018/041080, International Filing Date Jul. 6, 2018, dated Oct. 11, 2018.

Written Opinion and International Search Report for PCT International Application No. PCTUS2018/046364, International Filing Date Aug. 10, 2018, dated Nov. 22, 2018.

Written Opinion and International Search Report for PCT International Application No. PCTUS2018/045435, International Filing Date Aug. 6, 2018, dated Nov. 22, 2018.

Written Opinion and International Search Report for PCT International Application No. PCTUS2018/047010, International Filing Date Aug. 19, 2018, dated Nov. 22, 2018.

* cited by examiner

Fig. 13

| Hardware | | | Function |
|---|---|---|---|
| 1305 Telemetry Board With Slave Processor | GPS/GNSS | 1306 | Provide Location and Orientation Information |
| | Digital Compass | 1307 | |
| 1310 Weather Variables Board With Slave Processor | Air Quality Sensor | 1311 | Sense Weather Variables Surrounding the Shade. Detect High Winds and Close Shade's Arms |
| | UV Radiation Sensor | 1312 | |
| | Digital Barometer | 1313 | |
| | Temperature | 1314 | |
| | Humidity | 1316 | |
| | Wind Speed | 1317 | |
| 1315 Voice Recognition Board With Slave Processor | | | Enable Control Via Voice Commands, Provide Audible Warnings |
| 1320 Rechargable Battery | | | Store Electricity Collected Through Solar Panel/AC Charger Provide Electricity for All Shade Components |
| 1325 Solar Panel | | | Generate Electricity To Charge the Battery |
| 1330 Power Tracking Solar Charger | | | Regulate and Balance the Charging Process Provide Data Regarding Charging State |
| 1335 AC Adapter Input | | | Charge the Battery/Run System in Absence of Sun |
| 1340 Proximity Sensor | | | Identify the Location of A Person Relative to Moving Components |
| 1345 Motion Sensor | | | Detect Presence of Person Around Shade |
| 1350 Code Based Obstacle Detector | | | Detect Presence of Person/Object Within Shade's Path of Travel |
| 1355 Tilt Sensor | | | Detect movement/relocation of Shade and Reorient to Correct Position |
| 1360 Linux Based Computer With Integrated Wifi And 5xIP Cameras | | | Collect Video Feed along with Sensor data Communicate Through Wifi. |
| 1365 Bluetooth | | | Provides Short Distance Communication for App Based Control, Audio Transmission, and Data Retrieval. |
| 1370 LED Lighting | | | Provides Light During Night Operation |
| 1375 Class D Stereo Amplifier With Speakers | | | Provides Audio Playback Through Mobile App or Wifi Stream |
| 1380 Azimuth Servo Motor With Controller | | | Rotates Shade to Predetermined Azimuth Angle |
| 1385 Elevation Servo Motor With Controller | | | Rotates Shade to Predetermined Elevation Angle |
| 1390 Actuator Servo Motor With Controller | | | Extend/Retract Shade Blades |
| 1395 Motion Control PCB | | | |
| 1357 Digital Cameras | | | |
| 1366 Wind Turbine | | | |
| 1377 USB Device | | | |

SHADING SYSTEM INCLUDING VOICE RECOGNITION OR ARTIFICIAL INTELLIGENT CAPABILITIES

RELATED APPLICATIONS

This application claims priority to and is a continuation of U.S. patent application Ser. No. 15/418,380, filed Jan. 27, 2017, entitled "Shading System with Artificial Intelligence Application Programming Interface," which is a continuation-in-part of patent application Ser. No. 15/394,080, filed Dec. 29, 2016, entitled "Modular Umbrella Shading System," the disclosure of which is hereby incorporated by reference.

BACKGROUND

1. Field

The subject matter disclosed herein relates to a modular umbrella shading system utilizing voice recognition and/or artificial intelligence and specifically to an intelligent automated electronic umbrella that includes components to allow for a plurality of configurations and also to utilize artificial intelligence and voice recognition.

2. Information/Background of the Invention

Conventional sun shading devices and systems usually are comprised of a supporting frame and an awning or fabric mounted on the supporting frame to cover a pre-defined area. For example, a conventional sun shading device or system may be an outdoor umbrella or an outdoor awning.

However, current sun shading devices or systems do not appear to be customizable to unique needs of consumers. Customers may have sun shading devices or systems installed in different size areas, in different environments, and require different features and/or options. In addition current sun shading devices and/or systems do not appear to be flexible, modifiable or able to adapt to changing environmental conditions. Further, many of the current sun shading devices appear to require manual operation in order to change inclination angle of the frame to more fully protect an individual from the environment. Further, the current sun shading devices appear to have one (or a single) awning or fabric piece that is mounted to an interconnected unitary frame. An interconnected unitary frame may not be able to be opened or deployed in many situations. Accordingly, alternative embodiments may be desired.

BRIEF DESCRIPTION OF DRAWINGS

Non-limiting and non-exhaustive aspects are described with reference to the following figures, wherein like reference numerals refer to like parts throughout the various figures unless otherwise specified.

FIG. 13 illustrates a block diagram of a modular umbrella system according to embodiments;

DETAILED DESCRIPTION

Figure 1:
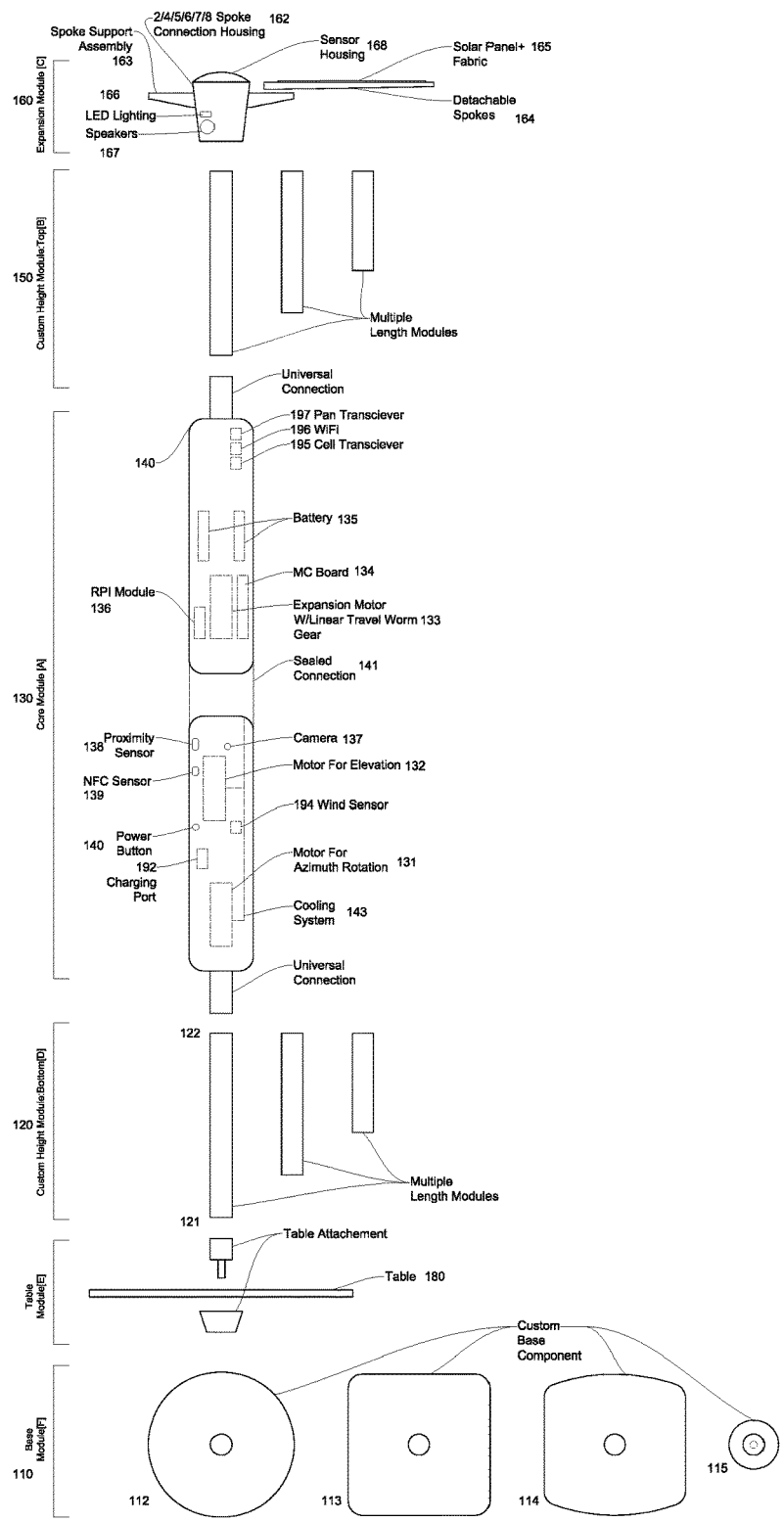
FIG. 1 illustrates a modular umbrella system according to embodiments.

In the following detailed description, numerous specific details are set forth to provide a thorough understanding of claimed subject matter. For purposes of explanation, specific numbers, systems and/or configurations are set forth, for example. However, it should be apparent to one skilled in the relevant art having benefit of this disclosure that claimed subject matter may be practiced without specific details. In other instances, well-known features may be omitted and/or simplified so as not to obscure claimed subject matter. While certain features have been illustrated and/or described herein, many modifications, substitutions, changes and/or equivalents may occur to those skilled in the art. It is, therefore, to be understood that appended claims are intended to cover any and all modifications and/or changes as fall within claimed subject matter.

References throughout this specification to one implementation, an implementation, one embodiment, embodiments, an embodiment and/or the like means that a particular feature, structure, and/or characteristic described in connection with a particular implementation and/or embodiment is included in at least one implementation and/or embodiment of claimed subject matter. Thus, appearances of such phrases, for example, in various places throughout this specification are not necessarily intended to refer to the same implementation or to any one particular implementation described. Furthermore, it is to be understood that particular features, structures, and/or characteristics described are capable of being combined in various ways in one or more implementations and, therefore, are within intended claim scope, for example. In general, of course, these and other issues vary with context. Therefore, particular context of description and/or usage provides helpful guidance regarding inferences to be drawn.

With advances in technology, it has become more typical to employ distributed computing approaches in which portions of a problem, such as signal processing of signal samples, for example, may be allocated among computing devices, including one or more clients and/or one or more servers, via a computing and/or communications network, for example. A network may comprise two or more network devices and/or may couple network devices so that signal communications, such as in the form of signal packets and/or frames (e.g., comprising one or more signal samples), for example, may be exchanged, such as between a server and a client device and/or other types of devices, including between wireless devices coupled via a wireless network, for example.

A network may comprise two or more network and/or computing devices and/or may couple network and/or computing devices so that signal communications, such as in the form of signal packets, for example, may be exchanged, such as between a server and a client device and/or other types of devices, including between wireless devices coupled via a wireless network, for example.

In this context, the term network device refers to any device capable of communicating via and/or as part of a network and may comprise a computing device. While network devices may be capable of sending and/or receiving signals (e.g., signal packets and/or frames), such as via a wired and/or wireless network, they may also be capable of performing arithmetic and/or logic operations, processing and/or storing signals (e.g., signal samples), such as in memory as physical memory states, and/or may, for example, operate as a server in various embodiments.

Computing devices, mobile computing devices, and/or network devices capable of operating as a server, or otherwise, may include, as examples, rack-mounted servers, desktop computers, laptop computers, set top boxes, tablets, netbooks, smart phones, wearable devices, integrated devices combining two or more features of the foregoing devices, the like or any combination thereof. As mentioned, signal packets and/or frames, for example, may be exchanged, such as between a server and a client device and/or other types of network devices, including between wireless devices coupled via a wireless network, for example. It is noted that the terms, server, server device, server computing device, server computing platform and/or similar terms are used interchangeably. Similarly, the terms client, client device, client computing device, client computing platform and/or similar terms are also used interchangeably. While in some instances, for ease of description, these terms may be used in the singular, such as by referring to a "client device" or a "server device," the description is intended to encompass one or more client devices and/or one or more server devices, as appropriate. Along similar lines, references to a "database" are understood to mean, one or more databases, database servers, application data servers, proxy servers, and/or portions thereof, as appropriate.

It should be understood that for ease of description a network device may be embodied and/or described in terms of a computing device and/or mobile computing device. However, it should further be understood that this description should in no way be construed that claimed subject matter is limited to one embodiment, such as a computing device or a network device, and, instead, may be embodied as a variety of devices or combinations thereof, including, for example, one or more illustrative examples.

Operations and/or processing, such as in association with networks, such as computing and/or communications networks, for example, may involve physical manipulations of physical quantities. Typically, although not necessarily, these quantities may take the form of electrical and/or magnetic signals capable of, for example, being stored, transferred, combined, processed, compared and/or otherwise manipulated. It has proven convenient, at times, principally for reasons of common usage, to refer to these signals as bits, data, values, elements, symbols, characters, terms, numbers, numerals and/or the like.

Likewise, in this context, the terms "coupled", "connected," and/or similar terms are used generically. It should be understood that these terms are not intended as synonyms. Rather, "connected" is used generically to indicate that two or more components, for example, are in direct physical, including electrical, contact; while, "coupled" is used generically to mean that two or more components are potentially in direct physical, including electrical, contact; however, "coupled" is also used generically to also mean that two or more components are not necessarily in direct contact, but nonetheless are able to co-operate and/or interact. The term "coupled" is also understood generically to mean indirectly connected, for example, in an appropriate context. In a context of this application, if signals, instructions, and/or commands are transmitted from one component (e.g., a controller or processor) to another component (or assembly), it is understood that messages, signals, instructions, and/or commands may be transmitted directly to a component, or may pass through a number of other components on a way to a destination component. For example, a signal transmitted from a motor controller or processor to a motor (or other driving assembly) may pass through glue logic, an amplifier, an analog-to-digital converter, a digital-to-analog converter, another controller and/or or processor, and/or an interface. Similarly, a signal communicated through a misting system may pass through an air conditioning and/or a heating module, and a signal communicated from any one or a number of sensors to a controller and/or processor may pass through a conditioning module, an analog-to-digital controller, and/or a comparison module, and/or a number of other electrical assemblies and/or components.

The terms, "and", "or", "and/or" and/or similar terms, as used herein, include a variety of meanings that also are expected to depend at least in part upon the particular context in which such terms are used. Typically, "or" if used to associate a list, such as A, B or C, is intended to mean A, B, and C, here used in the inclusive sense, as well as A, B or C, here used in the exclusive sense. In addition, the term "one or more" and/or similar terms is used to describe any feature, structure, and/or characteristic in the singular and/or is also used to describe a plurality and/or some other combination of features, structures and/or characteristics.

Likewise, the term "based on," "based, at least in part on," and/or similar terms (e.g., based at least in part on) are understood as not necessarily intending to convey an exclusive set of factors, but to allow for existence of additional factors not necessarily expressly described. Of course, for all of the foregoing, particular context of description and/or usage provides helpful guidance regarding inferences to be drawn. It should be noted that the following description merely provides one or more illustrative examples and claimed subject matter is not limited to these one or more illustrative examples; however, again, particular context of description and/or usage provides helpful guidance regarding inferences to be drawn.

A network may also include for example, past, present and/or future mass storage, such as network attached storage (NAS), cloud storage, a storage area network (SAN), cloud storage, cloud server farms, and/or other forms of computing and/or device readable media, for example. A network may include a portion of the Internet, one or more local area networks (LANs), one or more wide area networks (WANs), wire-line type connections, one or more personal area networks (PANs), wireless type connections, one or more mesh networks, one or more cellular communication networks, other connections, or any combination thereof. Thus, a network may be worldwide in scope and/or extent.

The Internet and/or a global communications network may refer to a decentralized global network of interoperable networks that comply with the Internet Protocol (IP). It is noted that there are several versions of the Internet Protocol. Here, the term Internet Protocol, IP, and/or similar terms, is intended to refer to any version, now known and/or later developed of the Internet Protocol. The Internet may include local area networks (LANs), wide area networks (WANs), wireless networks, and/or long haul public networks that, for example, may allow signal packets and/or frames to be communicated between LANs. The term World Wide Web (WWW or Web) and/or similar terms may also be used, although it refers to a part of the Internet that complies with the Hypertext Transfer Protocol (HTTP). For example, network devices and/or computing devices may engage in an HTTP session through an exchange of appropriately compatible and/or compliant signal packets and/or frames. Here, the term Hypertext Transfer Protocol, HTTP, and/or similar terms is intended to refer to any version, now known and/or later developed. It is likewise noted that in various places in this document substitution of the term Internet with the term World Wide Web ('Web') may be made without a significant departure in meaning and may, therefore, not be inappropriate in that the statement would remain correct with such a substitution.

Although claimed subject matter is not in particular limited in scope to the Internet and/or to the Web; nonetheless, the Internet and/or the Web may without limitation provide a useful example of an embodiment at least for purposes of illustration. As indicated, the Internet and/or the Web may comprise a worldwide system of interoperable networks, including interoperable devices within those networks. A content delivery server and/or the Internet and/or the Web, therefore, in this context, may comprise an service that organizes stored content, such as, for example, text, images, video, etc., through the use of hypermedia, for example. A HyperText Markup Language ("HTML"), Cascading Style Sheets ("CSS") or Extensible Markup Language ("XML"), for example, may be utilized to specify content and/or to specify a format for hypermedia type content, such as in the form of a file and/or an "electronic document," such as a Web page, for example. HTML and/or XML are merely example languages provided as illustrations and intended to refer to any version, now known and/or developed at another time and claimed subject matter is not intended to be limited to examples provided as illustrations, of course.

Also as used herein, one or more parameters may be descriptive of a collection of signal samples, such as one or more electronic documents, and exist in the form of physical signals and/or physical states, such as memory states. For example, one or more parameters, such as referring to an electronic document comprising an image, may include parameters, such as 1) time of day at which an image was captured, latitude and longitude of an image capture device, such as a camera; 2) time and day of when a sensor reading (e.g., humidity, temperature, air quality, UV radiation) was received; and/or 3) operating conditions of one or more motors or other components or assemblies in a modular umbrella shading system. Claimed subject matter is intended to embrace meaningful, descriptive parameters in any format, so long as the one or more parameters comprise physical signals and/or states, which may include, as parameter examples, name of the collection of signals and/or states.

Some portions of the detailed description which follow are presented in terms of algorithms or symbolic representations of operations on binary digital signals stored within a memory of a specific apparatus or special purpose computing device or platform. In the context of this particular specification, the term specific apparatus or the like includes a general purpose computer once it is programmed to perform particular functions pursuant to instructions from program software. In embodiments, a modular umbrella shading system may comprise a computing device installed within or as part of a modular umbrella system, intelligent umbrella and/or intelligent shading charging system. Algorithmic descriptions or symbolic representations are examples of techniques used by those of ordinary skill in the signal processing or related arts to convey the substance of their work to others skilled in the art. An algorithm is here, and generally, considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared or otherwise manipulated.

It has proven convenient at times, principally for reasons of common usage, to refer to such signals as bits, data, values, elements, symbols, numbers, numerals or the like, and that these are conventional labels. Unless specifically stated otherwise, it is appreciated that throughout this specification discussions utilizing terms such as "processing," "computing," "calculating," "determining" or the like may refer to actions or processes of a specific apparatus, such as a special purpose computer or a similar special purpose electronic computing device (e.g., such as a shading object computing device). In the context of this specification, therefore, a special purpose computer or a similar special purpose electronic computing device (e.g., a modular umbrella computing device) is capable of manipulating or transforming signals (electronic and/or magnetic) in memories (or components thereof), other storage devices, transmission devices sound reproduction devices, and/or display devices.

In an embodiment, a controller and/or a processor typically performs a series of instructions resulting in data manipulation. In an embodiment, a microcontroller or microprocessor may be a compact microcomputer designed to govern the operation of embedded systems in electronic devices, e.g., an intelligent, automated shading object or umbrella, modular umbrella, and/or shading charging systems, and various other electronic and mechanical devices coupled thereto or installed thereon. Microcontrollers may include processors, microprocessors, and other electronic components. Controller may be a commercially available processor such as an Intel Pentium, Motorola PowerPC, SGI MIPS, Sun UltraSPARC, or Hewlett-Packard PA-RISC processor, but may be any type of application-specific and/or specifically designed processor or controller. In an embodiment, a processor and/or controller may be connected to other system elements, including one or more memory devices, by a bus, a mesh network or other mesh components. Usually, a processor or controller, may execute an operating system which may be, for example, a Windows-based operating system (Microsoft), a MAC OS System X operating system (Apple Computer), one of many Linux-based operating system distributions (e.g., an open source operating system) a Solaris operating system (Sun), a portable electronic device operating system (e.g., mobile phone operating systems), microcomputer operating systems, and/or a UNIX operating systems. Embodiments are not limited to any particular implementation and/or operating system.

The specification may refer to a modular umbrella shading system (or an intelligent shading object or an intelligent umbrella) as an apparatus that provides shade and/or coverage to a user from weather elements such as sun, wind, rain, and/or hail. In embodiments, the modular umbrella shading system may be an automated intelligent shading object, automated intelligent umbrella, and/or automated intelligent shading charging system. The modular umbrella shading system and/or automated shading object or umbrella may also be referred to as a parasol, intelligent umbrella, sun shade, outdoor shade furniture, sun screen, sun shelter, awning, sun cover, sun marquee, brolly and other similar names, which may all be utilized interchangeably in this application. Shading objects and/or modular umbrella shading systems which also have electric vehicle charging capabilities may also be referred to as intelligent umbrella charging systems. These terms may be utilized interchangeably throughout the specification. The modular umbrella systems, shading objects, intelligent umbrellas, umbrella charging systems and shading charging systems described herein comprises many novel and non-obvious features, which are described in detail in the following patent applications, U.S. non-provisional application Ser. No. 15/273,669, filed Sep. 22, 2016, entitled "Mobile Computing Device Control of Shading Object, Intelligent Umbrella and Intelligent Shading Charging System," which is a continuation-in-part of U.S. non-provisional application Ser. No. 15/268,199, filed Sep. 16, 2016, entitled "Automatic Operation of Shading Object, Intelligent Umbrella and Intelligent Shading Charging System," which is a continuation-in-part of U.S. non-provisional application Ser. No. 15/242,970, filed Aug. 22, 2016, entitled "Shading Object, Intelligent Umbrella and Intelligent Shading Charging Security System and Method of Operation," which is a continuation-in-part of U.S. non-provisional application Ser. No. 15/225,838, filed Aug. 2, 2016, entitled "Remote Control of Shading Object and/or Intelligent Umbrella," which is a continuation-in-part of U.S. non-provisional patent application Ser. No. 15/219,292, filed Jul. 26, 2016, entitled "Shading Object, Intelligent Umbrella and Intelligent Shading Object Integrated Camera and Method of Operation," which is a continuation-in-part of U.S. non-provisional patent application Ser. No. 15/214,471, filed Jul. 20, 2016, entitled "Computer-Readable Instructions Executable by a Processor to Operate a Shading Object, Intelligent Umbrella and/or Intelligent Shading Charging System," which is a continuation-in-part of U.S. non-provisional patent application Ser. No. 15/212,173, filed Jul. 15, 2016, entitled "Intelligent Charging Shading Systems," which is a continuation-in-part of application of U.S. non-provisional patent application Ser. No. 15/160,856, filed May 20, 2016, entitled "Automated Intelligent Shading Objects and Computer-Readable Instructions for Interfacing With, Communicating With and Controlling a Shading Object," and is also a continuation-in-part of application of U.S. non-provisional patent application Ser. No. 15/160,822, filed May 20, 2016, entitled "Intelligent Shading Objects with Integrated Computing Device," both of which claim the benefit of U.S. provisional Patent Application Ser. No. 62/333,822, entitled "Automated Intelligent Shading Objects and Computer-Readable Instructions for Interfacing With, Communicating With and Controlling a Shading Object," filed May 9, 2016, the disclosures of which are all hereby incorporated by reference.

FIG. 1 illustrates a modular umbrella shading system according to embodiments. In embodiments, a modular umbrella system 100 comprises a base assembly or module 110, a first extension assembly or module 120, a core assembly module housing (or core umbrella assembly) 130, a second extension assembly or module 150, and an expansion sensor assembly or module (or an arm extension assembly or module) 160. In embodiments, a modular umbrella shading system 100 may not comprise a base assembly or module 110 and may comprise a table assembly or module 180 to connect to table tops, such as patio tables and/or other outdoor furniture. In embodiments, a table assembly or module 180 may comprise a table attachment and/or a table receptacle. In embodiments, a base module or assembly 110 may comprise a circular base component 112, a square or rectangular base component 113, a rounded edges base component 114, and/or a beach or sand base component 115. In embodiments, base components 112, 113, 114, and/or 115 may be interchangeable based upon a configuration required by an umbrella system and/or user. In embodiments, each of the different options for the base components 112, 113, 114, 115, and/or 180 may have a universal connector and/or receptacle to allow for easy interchangeability.

In embodiments, a first extension assembly or module 120 may comprise a shaft assembly having a first end 121 and a second end 122. In embodiments, a first end 121 may be detachably connectable and/or connected to a base assembly or module 110. In embodiments, a second end 122 may be detachably connected and/or connectable to a first end of a core umbrella assembly or module 130. In embodiments, a first end 121 and a second end 122 may have a universal umbrella connector. In other words, a connector may be universal within all modules and/or assemblies of a modular umbrella system to provide a benefit of allowing backwards capabilities with new versions of different modules and/or assemblies of a modular umbrella shading system. In embodiments, a first extension assembly or module 120 may have different lengths. In embodiments, different length first extension assemblies may allow a modular umbrella shading system to have different clearance heights between a base assembly or module 110 and/or a core umbrella assembly or module 130. In embodiments, a first extension assembly or module 110 may be a tube and/or a shell with channels, grooves and/or pathways for electrical wires and/or components and/or mechanical components. In embodiments, a first extension assembly 110 may be a shaft assembly having an inner core comprising channels, grooves and/or pathways for electrical wires, connectors and/or components and/or mechanical components.

In embodiments, a universal umbrella connector or connection assembly 124 may refer to a connection pair and/or connection assembly that may be uniform for all modules, components and/or assemblies of a modular umbrella system 100. In embodiments, having a universal umbrella connector or connection assembly 124 may allow interchangeability and/or backward compatibility of the various assemblies and/or modules of the modular umbrella system 100. In embodiments, for example, a diameter of all or most of universal connectors 124 utilized in a modular umbrella system may be the same. In embodiments, a universal connector or connection assembly 124 may be a twist-on connector. In embodiments, a universal connector 124 may be a drop in connector and/or a locking connector, having a male and female connector. In embodiments, a universal connector or connection assembly 124 may be a plug with another connector being a receptacle. In embodiments, universal connector 124 may be an interlocking plug receptacle combination. For example, universal connector 124 may be a plug and receptacle, jack and plug, flanges for connection, threaded plugs and threaded receptacles, snap fit connectors, adhesive or friction connectors. In embodiments, for example, universal connector or connection assembly 124 may be external connectors engaged with threaded internal connections, snap-fit connectors, push fit couplers. In embodiments, by having a universal connector or connection assembly 124 for joints or connections between a base module or assembly 110 and a first extension module or assembly 120, a first extension module or assembly 120 and a core assembly module or assembly 130, a core assembly module or assembly 130 and a second extension module or assembly 150, and/or a second extension module or assembly 150 and an expansion sensor module or assembly 160, an umbrella or shading object manufacturer may not need to provide additional parts for additional connectors for attaching, coupling or connecting different modules or assemblies of a modular umbrella shading system. In addition, modules and/or assemblies may be upgraded easily because one module and/or assembly may be switched out of a modular umbrella system without having to purchase or procure additional modules because of the interoperability and/or interchangeability.

In embodiments, a core umbrella assembly or module 130 may be positioned between a first extension assembly or module 120 and a second extension assembly or module 150. In embodiments, core umbrella assembly or module 130 may be positioned between a base assembly or module 110 and/or an expansion and sensor module or assembly 160. In embodiments, a core umbrella assembly or module 130 may comprise an upper core assembly 140, a core assembly connector or mid-section 141 and/or a lower core assembly 142. In embodiments, a core assembly connector 141 may be a sealer or sealed connection to protect a modular umbrella system from environmental conditions. In embodiments, a core umbrella assembly or module 130 may comprise two or more motors or motor assemblies. Although the specification may refer to a motor, a motor may be a motor assembly with a motor controller, a motor, a stator, a rotor and/or a drive/output shaft. In embodiments, a core umbrella assembly 130 may comprise an azimuth rotation motor 131, an elevation motor 132, and/or a spoke expansion/retraction motor 133. In embodiments, an azimuth rotation motor 131 may cause a core umbrella assembly 130 to rotate clockwise or counterclockwise about a base assembly or module 110 or a table connection assembly 180. In embodiments, an azimuth rotation motor 131 may cause a core umbrella assembly 130 to rotate about an azimuth axis. In embodiments, a core umbrella assembly or module 130 may rotate up to 360 degrees with respect to a base assembly or module 130.

In embodiments, an elevation motor 132 may cause an upper core assembly 140 to rotate with respect to a lower core assembly 142. In embodiments, an elevation motor 130 may rotate an upper core assembly 140 between 0 to 90 degrees with respect to the lower core assembly 142. In embodiments, an elevation motor 130 may rotate an upper module or assembly 140 between 0 to 30 degrees with respect to a lower assembly or module 142. In embodiments, an original position may be where an upper core assembly 140 is positioned in line and above the lower core assembly 142, as is illustrated in FIG. 1.

In embodiments, a spoke expansion motor 133 may be connected to an expansion and sensor assembly module 160 via a second extension assembly or module 150 and cause spoke or arm support assemblies in a spoke expansion sensor assembly module 160 to deploy or retract outward and/or upward from an expansion sensor assembly module 160. In embodiments, an expansion extension assembly module 160 may comprise a rack gear and spoke connector assemblies (or arms). In embodiments, a spoke expansion motor 133 may be coupled and/or connected to a hollow tube via a gearing assembly, and may cause a hollow tube to move up or down (e.g., in a vertical direction). In embodiments, a hollow tube may be connected and/or coupled to a rack gear, which may be connected and/or coupled to spoke connector assemblies. In embodiments, movement of a hollow tube in a vertical direction may cause spoke assemblies and/or arms to be deployed and/or retracted. In embodiments, spoke connector assemblies and/or arms may have a corresponding and/or associated gear at a vertical rack gear.

In embodiments, a core assembly or module 130 may comprise motor control circuitry 134 (e.g., a motion control board 134) that controls operation of an azimuth motor 131, an elevation motor 132 and/or an expansion motor 133, along with other components and/or assemblies. In embodiments, the core assembly module 130 may comprise one or more batteries 135 (e.g., rechargeable batteries) for providing power to electrical and mechanical components in the modular umbrella system 100. For example, one or more batteries 135 may provide power to motion control circuitry 134, an azimuth motor 131, an expansion motor 133, an elevation motor 132, a camera 137, a proximity sensor 138, a near field communication (NFC) sensor 138. In embodiments, one or more batteries 135 may provide power to an integrated computing device 136, although in other embodiments, an integrated computing device 136 may also comprise its own battery (e.g., rechargeable battery).

In embodiments, the core assembly 130 may comprise a separate and/or integrated computing device 136. In embodiments, a separate computing device 136 may comprise a Raspberry Pi computing device, other single-board computers and/or single-board computing device. Because a modular umbrella shading system has a limited amount of space, a single-board computing device is a solution that allows for increased functionality without taking up too much space in an interior of a modular umbrella shading system. In embodiments, a separate computing device 136 may handle video, audio and/or image editing, processing, and/or storage for a modular umbrella shading system 100 (which are more data intensive functions and thus require more processing bandwidth and/or power). In embodiments, an upper core assembly 140 may comprise one or more rechargeable batteries 135, a motion control board (or motion control circuitry) 134, a spoke expansion motor 133 and/or a separate and/or integrated computing device 136.

In embodiments, a core assembly connector/cover 141 may cover and/or secure a connector between an upper core assembly 140 and a lower core assembly 142. In embodiments, a core assembly connector and/or cover 141 may provide protection from water and/or other environmental conditions. In other words, a core assembly connector and/or cover 141 may make a core assembly 130 waterproof and/or water resistant and in other environments, may protect an interior of a core assembly from sunlight, cold or hot temperatures, humidity and/or smoke. In embodiments, a core assembly connector/cover 141 may be comprised of a rubber material, although a plastic and/or fiberglass material may be utilized. In embodiments, a core assembly connector/cover 141 may be comprised of a flexible material, silicone, and/or a membrane In embodiments, a core assembly connector/cover 141 may be circular and/or oval in shape and may have an opening in a middle to allow assemblies and/or components to pass freely through an interior of a core assembly connector or cover 141. In embodiments, a core assembly connector/cover 141 may adhere to an outside surface of an upper core assembly 140 and a lower core assembly 142. In embodiments, a core assembly connector/cover 141 may be connected, coupled, fastened and/or have a grip or to an outside surface of the upper core assembly 140 and the lower core assembly 142. In embodiments, a core assembly connector and/or cover 141 may be connected, coupled, adhered and/or fastened to a surface (e.g., top or bottom surface) of an upper core assembly and/or lower core assembly 142. In embodiments, a core assembly connector/cover 141 may cover a hinging assembly and/or reparation point, springs, and wires that are present between an upper core assembly 140 and/or a lower core assembly 142.

In embodiments, a core assembly or module 130 may comprise one or more cameras 137. In embodiments, one or more cameras 137 may be capture images, videos and/or sound of an area and/or environment surrounding a modular umbrella system 100. In embodiments, a lower core assembly 142 may comprise one or more cameras 137. In embodiments, a camera 137 may only capture sound if a user selects a sound capture mode on a modular umbrella system 100 (e.g., via a button and/or switch) or via a software application controlling operation of a modular umbrella system (e.g., a microphone or recording icon is selected in a modular umbrella system software application).

In embodiments, a core assembly 130 may comprise a power button to manually turn on or off power to components of a modular umbrella system. In embodiments, a core assembly or module 130 may comprise one or more proximity sensors 138. In embodiments, one or more proximity sensors 138 may detect whether or not an individual and/or subject may be within a known distance from a modular umbrella system 100. In embodiments, in response to a detection of proximity of an individual and/or subject, a proximity sensor 138 may communicate a signal, instruction, message and/or command to motion control circuitry (e.g., a motion control PCB 134) and/or a computing device 136 to activate and/or deactivate assemblies and components of a modular umbrella system 100. In embodiments, a lower core assembly 142 may comprise a proximity sensor 138 and a power button. For example, a proximity sensor 138 may detect whether an object is within proximity of a modular umbrella system and may communicate a message to a motion control PCB 134 to instruct an azimuth motor 131 to stop rotating a base assembly or module.

In embodiments, a core assembly or module 130 may comprise a near-field communication (NFC) sensor 139. In embodiments, a NFC sensor 139 may be utilized to identify authorized users of a modular umbrella shading system 100. In embodiments, for example, a user may have a mobile computing device with a NFC sensor which may communicate, pair and/or authenticate in combination with a modular umbrella system NFC sensor 139 to provide user identification information. In embodiments, a NFC sensor 139 may communicate and/or transmit a signal, message, command and/or instruction based on a user's identification information to computer-readable instructions resident within a computing device and/or other memory of a modular umbrella system to verify a user is authenticated and/or authorized to utilize a modular umbrella system 100.

In embodiments, a core assembly or module 130 may comprise a cooling system and/or heat dissipation system 143. In embodiments, a cooling system 143 may be one or more channels in an interior of a core assembly or module 130 that direct air flow from outside a modular umbrella system across components, motors, circuits and/or assembles inside a core assembly 130. For example, one or more channels and/or fins may be coupled and/or attached to components, motors and/or circuits, and air may flow through channels to fins and/or components, motors and/or circuits. In embodiments, a cooling system 143 may lower operating temperatures of components, motors, circuits and/or assemblies of a modular umbrella system 100. In embodiments, a cooling system 143 may also comprise one or more plates and/or fins attached to circuits, components and/or assemblies and also attached to channels to lower internal operating temperatures. In embodiments, a cooling system 143 may also move hot air from electrical and/or mechanical assemblies to outside a core assembly. In embodiments, a cooling system 143 may be fins attached to or vents in a body of a core assembly 130. In embodiments, fins and/or vents of a cooling system 143 may dissipate heat from electrical and mechanical components and/or assemblies of the core module or assembly 130.

In embodiments, a separate, detachable and/or connectable skin may be attached, coupled, adhered and/or connected to a core module assembly 130. In embodiments, a detachable and/or connectable skin may provide additional protection for a core assembly module against water, smoke, wind and/or other environmental conditions and/or factors. In embodiments, a skin may adhere to an outer surface of a core assembly .130. In embodiments, a skin may have a connector on an inside surface of the skin and core assembly 130 may have a mating receptacle on an outside surface. In embodiments, a skin may magnetically couple to a core assembly 130. In embodiments, a skin may be detachable and removable from a core assembly so that a skin may be changed for different environmental conditions and/or factors. In embodiments, a skin may connect to an entire core assembly. In embodiments, a skin may connect to portions of an upper core assembly 140 and/or a lower core assembly 142. In embodiments, a skin may not connect to a middle portion of a core assembly 130 (or a core assembly cover connector 141). In embodiments, a skin may be made of a flexible material to allow for bending of a modular umbrella system 100. In embodiments, a base assembly 110, a first extension assembly 120, a core module assembly 130, a second extension assembly 140 and/or an arm extension and sensor assembly 160 may also comprise one or more skin assemblies. In embodiments, a skin assembly may provide a cover for a majority of all of a surface area one or more of the base assembly, first extension assembly 120, core module assembly 130, second extension assembly 150 and/or arm extension sensor assembly 160. In embodiments, a core assembly module 130 may further comprise channels on an outside surface. In embodiments, a skin assembly may comprise two pieces. In embodiments, a skin assembly may comprise edges and/or ledges. In embodiments, edges and/or ledges of a skin assembly may be slid into channels of a core assembly module 130. In embodiments, a base assembly 110, a first extension assembly 120, a second extension assembly 140 and/or an arm expansion sensor assembly 160 may also comprise an outer skin assembly. In embodiments, skin assemblies for these assemblies may be uniform to present a common industrial design. In embodiments, skin assemblies may be different if such as a configuration is desired by a user. In embodiments, skin assemblies may be comprise of a plastic, a hard plastic, fiberglass, aluminum, other light metals (including aluminum), and/or composite materials including metals, plastic, wood. In embodiments, a core assembly module 130, a first extension assembly 120, a second extension assembly 150, an arm expansion sensor assembly 160, and/or a base assembly 110 may be comprised of aluminum, light metals, plastic, hard plastics, foam materials, and/or composite materials including metals, plastic, wood. In embodiments, a skin assembly may be provide protection from environmental conditions (such as sun, rain, and/or wind).

In embodiments, a second extension assembly 150 connects and/or couples a core assembly module 130 to an expansion assembly sensor module (and/or arm extension assembly module) 160. In embodiments, an expansion sensor assembly module 160 may have universal connectors and/or receptacles on both ends to connect or couple to universal receptacles and/or connectors, on the core assembly 130 and/or expansion sensor assembly module 160. FIG. 1 illustrates that a second extension assembly or module 150 may have three lengths. In embodiments, a second extension assembly 150 may have one of a plurality of lengths depending on how much clearance a user and/or owner may like to have between a core assembly module 130 and spokes of an expansion sensor assembly or module 160. In embodiments, a second extension assembly or module 150 may comprise a hollow tube and/or channels for wires and/or other components that pass through the second extension assembly or module 150. In embodiments, a hollow tube 249 may be coupled, connected and/or fixed to a nut that is connected to, for example, a threaded rod (which is part of an expansion motor assembly). In embodiments, a hollow tube 249 may be moved up and down based on movement of the threaded rod. In embodiments, a hollow tube in a second extension assembly may be replaced by a shaft and/or rod assembly.

In embodiments, an expansion and sensor module 160 may be connected and/or coupled to a second extension assembly or module 150. In embodiments, an expansion and sensor assembly or module 160 may be connected and/or coupled to a second extension assembly or module 150 via a universal connector. In embodiments, an expansion and sensor assembly or module 160 may comprise an arm or spoke expansion sensor assembly 162 and a sensor assembly housing 168. In embodiments, an expansion and sensor assembly or module 160 may be connected to a hollow tube 249 and thus coupled to a threaded rod. In embodiments, when a hollow tube moves up and down, an arm or spoke expansion assembly 162 opens and/or retracts, which causes spokes/blades 164 of an arm extension assembly 163. In embodiments, arms, spokes and/or blades 164 may detachably connected to the arm or spoke support assemblies 163.

In embodiments, an expansion and sensor assembly module 160 may have a plurality of arms, spokes or blades 164 (which may be detachable or removable). Because the umbrella system is modular and/or adjustable to meet needs of user and/or environment, an arm or spoke expansion assembly 162 may not have a set number of arm, blade or spoke support assemblies 163. In embodiments, a user and/or owner may determine and/or configure a modular umbrella system 100 with a number or arms, spokes, or blades extensions 163 (and thus detachable spokes, arms and/or blades 164) necessary for a certain function and attach, couple and/or connect an expansion sensor assembly or module 160 with a spoke expansion assembly 162 with a desired number of blades, arms or spoke connections to a second extension module or assembly 150 and/or a core module assembly or housing 130. Prior umbrellas or shading systems utilize a set or established number of ribs and were not adjustable or configurable. In contrast, a modular umbrella system 100 described herein has an ability to have a detachable and adjustable expansion sensor module 162 comprising an adjustable number of arm/spoke/blade support assemblies or connections 163 (and therefore a flexible and adjustable number of arms/spokes/blades 164), which provides a user with multiple options in providing shade and/or protection. In embodiments, expansion and sensor expansion module 160 may be detachable or removable from a second extension module 150 and/or a core assembly module 130 and also one or more spokes, arms and/or assemblies 164 may be detachable or removable from arm or spoke support assemblies 163. Therefore, depending on the application or use, a user, operator and/or owner may detachably remove an expansion and sensor module or assembly 160 having a first number of arm/blade/spoke support assemblies 163 and replace it with a different expansion sensor module or assembly 160 having a different number of arm/blade/spoke support assemblies 163.

In embodiments, arms, blades and/or spokes 164 may be detachably connected and/or removable from one or more arm support assemblies 163. In embodiments, arms, blades, and/or spokes 164 may be snapped, adhered, coupled and/or connected to associated arm support assemblies 163. In embodiments, arms, blades and/or spokes 164 may be detached, attached and/or removed before deployment of the arm extension assemblies 163.

In embodiments, a shading fabric 165 may be connected, attached and/or adhered to one or more arm extension assemblies 163 and provide shade for an area surrounding, below and/or adjacent to a modular umbrella system 100. In embodiments, a shading fabric (or multiple shading fabrics) may be connected, attached, and/or adhered to one or more spokes, arms and/or blades 164. In embodiments, a shading fabric or covering 165 may have integrated therein, one or more solar panels and/or cells (not shown). In embodiments, solar panels and/or cells may generate electricity and convert the energy from a solar power source to electricity. In embodiments, solar panels may be coupled to a shading power charging system (not shown). In embodiments, one or more solar panels and/or cells may be positioned on top of a shading fabric 165. In embodiments, one or more solar panels and/or cells may be connected, adhered, positioned, attached on and/or placed on a shading fabric 165.

In embodiments, an expansion sensor assembly or module 160 may comprise one or more audio speakers 167. In embodiments, an expansion sensor assembly or module 160 may further comprise an audio/video transceiver. In embodiments, a core assembly 130 may comprise and/or house an audio/video transceiver (e.g., a Bluetooth or other PAN transceiver, such as Bluetooth transceiver 197). In embodiments, an expansion sensor assembly or module 160 may comprise an audio/video transceiver (e.g., a Bluetooth and/or PAN transceiver) In embodiments, an audio/video transceiver in an expansion sensor assembly or module 160 may receive audio signals from an audio/video transceiver 197 in a core assembly 130, convert to an electrical audio signal and reproduce the sound on one or more audio speakers 167, which projects sound in an outward and/or downward fashion from a modular umbrella system 100. In embodiments, one or more audio speakers 167 may be positioned and/or integrated around a circumference of an expansion sensor assembly or module 160.

In embodiments, an expansion sensor assembly or module 160 may comprise one or more LED lighting assemblies 166. In embodiments, one or more LED lighting assemblies 166 may comprise bulbs and/or LED lights and/or a light driver and/or ballast. In embodiments, an expansion sensor assembly or module 160 may comprise one or more LED lighting assemblies positioned around an outer surface of the expansion sensor assembly or module 160. In embodiments, one or more LED lighting assemblies 166 may drive one or more lights. In embodiments, a light driver may receive a signal from a controller or a processor in a modular umbrella system 100 to activate/deactivate LED lights. The LED lights may project light into an area surrounding a modular umbrella system 100. In embodiments, one or more lighting assemblies 166 may be recessed into an expansion or sensor module or assembly 160.

In embodiments, an arm expansion sensor housing or module 160 may also comprise a sensor housing 168. In embodiments, a sensor housing 168 may comprise one or more environmental sensors, one or more telemetry sensors, and/or a sensor housing cover. In embodiments, one or more environmental sensors may comprise one or more air quality sensors, one or more UV radiation sensors, one or more digital barometer sensors, one or more temperature sensors, one or more humidity sensors, and/or one or more wind speed sensors. In embodiments, one or more telemetry sensors may comprise a GPS/GNSS sensor and/or one or more digital compass sensors. In embodiments, a sensor housing 168 may also comprise one or more accelerometers and/or one or more gyroscopes. In embodiments, a sensor housing 168 may comprise sensor printed circuit boards and/or a sensor cover (which may or may not be transparent). In embodiments, a sensor printed circuit board may communicate with one or more environmental sensors and/or one or more telemetry sensors (e.g., receive measurements and/or raw data), process the measurements and/or raw data and communicate sensor measurements and/or data to a motion control printed circuit board (e.g., controller) and/or a computing device (e.g., controller and/or processor). In embodiments, a sensor housing 168 may be detachably connected to an arm connection housing/spoke connection housing to allow for different combinations of sensors to be utilized for different umbrellas. In embodiments, a sensor cover of a sensor housing 168 may be clear and/or transparent to allow for sensors to be protected from an environment around a modular umbrella system. In embodiments, a sensor cover may be moved and/or opened to allow for sensors (e.g., air quality sensors to obtain more accurate measurements and/or readings). In embodiments, a sensor printed circuit board may comprise environmental sensors, telemetry sensors, accelerometers, gyroscopes, processors, memory, and/or controllers in order to allow a sensor printed circuit board to receive measurements and/or readings from sensors, process received sensor measurements and/or readings, analyze sensor measurements and/or readings and/or communicate sensor measurements and/or readings to processors and/or controllers in a core assembly or module 130 of a modular umbrella system 100.

Figure 2:
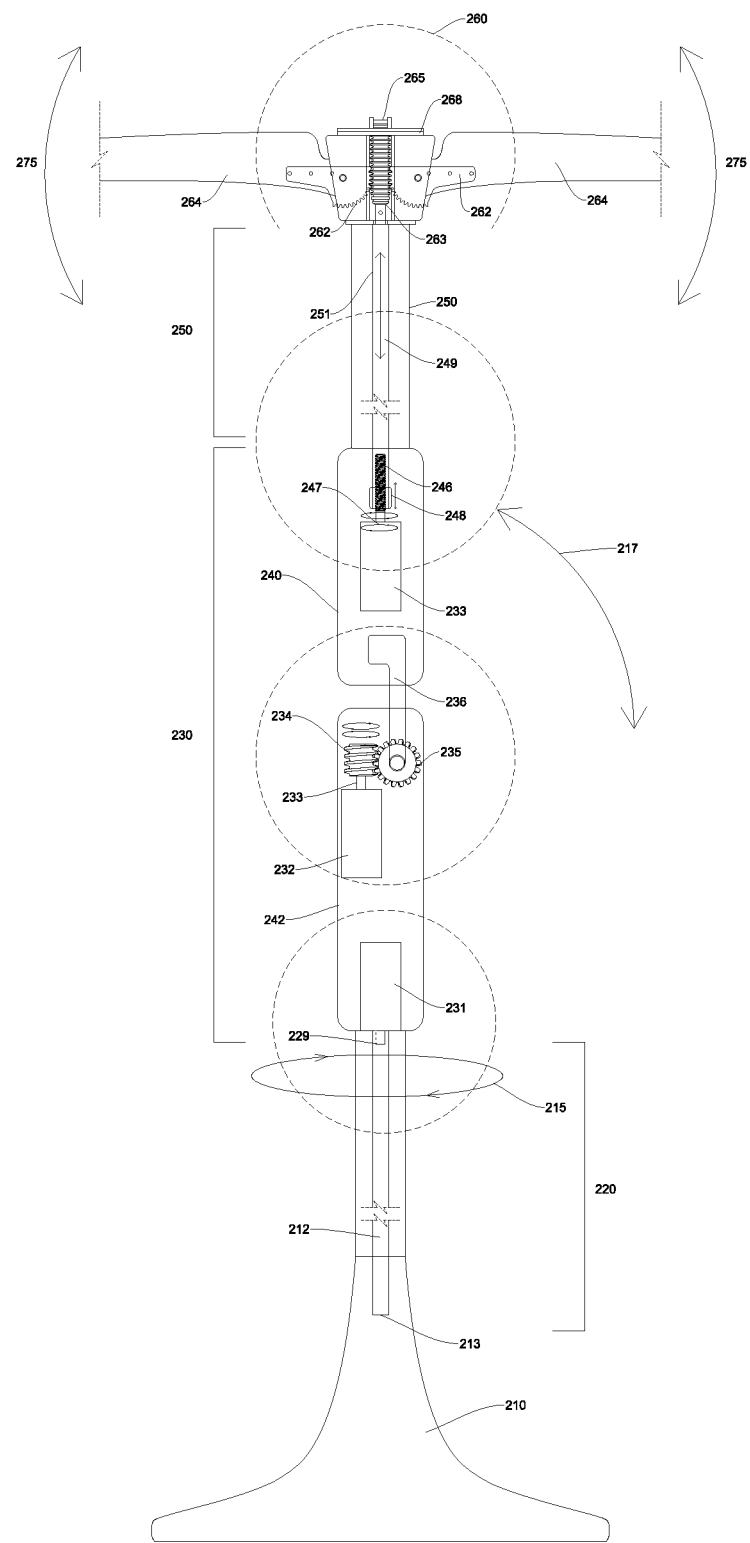
FIG. 2 illustrates a cut-away drawing of mechanical assemblies in a modular umbrella system according to embodiments.

FIG. 2 illustrates a cut-away drawing of mechanical assemblies in a modular umbrella system according to embodiments. In embodiments, a modular umbrella shading assembly 200 may comprise a base assembly 210, a first extension assembly 220, a core assembly or module 230, a base receptacle 213, a force transfer shaft 212, an azimuth motor 231, and/or an azimuth motor shaft 229. In embodiments, a first extension assembly 220 and a core assembly module 230 may rotate in a clockwise or counterclockwise manner direction (as illustrated by reference number 215) with respect to a base assembly 210. In embodiments, an azimuth motor 231 comprises an azimuth motor shaft 229 that may rotate in response to activation and/or utilization of an azimuth motor 231. In embodiments, an azimuth motor shaft 229 may be mechanically coupled (e.g., a gearing system, a friction-based system, etc.) to a force transfer shaft 212. In embodiments, an azimuth motor shaft 229 may rotate in a clockwise and/or counterclockwise direction and in response, a force transfer shaft 212 may rotate in a same and/or opposite direction. In embodiments, a force transfer shaft 212 may pass through a first extension assembly 220 and may be mechanically coupled to a base receptacle 213 in a base assembly 210. In response to, or due to, rotation of force transfer shaft 212 in a base receptacle 213, a first extension assembly 220 and/or a core assembly 230 may rotate with respect to the base assembly 210.

In embodiments, a modular umbrella system 200 may comprise a core assembly 230 which may comprise a lower core assembly 242 and an upper core assembly 240. In embodiments, a lower core assembly 242 may comprise an elevation motor 232, an elevation motor shaft 233, a worm gear 234, and/or a speed reducing gear 235. In embodiments, a speed reducing gear 235 may be connected with a connector to a connection plate 236. In embodiments, a lower core assembly 242 may be mechanically coupled to an upper core assembly 240 via a connection plate 236. In embodiments, a connection plate 236 may be connected to an upper core assembly 240 via a connector and/or fastener. In embodiments, an elevation motor 232 may cause rotation (e.g., clockwise or counterclockwise) of an elevation motor shaft 233, which may be mechanically coupled to a worm gear 234. In embodiments, rotation of an elevation motor shaft 233 may cause rotation (e.g., clockwise or counterclockwise) of a worm gear 234. In embodiments, a worm gear 234 may be mechanically coupled to a speed reducing gear 235. In embodiments, rotation of a worm gear 234 may cause rotation of a speed reducing gear 235 via engagement of channels of a worm gear 234 with teeth of a speed reducing gear 235. In embodiments, a sped reducing gear 235 may be mechanically coupled to a connection plate 236 to an upper core assembly 240 via a fastener or connector. In embodiments, rotation of a speed reducing gear 235 may cause a connection plate 236 (and/or an upper core assembly 240) to rotate with respect to a lower core assembly 242 in a clockwise or counterclockwise direction as is illustrated by reference number 217. In embodiments, an upper core assembly 240 may rotate with respect to the lower core assembly 242 approximately 90 degrees via movement of the connection plate. In embodiments, an upper core assembly 240 may rotate approximately 0 to 30 degrees with respect to the lower core assembly 242 via movement of the connection plate.

In embodiments, an upper core assembly 240 may comprise an extension expansion motor 233 and an extension expansion motor shaft 247. In embodiments, an expansion motor 233 may be activated and may rotate an extension expansion motor shaft 247. In embodiments, an expansion motor shaft 247 may be mechanically coupled to a threaded rod 246 which may be mechanically couple to a travel nut 248 (e.g., a nut may be screwed onto the threaded rod 246). In embodiments, an expansion motor shaft 247 may rotate a threaded rod 246 which may cause a travel nut 248 to move in a vertical direction (e.g., up or down). In embodiments, a travel nut 248 may be mechanically coupled to a connection rod 249. In embodiments, a travel nut 248 may move in vertical direction (e.g., up or down) which may cause a connection rod 249 to move in a vertical direction (e.g., up or down) as is illustrated by reference number 251. In embodiments, a connection rod 249 may be partially positioned and/or located within an upper core assembly 240 and may be partially positioned within a second extension assembly 250. In embodiments, a connection rod 249 and/or a second extension assembly 250 may have varying lengths based on a desired height of a modular umbrella system 200. In embodiments, a connection rod 249 may be mechanically coupled to an expansion assembly shaft 263.

In embodiments, an arm expansion sensor housing or module 260 may comprise an expansion assembly shaft 263, a rack gear 265, one or more spoke/arm expansion assemblies 262, and a sensor module 268. In embodiments, an expansion assembly shaft or hollow tube 263 may be mechanically coupled to a rack gear 265. In embodiments, movement of an expansion shaft or hollow tube 263 up or down in a vertical direction may move a rack gear 265 in a vertical direction (e.g., up or down). In embodiments, one or more spoke expansion assemblies 262 may be mechanically coupled to a rack gear 265. In embodiments, gears on one or more spoke/arm expansion assemblies 262 may engage channels in a rack gear 265. In embodiments, a rack gear 265 may move in a vertical direction (e.g., up or down) which may cause movement of one or more spoke/arm expansion assemblies 262 from an open position (as is illustrated in FIG. 2) to a closed position (or vice versa from a closed position to an open position). In embodiments, movement of one or more spoke/arm expansion assemblies 262 is illustrated by reference number 275 in FIG. 2. In embodiments, spokes/arms 264 may be mechanically coupled to spoke expansion assemblies 262. In embodiments, one or more spokes/arms 264 may be detachable from one or more spoke/arm expansion assemblies 262.

Prior art shading systems utilizing at the most one motor to move a shade into a desired position. Shading systems do not utilize more than one motor and this limits movement of a shade system to track the sun and provide protection to users of a shading system. Accordingly, utilizing of two or more motors in a shading system allow movement of a shading element (or multiple shading elements) to track the sun, to protect a user from other weather elements and/or to capture a large amount of solar energy. These are improvements other shading systems which cannot move and/or rotate about more than one axis. Although, FIGS. 1 and 2 describe a shading system with three motors, additional motors may be utilized to, for example, rotate a shading system (utilizing a motor in a base system next to a surface), additional motors to deploy additional accessories within a shading system core assembly module (e.g., lighting assemblies, wind turbines, camera mounts), or additional motors to deploy accessories within an expansion and sensor assembly module (e.g., deploy sensors, deploy solar panels, move speakers to different positions or orientations and/or move lighting assemblies to different positions and/or orientations).

Figure 3:
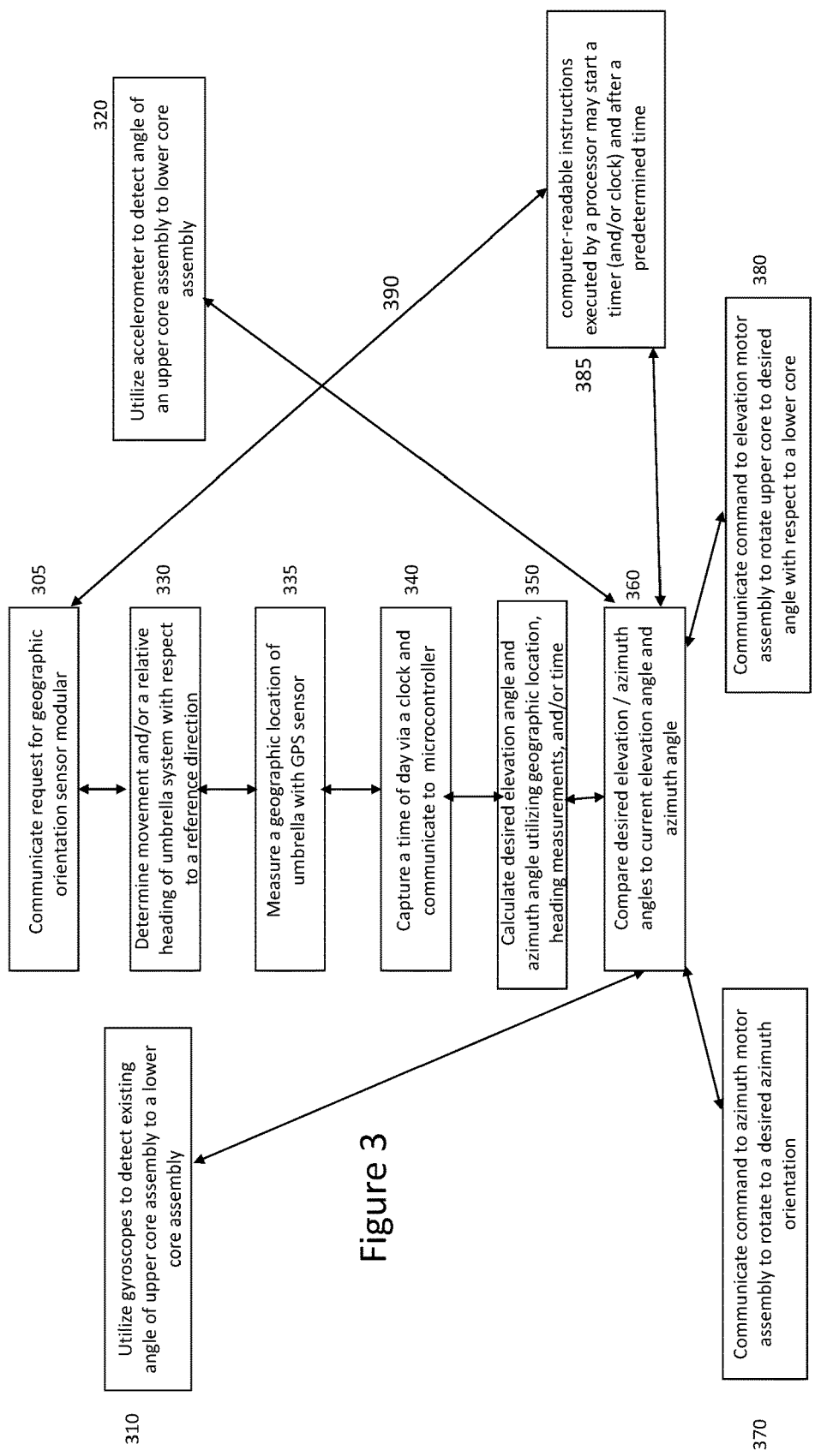
FIG. 3 illustrates a method of a modular umbrella system utilizing directional measuring devices according to embodiments.
Figure 4:
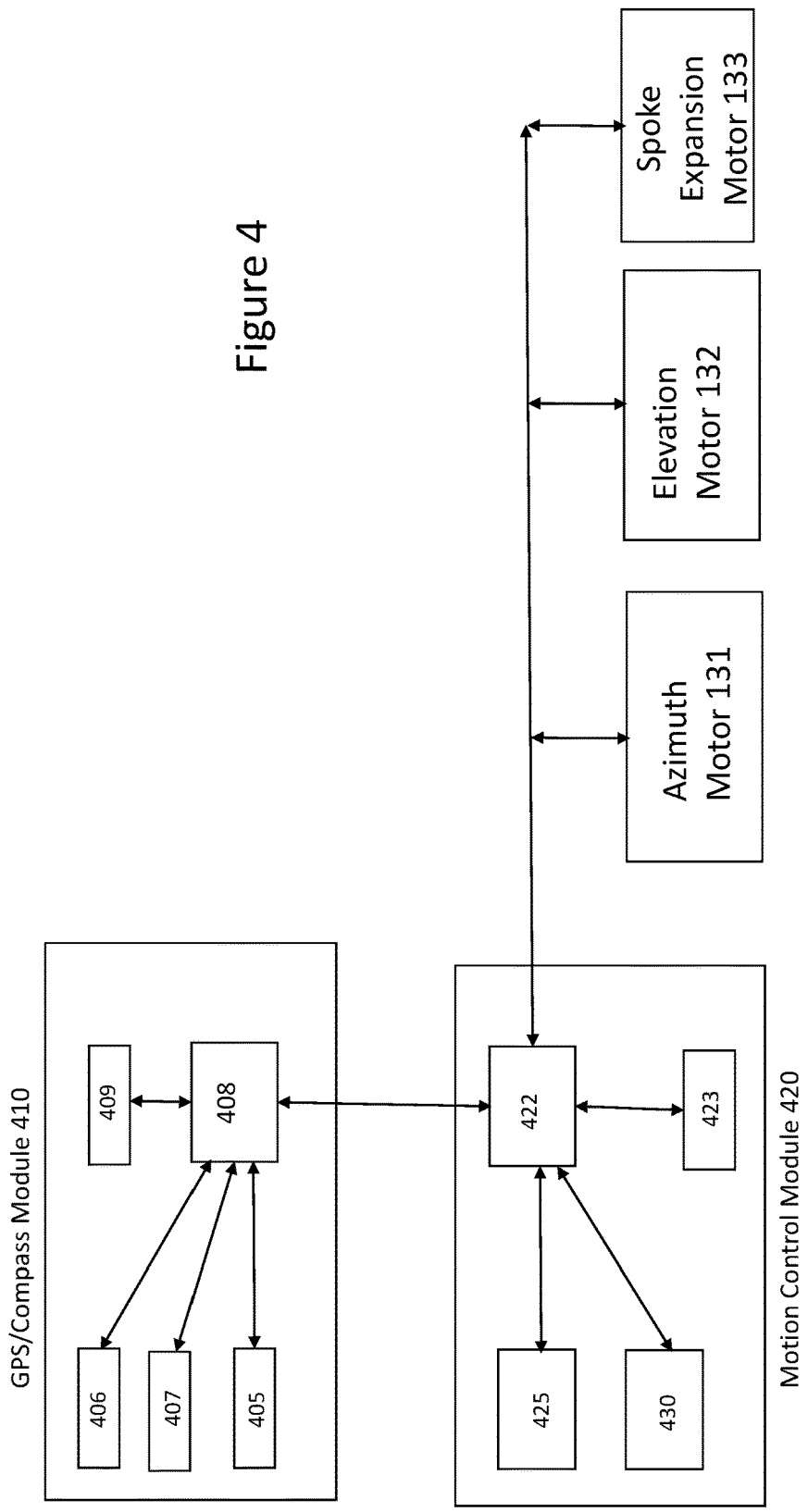
FIG. 4 illustrates a block diagram of a modular umbrella system comprising directional measuring devices according to embodiments.

FIG. 3 illustrates a method of a modular umbrella system utilizing directional measuring devices according to embodiments. FIG. 4 illustrates a block diagram of a modular umbrella system comprising directional measuring devices according to embodiments. In embodiments, a core housing 130 may also comprise a gyroscope 425 and an accelerometer 430. In embodiments, an upper core housing 140 may comprise a gyroscope and/or an accelerometer. In embodiments, as illustrated in FIG. 4, a motion control module 420 (e.g., a motion control PCB) in a modular core housing 130 may comprise one or more processors/controllers 422, one or more memory modules 423, one or more accelerometers 425 and/or one or more gyroscopes 430. In embodiments, directional measuring devices may refer to accelerometers, gyroscopes, compasses, magnetometers and/or GPS devices. In embodiments, a sensor module 410 may comprise a compass, a digital compass and/or a magnetometer 406, one or more GPS transceivers 405, one or more clocks 407, one or more microcontroller/processor 408, and/or one or more memory module 409.

In embodiments, a motion control module 420 may request an initial desired orientation for different assemblies and/or components of a modular umbrella shading system and communicate 305 such directional request to a sensor module 410. In embodiments, one or more gyroscopes 430 may be utilized to determine, calculate and/or detect 310 an angle of an upper core assembly with respect to a lower core assembly (e.g., determine a current elevation of a modular umbrella system). In embodiments, one or more accelerometers may also be utilized along with one or more gyroscopes to determine, calculate and/or detect 320 an angle of an upper core assembly.

In embodiments, a motion control module 420 may communicate the directional request to a sensor extension module 410. In embodiments, a directional measuring device (e.g., compass and/or magnetometer 406) may determine 330 movement and/or a relative position of a modular umbrella shading system with respect from a reference direction. In embodiments, for example, a directional measuring device (e.g., compass, digital compass and/or magnetometer 406) may determine relative movement and/or a relative position with respect to true north. In embodiments, for example, a compass and/or a digital compass may determine movement and/or a relative position with respect to true north. In embodiments, such as illustrated in FIG. 4, these measurements may be referred to as heading measurements. In embodiments, a directional measuring device may communicate and/or transfer heading measurements to a microcontroller 408, where these heading measurements may be stored in a memory 409.

In embodiments, in response to a directional orientation request, a GPS transceiver 405 may measure a geographic location of a modular umbrella system and may communicate 335 such geographic location measurement to a microcontroller 408, which may transfer these heading measurements into a memory 409. In embodiments, a GPS transceiver 405 may determine latitude and/or longitude coordinates and communicate such latitude and/or longitude coordinates to a microcontroller 408. In embodiments, a clock 407 may capture a time of day and communicate and/or transfer 340 such time measurement to a microcontroller 408, which may store the time measurement in a memory 409.

In embodiments, instructions stored in a memory of an extension assembly and/or sensor module 410 and executable by a microcontroller 408 in the extension assembly and/or sensor module 410 may include algorithms and/or processes for determining and/or calculating a desired azimuth and/or orientation of a modular umbrella system depending on a time of day. In alternative embodiments, a microcontroller 408 in an extension assembly and/or sensor module 410 may communicate heading measurements, geographic location measurements and or time measurement to a processor 422 in a motion control module 420. In an alternative embodiment, a portable computing device executing computer-readable instructions on a processor (e.g., a SMARTSHADE software app) and located in a vicinity of a modular umbrella shading system may retrieve coordinates utilizing a mobile computing device's GPS transceiver and may retrieve a time from a mobile computing device's processor clock and provide these geographic location measurements and/or time to a motion control module 420 (e.g., a microcontroller in a motion control module) and/or a sensor module 410 (e.g., a microcontroller in a sensor module).

In embodiments, computer-readable instructions stored in a memory (e.g., memory 409) of a sensor module 410 may be executed by a microcontroller 408 and may calculate 350 a desired modular umbrella system elevation angle and/or azimuth angle utilizing received geographic location measurements, heading measurements, and/or time measurements. In embodiments, a microcontroller may transfer desired elevation angle measurements and/or azimuth angle measurements to a motion control module 420. In embodiments, computer-readable instructions stored in a memory of a motion control module 420 may compare 360 desired elevation angle measurements and azimuth angle measurements to a current elevation angle and azimuth angle of the modular umbrella system (calculated from gyroscope measurements, accelerometer measurements, and/or both) to determine movements that a modular umbrella system may make in order to move to a desired orientation. In embodiments, executed computer-readable instructions may calculate an azimuth adjustment measurement to provide to an azimuth motor and/or an elevation adjustment measurement to provide to an elevation motor.

In embodiments, in response to the comparison, computer-readable instructions executed by a processor 310 may communicate 370 a command, signal, message, and/or instructions to an azimuth motor assembly 131 to cause a modular umbrella shading system 100 to rotate to a desired azimuth orientation by moving a distance corresponding to and/or associated with an azimuth adjustment measurement. In embodiments, in response to the comparison, computer-readable instructions executed by a processor 310 may communicate 380 an elevation adjustment measurement to an elevation motor assembly to cause an upper core assembly to rotate with to a desired angle with respect to a lower core assembly (e.g., a desired elevation angle) by moving a distance corresponding and/or associated with elevation adjustment measurement.

In embodiments, in response to reaching a desired elevation angle and/or azimuth angle, computer-readable instructions executed by a processor may start 385 a timer (and/or clock) and after a predetermined time (or time threshold) may re-initiate 390 the modular umbrella orientation positioning process described above. In embodiments, a modular umbrella orientation positioning process may be reinitiated and/or checked every 5 to 7 minutes. In embodiments, a modular umbrella orientation positioning process may be initiated when a modular umbrella system is turned on and/or reset. In embodiments, adjustments may not be made every time a modular umbrella orientation positioning process is initiated because a modular umbrella shading system may not have moved significantly in a measurement timeframe.

In embodiments, a modular umbrella system 100 may also comprise a drone (or unmanned aerial vehicle ("UAV")) system. In embodiments, a UAV system may comprise a UAV (e.g., drone) device 500 and/or a UAV docking port 501 In embodiments, a UAV system may depart from a UAV docking port 501 and fly around an area encompassing and/or surrounding a modular shading system. In embodiments, a UAV device 500 may have a range of 200 meters from a modular shading system. In embodiments, a mobile computing device may communicate with a drone utilizing personal area network protocols including but not limited to WiFi, Bluetooth, Zigbee, etc. In embodiments, computer-readable instructions stored in a memory of a computing device and executable by a processor of a computing device (e.g., SMARTSHADE and/or SHADECRAFT software) may control operations of a UAV device/drone 500. In embodiments, operations may include guiding movement of a drone, communicating measurements and/or data from a drone, activating/deactivating sensors on a drone, and/or activating/deactivating one or more cameras 575 on a drone. For example, in embodiments, a UAV device 500 may comprise one or more camera devices 575. In embodiments, a camera device 575 may capture images, video and/or sound of the environment surrounding a drone/UAV and may transmit and/or communicate images back to a computing device and/or other component of a modular umbrella shading system. In embodiments, for example, an air quality sensor may be installed on a UAV device, make take measurements during flight of the UAV device and may transmit and/or communicate captured measurements and/or readings from an air quality sensor to a sensor printed circuit board, and/or another component and/or assembly on a modular umbrella shading system. Placing sensors on a UAV device 500 may allow for more accurate and comprehensive sensor readings (e.g., measurements may be taken at a number of locations rather than only an exact locations at where a modular umbrella system is installed. In addition, more accurate and comprehensive sensor readings may be obtained at locations unreachable from a ground location (e.g., at higher elevations and/or at locations obscured and/or walled off from a place where an umbrella shading system is installed).

Figure 5:
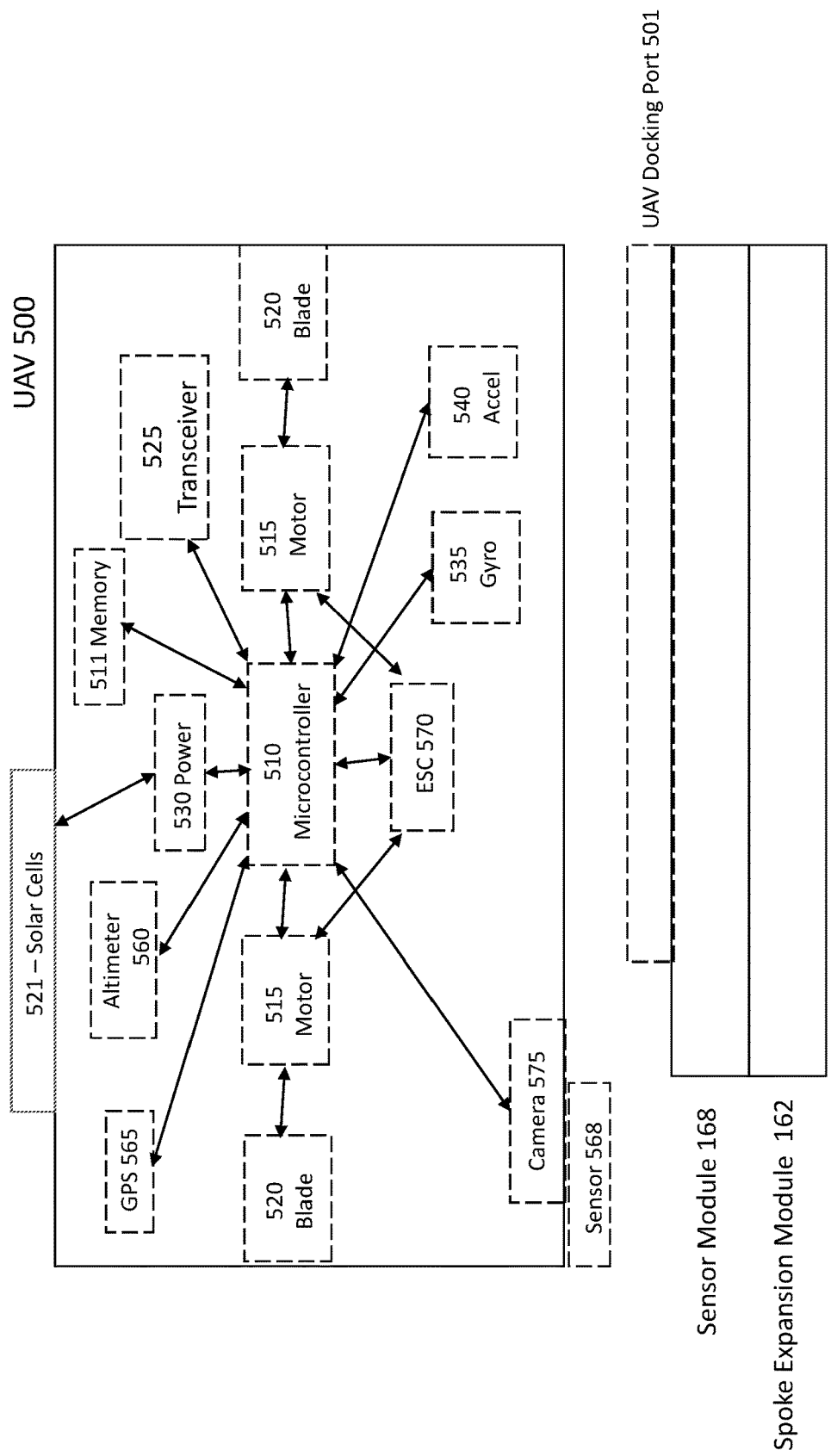
FIG. 5 illustrates an unmanned aerial vehicle (UAV) according to embodiments.

FIG. 5 illustrates a UAV device and a modular umbrella system according to embodiments. In embodiments, a UAV docking port 501 may connect to a UAV device through a latching assembly, a mechanical coupling assembly, and/or through magnetic coupling. In embodiments, a UAV docking port 501 may provide power to a UAV device power source 530 (e.g., a rechargeable battery) through an electrical connection (e.g., wire or connector) and/or through induction coupling (e.g., wireless charging). In embodiments, a UAV docking port 501 may be integrated into a sensor housing 168 or may be integrated into a spoke/arm connection housing 162. In embodiments, a UAV docking port 501 may be placed on a surface of a sensor housing 168 and/or a spoke/arm connection housing 162

In embodiments, a modular umbrella system may comprise a drone. In embodiments, a drone may be referred to as an unmanned aerial vehicle. FIG. 5 illustrates an unmanned aerial vehicle (UAV) according to embodiments. In embodiments, a UAV 500 comprises a frame, a microcontroller board 510, one or more rotors or motors 515, one or more propellers/blades 520, one or more wireless transceivers 525, and a power source 530. In embodiments, a UAV 500 may further comprise one or more gyroscopes 535 and/or one or more accelerometers 540. In embodiments, a UAV may comprise an altimeter 560. In embodiments, a UAV may comprise an electronic speed controller (ESC) 570. In embodiments, a UAV may comprise a GPS and/or GLONASS transceiver 565. In embodiments, a UAV may comprise one or more cameras 575.

In embodiments, a UAV 500 may be controlled by instructions transmitted by a computing device (e.g., a computing device in a mobile computing device and/or a computing device in a modular umbrella shading system). In embodiments, a computing device may be a mobile computing device having computer-readable instructions executed by a processor to interface and/or control a modular shading system and/or a UAV. In embodiments, a computing device may be a modular umbrella system computing device 136 having computer-readable instructions stored thereon and executable by a processor. In embodiments, a modular umbrella shading system may comprise a user interface (e.g., on a display) that may control and/or interface to a UAV 500. In embodiments, a computing device may comprise a transceiver that communicates with one or more transceivers 525 in a UAV 500. In embodiments, a mobile computing device may communicate with a cloud-based server, which may communicate with one or more transceivers in a UAV 500.

In embodiments, a power source 530 may be a rechargeable battery. In embodiments, a rechargeable battery may allow for up to 12 hours of operation. In embodiments, a UAV 500 may comprise one or more solar panels or cells 521. In embodiments, one or more solar panels or cells 521 may convert sunlight into electricity which may be transferred to a rechargeable battery 530 in order to charge a rechargeable battery. In embodiments, a UAV may be powered via UAV docking port 501 on a modular shading umbrella system 100.

In embodiments, a UAV 500 may comprise a microcontroller (e.g., a single board microcontroller) 510. In embodiments, a microcontroller 510 may include a processor, a memory, computer-readable instructions stored in the memory 511 and executable by the processor/microcontroller 510. In embodiments, a microcontroller 510 may control operations of one or more motors 515 of the UAV (and thus blades and/or propellers 520), may communicate and/or interface with inertial components such as gyroscopes 535 and/or accelerometers 540, may communicate and/or interface with landing sensors 568 and/or other sensors, may communicate and/or interface with cameras 575, and/or may communicate and/or interface with a power source 530 (e.g., rechargeable battery) and/or one or more solar cells or arrays 521. In embodiments, a single board microcontroller may be an Arduino board, a DJI A2 or other similar controllers. In embodiments, a UAV may also comprise an electronic speed controller (ESC) 570. In embodiments, an electronic speed controller 570 may be integrated into or on a same board as a microcontroller. In embodiments, a ESC 570 may determine and control speed, velocity and/or acceleration of a UAV by communicating messages, instructions, signals and/or commands to one or more motors 515 to tell motors how fast to operate and spin propeller blades 520. In embodiments, an ESC 570 may provide different speeds to different motors in order to move in specific directions.

In embodiments, an inertial measurement unit may comprise one or more gyroscopes 535 and/or one or more accelerometers 540. In embodiments, UAVs may be exposed to many external forces (wind, rain, physical objects, etc.) coming from different directions. In embodiments, external forces may impact a drone's yaw, pitch and/or roll, and thus impact a UAV's flight movement. In embodiments, one or more gyroscopes 535 detect such changes in position (e.g., changes in yaw, pitch and roll) and communicate this information to a microcontroller 510, which can then interface with an electronic speed control (ESC) 570, motors 515 and/or propellers/blades 520. In embodiments, gyroscopes feedback information on position hundreds of time each second. In embodiments, one or more accelerometers 540 may also measure changes in an UAV's orientation relative to an object's surface (e.g., Earth's surface). In embodiments, one or more accelerometers 540 communicate measurement changes in a UAV's orientation to a microcontroller 510, which in turn may communicate messages, commands and/or instructions to ESCs 570, which in turn may communicate messages, commands and/or instructions to motors 515 and/or propeller/blades 520.

In embodiments, a UAV may comprise an altimeter 560. In embodiments, an altimeter 560 may measure an altitude of a UAV and may communicate altitude measurements to a microcontroller 510. In embodiments, a microcontroller or controller or processor 510 may verify, compare and/or check altitude measurements against desired altitude measurements. In response to the verification and/or comparison, a microcontroller 510 may which in turn may communicate messages, commands and/or instructions to ESCs 570, which in turn may communicate messages, commands and/or instructions to motors 515 and/or propeller/blades 520.

In embodiments, a UAV 500 may comprise a GPS or GLONASS transceiver 565. In embodiments, a GPS transceiver 565 may capture and/or calculate position readings for a UAV 500 and communicate these measurement and/or calculated positions to a microcontroller 510. In embodiments, a microcontroller 510 may utilize GPS measurements and/or readings to determine a geographic location of a UAV. In embodiments, a microcontroller 510 may utilize GPS measurements to identify take off positions and/or landing positions. In embodiments, a GPS transceiver 565 may be located on a microcontroller 510. In embodiments, a GPS transceiver 565 may be located in an inertial measurement unit.

In embodiments, a UAV 500 may comprise landing sensors 568. In embodiments, landing sensors 568 may be light-based sensors and/or ultrasonic sensors. In embodiments, landing sensors 568 may be located on a bottom surface of a UAV 500. In embodiments, landing sensors 568 may communicate measurements and/or readings regarding a landing surface (e.g., is a landing surface present, how far is it away (based on sound and/or light reflection)) to a microcontroller 510. In embodiments, a microcontroller 510 may communicate messages, commands and/or instructions to ESCs 570, which in turn may communicate messages, commands and/or instructions to motors 515 and/or propeller/blades 520 to move a UAV to a landing position (e.g., a modular umbrella system landing spot and/or landing dock).

In embodiments, a UAV 500 may comprise a landing system may comprise one or more wireless transceivers 525. In embodiments, a wireless transceiver 525 may communicate commands, instructions, signals and/or messages between wireless transceivers in a modular umbrella system 100. In embodiments, a wireless transceiver 525 may communicate commands, instructions, signals and/or messages between wireless transceivers in a mobile computing device such as a smartphone, a tablet, a controller, a laptop computer etc. In embodiments, computer readable instructions, stored on a memory of a mobile computing device (and or modular umbrella system) may be executed on a processor (e.g., in a SMARTSHADE application) and one option in a software application may be UAV operation and/or control. In embodiments, SMARTSHADE software application may comprise, among other things, a UAV or drone icon, which if selected, further presents various modes of UAV operation and control. In embodiments, a SMARTSHADE software application may provide instructions as to flight of a UAV, take off and/or landing of a UAV, movements in direction of a UAV, activation/deactivation of a UAV camera, and activation/deactivation of other sensors and/or components of a UAV. In embodiments, a SMARTSHADE application may communicate messages, instructions, commands and/or signals utilizing a wireless transceiver in a mobile computing device and a wireless transceiver in a UAV.

In embodiments, a UAV 500 may comprise one or more cameras 575. In embodiments, one or more cameras may be placed on a bottom surface of a UAV 500 to capture images, sounds and/or videos of an area adjacent to and/or surrounding a modular umbrella system 100. In embodiments, a microcontroller 510 may activate and/or deactivate one or more cameras 575. In embodiments, one or more cameras 575 may capture images, sounds and/or videos and may communicate captured images, sounds and/or videos to a microcontroller 510, which may store captured images, sounds and/or videos in a memory of a UAV and/or a microcontroller 510. In embodiments, a microcontroller 510 may communicate and/or transfer captured images to a computing device 136 in a modular umbrella system 100, which in turn may store captured images in a memory of a modular umbrella system 100 and/or transfer captured images, video and/or sound to other computing devices (e.g., devices in a cloud) and/or mobile computing devices linked to a modular umbrella system (e.g., mobile computing devices utilizing and executing SMARTSHADE software). In embodiments, a UAV 500 may communicate captured images, video and/or sound via a wireless transceiver 525 to a mobile computing device (which utilizes its own wireless transceiver for communication) without first communicating captured images, videos and/or sound to a modular umbrella system 100. In other words, a UAV 500 may transfer and/or communicate images captured by its camera 575 directly to a mobile computing device or indirectly to a web server which in turn communicates the images, videos and/or sound to the mobile computing device (without passing through a modular umbrella system).

Figure 6:
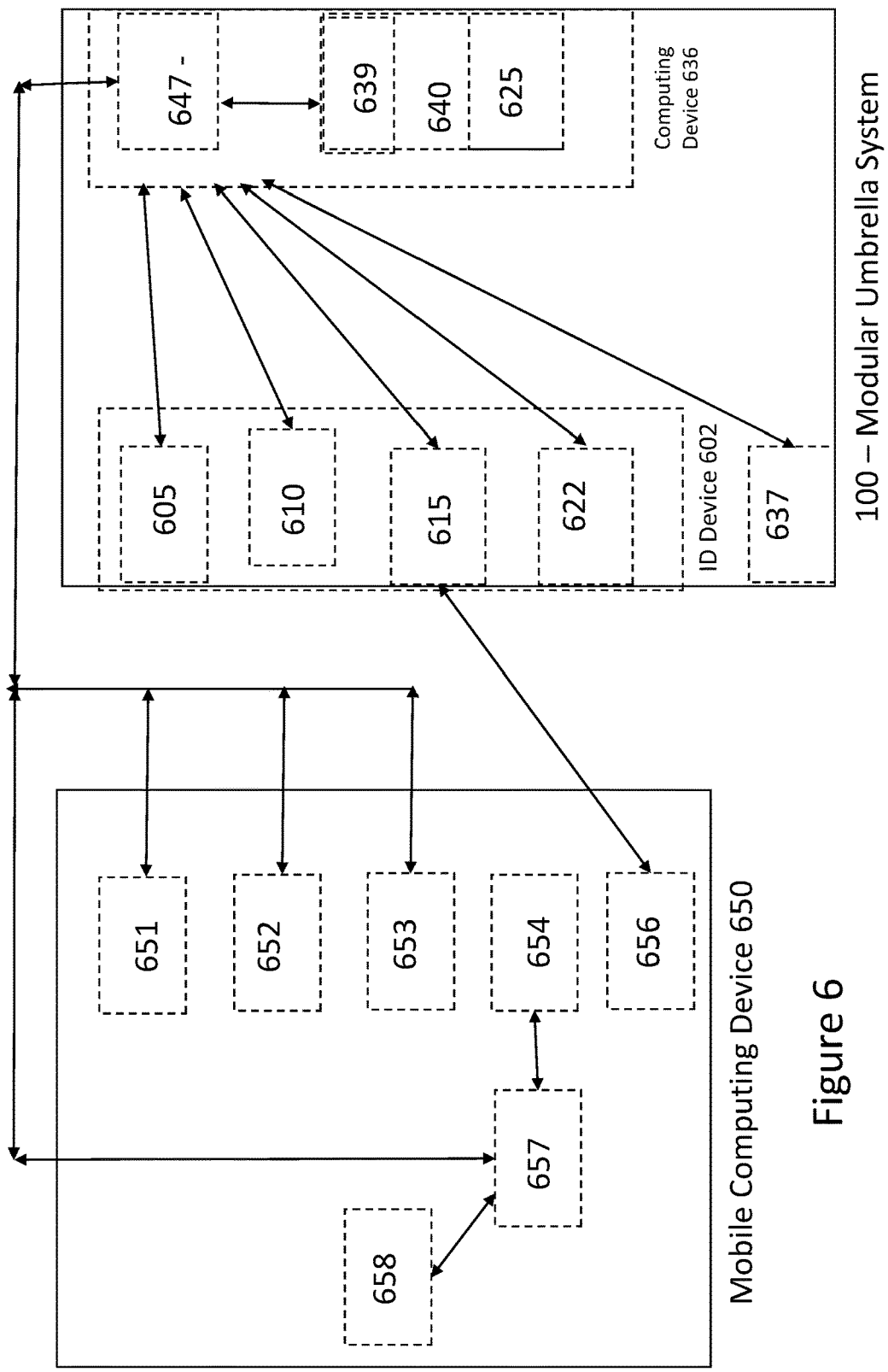
FIG. 6 illustrates a modular umbrella system including an identification system according to embodiments.

FIG. 6 illustrates a modular umbrella system including an identification system according to embodiments. In embodiments, a modular umbrella system 100 may comprise an identification system or module 602. In embodiments, an identification system or module 602 may comprise a retinal scanner 605. In embodiments, an identification system or module 602 may further comprise (or alternatively comprise) a fingerprint scanner 610. In embodiments, an identification system 602 may further utilize (or alternately utilize) a NFC sensor 615 (or 139 in FIG. 1). In embodiments, an identification system 602 may further utilize (or alternatively utilize) a microphone 622 and/or voice recognition module 625 to identify an authorized user. In embodiments, an identification system 602 may further utilize (or alternatively utilize) one or more cameras 637 to identify an authorized user utilizing a facial recognition module 639. In embodiments, an identification system 602 may be implemented 1) within a standalone umbrella system (e.g., not being controlled by a mobile computing device); 2) in conjunction and/or combination with a mobile computing device software application (e.g., SMARTSHADE), and/or 3) in conjunction and/or combination with a cloud-based server.

In embodiments where an identification system 602 is implemented within a standalone assembly (e.g., a modular umbrella system), an identification assembly may communicate with a separate computing device 636 (e.g., a Raspberry Pi computing device) within the modular umbrella system 100. For example, in embodiments, a retinal scanner 605, a fingerprint scanner 610, a camera 637 and/or a NFC sensor 615 may be located on a skin assembly of a modular umbrella system 100. In embodiments, a retinal scanner 605, a fingerprint scanner 610, a camera 637 and/or a NFC sensor 615 may be located on or integrated within or into a core assembly module 130 of a modular umbrella system 100.

In embodiments, a user may activate a retinal scanner 605 and may place an eye in front of a retinal scanner 605. In embodiments, a fingerprint scanner 610 may be activated by a user placing a finger and/or thumb onto a fingerprint scanner 610. In embodiments, a user 130 may activate one or more cameras 637, stand within a view of a camera and have one or more cameras 637 capture an image of a user (e.g., an image of a user's face). In embodiments, a captured image (e.g., a retinal scan, a fingerprint scan/image and/or a facial image) may be communicated from a retinal scanner 605, a fingerprint scanner 610 and/or a camera 637 to an integrated computing device 636. In embodiments, a captured image may be communicated via a wired connection and/or may be communicated wirelessly using a PAN transceiver to an integrated computing device 636.

In embodiments, an integrated computing device 136 or 636 may comprise a processor or controller 647, one or more volatile memories and/or non-volatile memories 640, a wireless transceiver, computer-readable instructions stored in the non-volatile memory (e.g., facial recognition module 639 and/or voice recognition module 625), and/or one or more input output ports. In embodiments, for example, where a fingerprint image is communicated from a fingerprint scanner 610, computer-readable instructions executed by a processor or controller may store a communicated fingerprint image in a memory 640 (e.g., volatile memory or non-volatile memory) and/or may compare a communicated fingerprint image to one or more authenticated fingerprint images stored in one or more memories 640. In embodiments, a processor or controller 647 may communicate an authentication message to a display panel and/or a fingerprint scanner 610 in response to a communicated fingerprint image matching one of the stored authenticated fingerprint images (which may allow a user to interface with and/or operate a modular umbrella system 100). In embodiments, a processor or controller 647 may communicate a denial message to a display panel and/or fingerprint scanner 610 in response to a communicated fingerprint image not matching authenticated fingerprint images in one or more memories. Similarly in embodiments, a retinal scanner 605 may communicate a captured retinal image to images stored in one or more memory devices 640 and computer-readable instructions, stored in one or more memory devices 640 and executable by a processor or controller 647, may compare a captured retinal image to authenticated retinal images stored in one or more memory devices 640. Similarly, in embodiments, a processor or controller 647 may communicate an authentication message (in response to a match) or a denial message (in response to no match) to a control panel and/or a retinal scanner 605 to allow and/or deny authorization to interact with and/or utilize a modular umbrella system 100.

In embodiments, for example, where a NFC sensor is utilized for authentication, a device comprising a NFC sensor comes into a proximity with a NFC sensor 615 in a modular umbrella system 100. In embodiments, for example, a device with the NFC sensor 615 communicates authentication information to a processor 647 in an integrated computing device 636. In embodiments, computer-readable instructions executed by a processor 647 compare the communicated authentication information to stored authentication information to verify if a device (and user) with the NFC sensor can utilize a modular umbrella system 100. In embodiments, a computer-readable instructions executable by processor or controller 647 may communicate an authentication message (if authentication information is verified) or a denial message (if authentication information is not verified) to the device comprising the NFC sensor. In response to being authenticated, a device may interface with and operate a modular umbrella system 100 (and if denied, the device may not interface with and/or operate the modular umbrella system 100).

In embodiments, for example, where voice recognition may be utilized for authentication, a modular umbrella system 100 may further comprise a microphone 622 and/or a voice recognition engine or module 625. In embodiments, a voice recognition engine 625 may be separate from an integrated computing device 636 (e.g., on a separate circuit board and/or chip and/or utilizing computer-readable instructions store in a memory separate and apart from an integrated computing device 636. In embodiments, a voice recognition engine or module 625 may be integrated and/or part of the computing device 636 or 136. In embodiments utilizing voice recognition, a user may speak (e.g., or speak a password and/or code) which may be input and received via a microphone 622. In embodiments, a microphone 622 may transfer the spoken words to a voice recognition engine 625, which may convert a spoken phrase to a digital audio file. In embodiments, computer-readable instructions executed by a processor 647 may store spoken digital audio file and/or may compare the spoken digital audio file to authenticated audio files stored in one or more memory devices. In embodiments, a processor or controller 647 may communicate an authentication message to a display panel and/or voice recognition engine 625 (and then to a sound reproduction device (e.g., speaker) in response to a spoken audio file matching one of the stored authenticated audio files (which may allow a user to interface with and/or operate a modular umbrella system 100 using a voice recognition engine). In embodiments, a processor or controller 647 may communicate a denial message to a display panel and/or voice recognition engine 625 (and then to a sound reproduction device) in response to a spoken audio file not matching authenticated audio files in one or more memory devices 640.

In embodiments, a modular umbrella system 100 may further utilize (or alternatively utilize) a facial recognition module 639 and/or camera 637 to authenticate users. In embodiments, one or more cameras 637 may capture an image of a potential user (e.g., a face or other identifiable area) and may communicate a captured image to an integrated computing device 637. In embodiments, computer-readable instructions, stored in one or more memories 640, and executed by a processor or controller 647 of an integrated computing device 636 may store a captured user image and/or may compare a captured user image to authenticated user images. In embodiments, a comparison may be performed utilizing a facial recognition engine 639 located or integrated within the computing device. In embodiments, a facial recognition engine 639 separate from an integrated computing device 136 (e.g., on a separate circuit board and/or chip and/or computer-readable instructions stored in a different memory device) may perform a comparison. In embodiments, a processor or controller 647 may communicate an authentication message to a display panel and/or camera 637 in response to a captured image matching one of the stored authenticated images (which may allow a user to interface with and/or operate a modular umbrella system 100). In embodiments, a processor or controller 647 may communicate a denial message to a display panel and/or camera 637 (and then to a in response to a captured image not matching authenticated images stored in the non-volatile memory.

In embodiments, a user may be operating a mobile computing device 650 (e.g., a smartphone, a tablet, a laptop, etc.). In embodiments, a modular umbrella system 100 in combination and/or conjunction with a mobile computing device 650 may perform authentication of a user and/or a device. In embodiments, a mobile computing device 650 may comprise a retinal scanner 651 (or retinal scanning processing software to analyze a picture captured by a smartphone camera). In embodiments, a mobile computing device 650 may comprise a fingerprint scanner 652 (or fingerprint scanning software to analyze a picture captured by a smartphone camera 653). In embodiments, a mobile computing device 650 may comprise a microphone 654 and/or voice recognition software to capture and convert a user's spoken command. In embodiments, a mobile computing device 650 may comprise a camera 653 to capture an image of a user's face (and/or facial recognition software to analyze the captured image). In embodiments, a mobile computing device 650 may comprise a controller and/or processor 657. In embodiments, a processor and/or controller 657 may comprise one or more memories which may store computer-readable instructions (e.g., facial recognition software, voice recognition software, fingerprint scanning software and/or retinal scanning software). In embodiments, a mobile computing device 650 may comprise a memory 658 outside of a controller or processor 657, where the memory stores computer-readable instructions (e.g., facial recognition software, voice recognition software, fingerprint scanning software and/or retinal scanning software) executable by a processor and/or controller 657. In embodiments, a mobile computing device 650 may comprise a NFC sensor 656 which can be paired with a NFC sensor 615 in a modular umbrella system 100 to perform an authentication process, as described previously In embodiments, a mobile computing device 650 may communicate a captured image to a modular umbrella system 100 (if a retinal scanner 651, retinal analyzing software, fingerprint scanner 652, fingerprint analyzing software, camera 653, and/or facial recognition software is resident on a mobile computing device 650). In embodiments, a mobile computing device 650 may communicate a captured image to an integrated computing device 636 in a modular umbrella system 100. In embodiments, computer-readable instructions executed by a processor or controller 647 on an integrated computing device 636 may store a received captured image communicated from a mobile computing device 650 in one or more memories 640 of an integrated computing device 636 and/or compare a communicated captured image from the mobile computing device 650 to existing authenticated images stored in one or memories 640 of the integrated computing device 636. In embodiments, a processor or controller 647 may communicate an authentication message to a mobile computing device 650 in response to a captured image matching one of the stored authenticated images (which may allow a mobile computing device 650 to operate and/or control a modular umbrella system 100). In embodiments, a processor or controller 647 may communicate a denial and/or refusal message to a mobile computing device 650 in response to a captured image not matching authenticated images stored in one or more memories 650, which would prevent a user and/or the mobile computing device 650 from interacting with a modular umbrella system 100.

In embodiments where a mobile computing device utilizes a NFC sensor 655 for authentication, authentication may operate in a fashion as described above. In embodiments where a mobile computing device 650 utilizes a microphone 654 and/or voice recognition software for authentication, a microphone 654 on a mobile computing device 650 captures a spoken command. In embodiments, computer-readable voice recognition instructions (e.g., in a voice recognition engine or module) executing on a mobile computing device processor 657 convert a received command to an audio file (e.g., a digital audio file). In embodiments, a mobile computing device 650 may communicate a captured audio file to an integrated computing device 636 or 136 (or a voice recognition engine in the modular umbrella system). In embodiments, a processor or controller 647 may store a received captured audio file communicated from a mobile computing device 650 in one or more memories 640 of an integrated computing device 636 and/or may compare a communicated captured audio file from the mobile computing device 650 to existing authenticated audio files stored in one or more memories of the integrated computing device 636. In embodiments, a processor or controller 647 may communicate an authentication message to a mobile computing device 650 (and then to a sound reproduction device (e.g., speaker) in the mobile computing device 650 in response to a spoken audio file matching one of the stored authenticated audio files (which may allow a mobile computing device 650 to interface with and/or operate a modular umbrella system 100 using voice commands). In embodiments, a processor or controller 647 may communicate a denial or rejection message to a mobile computing device 650 (and then to a sound reproduction device in the mobile computing device 650) in response to a spoken audio file not matching authenticated audio files in one or more memories. In this case, a user of the mobile computing device 650 may not be authenticated and not utilize and/or operate a modular umbrella system 100.

Figure 7:
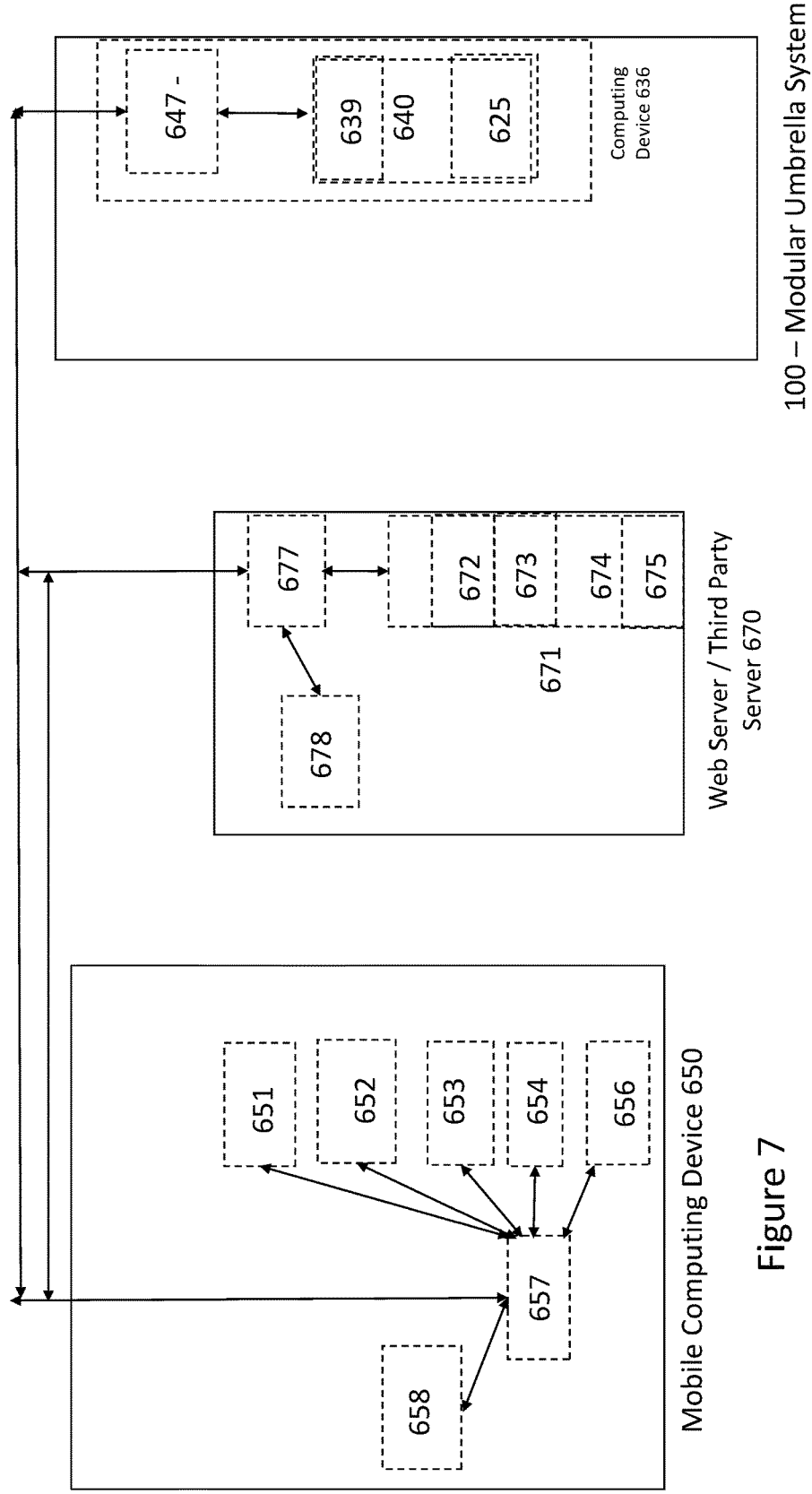
FIG. 7 illustrates use of a web server and/or cloud-based server for authentication of a user and/or a mobile computing device utilizing a modular umbrella system.

FIG. 7 illustrates use of a web server and/or cloud-based server for authentication of a user and/or a mobile computing device utilizing a modular umbrella system. In embodiments, where a web server or a cloud-based server 670 are utilized for authenticating users and/or mobile computing devices 650 to interact with a modular umbrella system 100, authentication devices and/or modules (e.g., retinal scanners, fingerprint scanners, voice recognition software, facial recognition software and/or NFC sensors) may be located within either a modular umbrella system (e.g., an integrated computing device in a modular umbrella system or other places) or authentication devices and/or modules (e.g., retinal scanners 651, fingerprint scanners 652, microphones 654, voice recognition software, cameras 653, facial recognition software and/or NFC sensors 656) may be located within a mobile computing device 650. In embodiments, authentication may be performed utilizing web-based servers and/or cloud-based servers 670 to provide more security during the authentication process (e.g., a third party authentication process may be utilized and/or a more secure server may be utilized as compared to an integrated computing device in a modular umbrella system 100). In addition, utilizing a web-based and/or cloud-based authentication system 670 and/or process may allow one or more modular umbrella systems 100 to utilize a same authentication process and not require authentication information to be communicated to each modular umbrella system 100. Further, in embodiments, some modular umbrella systems 100 may not have integrated computing devices and/or enough storage on an integrated computing device 100 to be able to handle authentication requests. In addition, some modular umbrella system 100 may not have authentication software (e.g., facial recognition software, voice recognition engine, fingerprint and/or retinal image analyzing software) installed on an integrated computing device and these processes and/or procedures may be performed on a web server and/or a cloud-based server 670. In embodiments, for example captured information (e.g., images from cameras 653 for facial recognition, retinal scanners 651, fingerprint scans from finger print scanners 652, audio files from microphones 654 for voice recognition, authentication information from devices with NFC sensors 656) may be communicated from a mobile computing device 650 to a web server, an application server, and/or a cloud-based server 670.

In embodiments, computer-readable instructions may be stored on one or more memories 671 of a web server, application server and/or cloud-based server 670 and executed by a processor 677. In embodiments, computer-readable instructions may be referred to as SMARTSHADE software. In embodiments, computer-readable instructions may comprise a facial recognition engine or module 671, a voice recognition module or engine 672, retinal scanning software 673, and/or fingerprint scanning software 675, may be executed by a processor 677 and may process and/or analyzed mobile device captured information ((e.g., images from a camera 653 for facial recognition, retinal scans from a retinal scanner 651, fingerprint scans from a fingerprint scanner 652, audio files from voice recognition from microphones 654, authentication information from devices with NFC sensors 656) may be communicated directly from a mobile computing device 650 (e.g., utilizing a processor or controller 657 to a web server, an application server, and/or a cloud-based server 670 (utilizing a processor and/or controller 677)). In embodiments, computer-readable instructions executable by a controller or processor 677 of a web server, application server and/or cloud-based server 670 may compare captured information against existing authentication information to verify that a user and/or mobile computing device 650 sending and/or communicating the captured information is an authorized user of a modular umbrella system 100. In embodiments, existing authentication information may comprise authenticated facial images, authenticated audio file, authenticated retinal scans and/or authenticated fingerprints and/or other biometric information stored in one or more memories 671 or 678. In embodiments, computer-readable instructions may be executed by a processor 677 on a web server, application server and/or cloud-based server 670 may communicate an authentication message and/or instructions to a modular umbrella system 100 to verify that a user is able to operate and/or control a modular umbrella system 100. In embodiments, an authentication message may be displayed on a control and audibly reproduced on a sound reproduction device such as a speaker (and likewise may transmit a denial and/or no authentication message if match is not found). In embodiments, computer-readable instructions may be executed by a processor 677 on a web server, application server and/or cloud-based server 670 may communicate an authentication message and/or instructions to a mobile computing device 650 to verify that a user is able to operate and/or control a modular umbrella system 100. In embodiments, an authentication message may be displayed on a screen of a mobile computing device 650 and/or audibly reproduced on a sound reproduction device such as a speaker of a mobile computing device 650 (and likewise may transmit a denial and/or no authentication message if match is not found).

Figure 8:
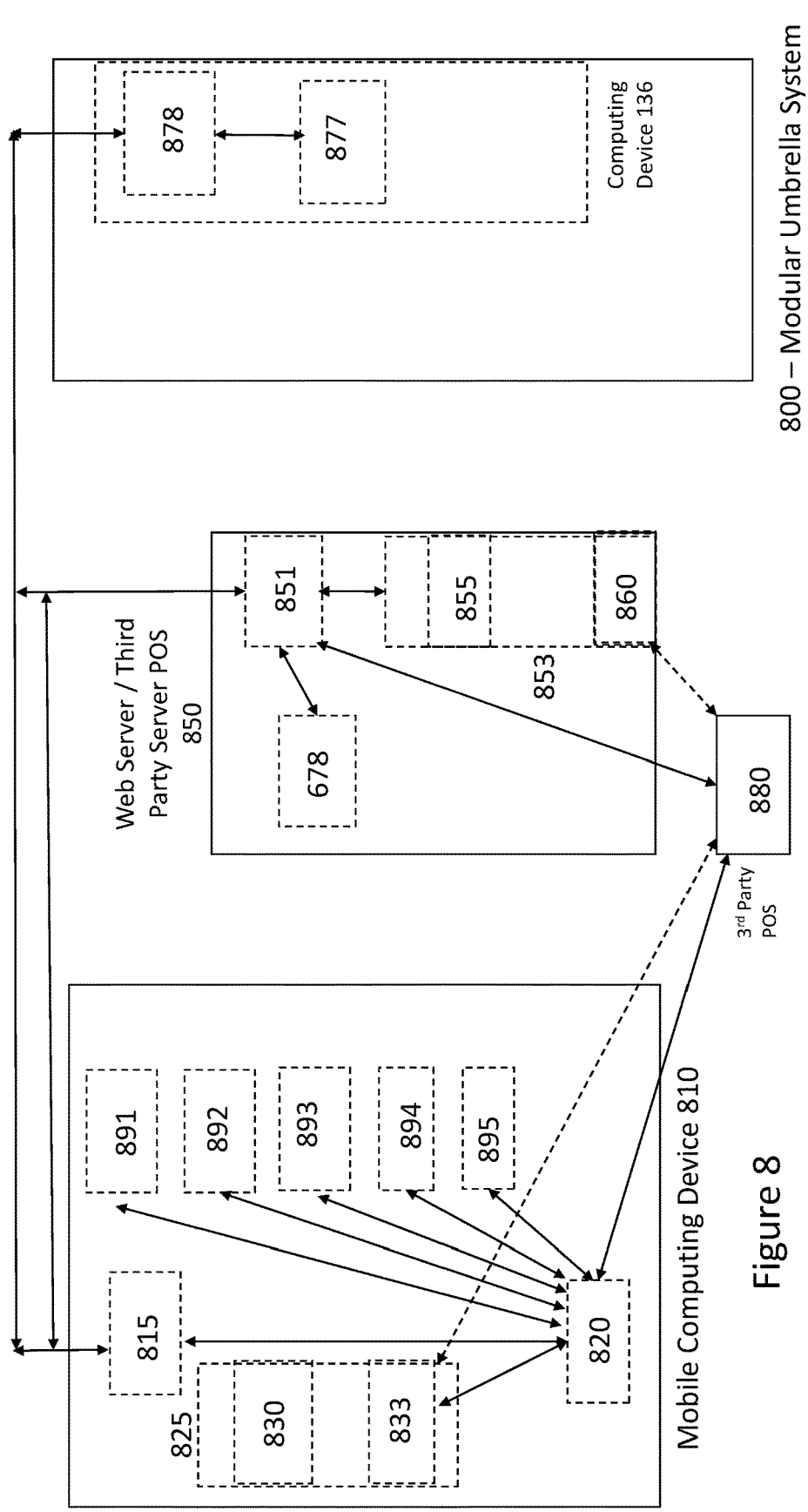
FIG. 8 illustrates a mobile point-of-sale system utilizing a mobile computing device, one or more modular umbrella systems and a server according to embodiments.

FIG. 8 illustrates a mobile point-of-sale system utilizing a mobile computing device, one or more modular umbrella systems and a server according to embodiments. In embodiments, a mobile computing device 810 may comprise a wireless transceiver and/or a cellular transceiver 815, one or more processors 820 and one or more memories 825. In embodiments, a mobile computing device may comprise computer-readable instructions 830 stored in one or more memories 825, which when executed by a processor 820, may control operation and/or communicate with a modular umbrella system 100. In embodiments, the computer-readable instructions 830 may be called a software application, an app, a mobile app and/or may be referred to as SMARTSHADE software. In embodiments, computer-readable instructions 830 may also perform point-of-sale transactions with a modular umbrella system 800. In embodiments, a web server and/or cloud-based server 850 may comprise one or more processors 851, one or more memories 853, and an umbrella point of sale (POS) software application 855 (e.g., computer-readable instructions). In embodiments, a web server and/or cloud-based server 850 may comprise one or more memories 853 housing a third-party POS software application programming interface 860. In embodiments, a user may utilize a mobile computing device 810 to perform and/or execute POS transactions and may purchase umbrella-related products and/or accessories, products recommended by vendors of a modular umbrella system 800, products recommended in response to, for example, a SMARTSHADE software application has analyzed modular umbrella sensors and/or assemblies, (e.g., recommending sunscreen when sun intensity measurement from a UV sensor is high, recommending particle masks when an air quality measurement from an air quality sensor is low). In embodiments, if a component fails, a component and/or an assembly may communicate and/or transmit an error message to a controller or processor (e.g., a controller and/or processor in a motion control PCB and/or an integrated computing device). In embodiments, a controller and/or processor may receive a measurement and/or communication from a component and/or assembly, analyze the measurement and/or communication and determine a component and/or assembly may be malfunctioning. In embodiments, in either case (e.g., error message received and/or malfunction determined), a controller and/or processor may notify a user that a component and/or assembly is malfunctioning and may need to be replaced. For example, any of a number of sensors (e.g., UV sensors, wind sensors, proximity sensors, humidity sensors, and/or temperature sensors) may transmit an error message and/or an out-of-tolerance measurement and/or reading and a controller and/or processor in a motion control PCB and/or integrated computing device may initiate ordering of components, assemblies, and/or consumables through a POS module in a SMARTSHADE software application. In embodiments, a modular umbrella system may have accessories and consumables which may need to be reordered, e.g., such as fuses and/or lights/bulbs. In embodiments, a SMARTSHADE software application may allow reordering and/or replacement parts through a POS component and/or module.

In embodiments, a mobile computing device 810 generating and/or initiating POS transactions (e.g., using POS functionality in a SMARTSHADE application 830) may allow users to rent one or more umbrellas at a hotel, venue, stadium, or other meeting place or make reservations for an umbrella system at a hotel, venue, and/or stadium. In embodiments, a mobile computing device 810, executing a SMARTSHADE software application 830 and performing POS transactions, may pay for a user's hotel and/or restaurant bills by interfacing with a hotel and/or restaurant POS system through a application programming interface.

In embodiments, a mobile computing device 810, a modular umbrella system 800, a web server or application server and/or a cloud-based server 850 may communicate and/or interface with each other to engage in POS transactions. In embodiments, an application program interface (API) 833 may be resident within one or more memories 825 of a mobile computing device 810 and/or an application program interface 860 may be resident within one or more memories 853 of an application server, web server and/or cloud-based server 850 and either one of POS application program interfaces (833 or 860) may communicate and/or interact with a third party POS system (Google Wallet, Apple Pay) 880 to engage in financial transactions with the third party POS system 880. In embodiments, application program interfaces (833 or 860) may utilize controllers and/or processors (820 or 851) to communicate and/or interface with third party POS systems 880.

In embodiments, a user may interact directly with a modular umbrella system 800 and engage in POS financial transactions. In embodiments, computer-readable instructions, stored on a memory 877 of an integrated computing device 136, may generate a menu with financial transaction options on a display of a modular umbrella system 800 (e.g., a SMARTSHADE application having POS functionality) or a third party POS software application and/or app. In embodiments, a screen may be a control panel and/or a display attached to and/or connected to a modular umbrella system 800. In embodiments, one or more financial and/or commerce transactions may be selected (e.g., purchase sunscreen, reserve umbrella system for an additional timeframe (e.g., an hour)), and financial transaction data and/or information may be communicated to a web server and/or a cloud-based server 850.

In embodiments, a web server or a cloud-based server 850 may be partitioned and/or a portion of the cloud-based server 850 may be established as a portion of a SMARTSHADE POS system (or modular umbrella systems POS system). In embodiments, a web server or application server 850 may be setup, established and/or housed under a control of an owner (e.g., an owner of a host facility). In embodiments, a cloud-based server 850 may be established at a third-party facility, but may be partitioned for utilization as a modular umbrella system POS. In embodiments, cloud-based servers 850 may be setup as private areas for clients and/or may be shared by multiple clients with appropriate security in place to protect confidentiality and security of user's financial data and/or information.

In embodiments, a web server, application server and/or cloud-based server 850 may receive financial transaction requests from a mobile computing device 810 and/or a modular umbrella system 800 and may communicate financial transaction requests to vendors and/or other parties to further process and/or complete the financial transaction request. In embodiments, a web server, application server and/or cloud-based server 850 may generate a record (e.g., a database request) of the financial transaction request and store a financial record transaction in a memory 853 and/or database of a web server, application server and/or cloud-based server 850. In embodiments, a web server, application server and/or cloud-based server 850 may communicate a financial transaction completion status and/or financial transaction record to a modular umbrella system 800. In embodiments, a modular umbrella system 800 may receive a financial transaction record and/or financial transaction status in a memory 877 of an integrated computing device 136. In embodiments, a processor and/or controller 878 in an integrated computing device 136 may generate a message to a display to inform a user and/or operator of a status and record of a requested financial transaction.

In embodiments, computer-readable instructions loaded in a memory of a mobile computing device may be executed by a processor of a mobile computing device to perform POS functions. In embodiments, as mentioned above, computer-readable instructions may be part of a SMARTSHADE software application that is installed in a memory 825 of a mobile computing device 810 that also controls and/or operates a modular umbrella system 800. In embodiments, a mobile computing device 810 with software installed may be referred to as a mobile point of sale terminal (mPOS). In embodiments, a modular umbrella system icon (or software application) may be selected via a display of a mobile computing device. In embodiments, a POS portion and/or module may also be selected via a display of a mobile computing device. In embodiments, a POS portion and/or module may be selected via an icon and/or via voice recognition. In embodiments, financial transaction opportunities, options and/or selections may be presented and/or recommended via a menu and/or display screen and one or more financial transaction requests may be selected for execution and/or engagement. In embodiments, a financial transaction request may be received and communicated to a modular umbrella system 800. In embodiments, for example, financial transaction requests may be communicated to an integrated computing device 136 in a modular umbrella 800 via a wireless transceiver. In embodiments, the computer-readable instructions executable by a processor of an integrated computing device 136 may receive a financial transaction requests from a mobile computing device 810 and may store financial transaction requests (and associated transaction information) in a memory 877 of an integrated computing device 136. In embodiments, computer-readable instructions executable by a processor of an integrated computing device 136 may communicate financial transaction request information to a web server, application server, cloud-based server 850 (e.g., or to a third-party POS server 880 via an application communication interface (API). In embodiments, a web server, application server and/or cloud-based server 850 may receive financial transaction requests and contact vendors or other third parties to further process and/or complete one or more requested financial transaction requests. In embodiments, a web server, application server and/or cloud-based server 850 may generate a record of the financial transaction and store a financial record transaction in a memory and/or database of a web server, application server and/or cloud-based server 850. In embodiments, a web server, application server and/or cloud-based server 850 may communicate a financial transaction completion status and/or financial transaction record to a modular umbrella system 800. In embodiments, a modular umbrella system 800 may receive a financial transaction record and/or status and store such in a memory 877 of an integrated computing device 136. In embodiments, a modular umbrella system 800 may communicate a financial status record and/or status to a mobile computing device 810, where such information may be presented on a display.

In embodiments, a mobile computing device 810 may communicate one or more financial transaction requests directly to a web server, application server, and/or cloud-based server 850 (or to a third party POS server 880 via an API) without having a modular umbrella system 800 as an intermediary. This may be a preferred method of operation for mobile computing devices 810 having a SMARTSHADE software application installed thereon (e.g., a software application to control and/or operate a modular umbrella system 800 and/or engage in umbrella-related POS transactions).

In embodiments, a mobile computing device 810 may incorporate devices to receive financial information. In embodiments, a mobile computing device 810 may comprise a NFC sensor 891, a chip reader 892, a bar code reader 893, a docking station and/or sled accessory 894, and/or a card reader 895 to more efficiently receive and/or capture financial transaction information to be submitted in financial transaction requests. In embodiments, a user or operator may also manually enter a financial transaction request into an input screen of a POS portion of SMARTSHADE software. In embodiments, a chip reader 892 may read and/or capture authentication information and/or financial information from a credit and/or debit card and may communicate and/or transfer this information to a SMARTSHADE software application (and may utilize a processor and/or controller 820) to include as part of a financial transaction request. In embodiments, a bar code reader 893 may read and/or capture and provide financial information from a bar code (QR code) on a product, a display, and or a document and may communicate and/or transfer this information to a SMARTSHADE software application (utilizing a processor and/or controller 820) to include as part of a financial transaction request. In embodiments, a docking station and/or sled accessory 894 may be utilized to capture financial information from a credit and/or debt card and/or print receipts corresponding to financial transactions. In embodiments, a card reader 895 may authentication information and financial information from a credit and/or debit card (off of a magnetic strip) and may communicate and/or transfer this information to the SMARTSHADE software application (e.g., utilizing a processor and/or controller) to include as part of the financial transaction request. In embodiments, a user of a third party POS and/or payment mobile device payment system (e.g., Google Wallet and/or Apple Pay) may pass information from the payment application to the SMARTSHADE payment system via an API, or through communications after confirmation with a NFC sensor 891 and/or a processor and/or controller 820.

Figure 9:
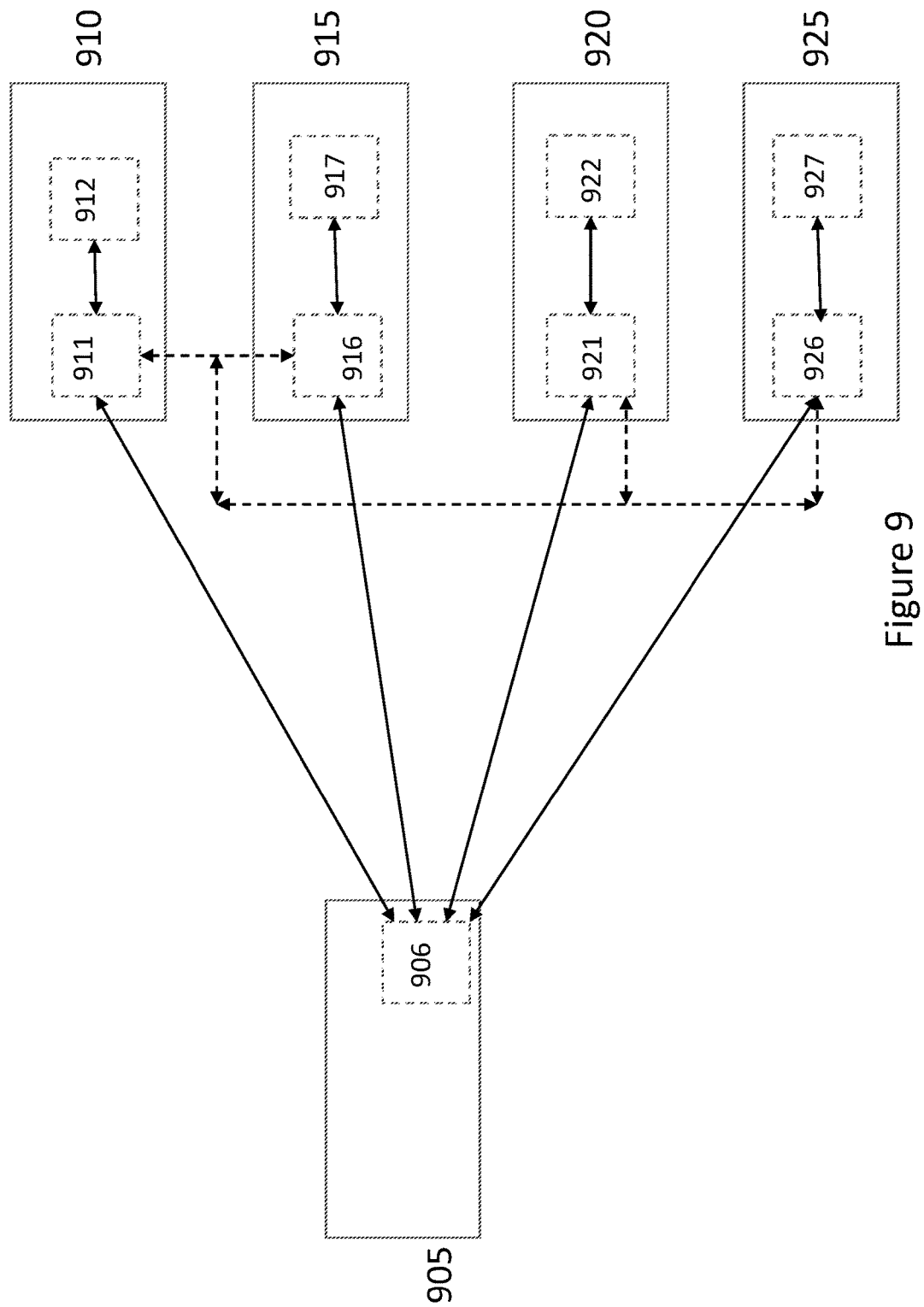
FIG. 9 illustrates a mobile computing device controlling operation of one or more modular umbrella systems according to embodiments.

FIG. 9 illustrates a mobile computing device controlling operation of one or more modular umbrella systems according to embodiments. FIG. 9 illustrates a mobile computing device 905 communicating with one or more of a plurality of modular umbrella systems 910, 915, 920 and/or 925. In embodiments, modular umbrella systems may comprise wireless transceivers 911, 916, 921 and/or 926 for communicating with other modular umbrella systems 910, 915, 920 and/or 925 and/or a mobile computing device 905. In embodiments, one or more modular umbrella systems 815 820 may comprise integrated computing devices 817 and 822. In embodiments, wireless transceivers 906, 911, 916, 921, and/or 926 may operate according any one or more of a plurality of personal area network, local area network, or other wireless and/or wired communication protocols, such as Bluetooth, Near-Field Communication (NFC) protocols, Zigbee, WiFi, 802.11, and including cellular wireless protocols such as GSM, CDMA, LTE and/or EDGE. In embodiments, computer-readable instructions may be stored on memory of a mobile computing device and executed by a processor to communicate with and/or control operations of one or more modular umbrella systems 910, 915, 920 or 925. In embodiments, modular umbrella systems 910, 915, 920 or 925 may have computer readable instructions stored in a memory of an integrated computing device 912, 917, 922 or 927 or other memory and executable by a processor of the integrated computing device 912, 917, 922 or 927, which may control operations of the modular umbrella system 910, 915, 920 or 925 where the computer-readable instructions are installed. In other words, part of software may be resident on a mobile computing device 905 and part of the software may be resident on one or more modular umbrella systems 910, 915, 920 or 925. In embodiments, computer-readable instructions executed by a processor of the mobile computing device 905 may communicate commands and/or instructions via a wireless transceiver 906 to one or more modular umbrella systems 910, 915, 920 or 925 via the modular umbrella system's wireless transceivers 911, 916, 921 or 926. For example, a mobile computing device 905 may communicate a command and/or message to turn on LED lights of one or more modular umbrella systems 910, 915, 920 or 925; to activate one or more motor assemblies (e.g., azimuth, elevation and/or deployment motors), and/or to obtain sensor readings from one or more modular umbrella systems 910, 915, 920 or 925. In embodiments, a mobile computing device 905 may communicate and/or stream audio, images, and/or videos (via a wireless transceiver 906) to one or more modular umbrella systems 910, 915, 920 or 925 via their wireless transceivers 911, 916, 921 or 926 and utilizing one or more integrated computing devices 912, 917, 922 or 927. In embodiments, one or more integrated computing devices 912, 917, 922 or 927 may receive communicated audio, video and/or images and may communicate and/or stream the audio, video, images to audio/video transceivers and/or onto a sound reproduction devices such as speakers and/or to video displays and/or monitors on one or more modular umbrella systems 910, 915, 920 or 925.

In embodiments, a mobile computing device 905 may communicate commands, instructions and/or messages (or videos, images, and/or sounds) via a wireless transceiver 906 to a first modular umbrella system's 910 wireless transceiver 911. In embodiments, commands, instructions and/or messages (or videos, images, and/or sounds) may be communicated to an integrated computing device 912 and/or commands, instructions and/or messages (or videos, images, and/or sounds) may be transmitted from the wireless transceiver 911 of a first modular umbrella system 910 to a second modular umbrella system 915 via a wireless transceiver 912. In embodiments, communication of commands, instructions and/or messages (or videos, images, and/or sounds) may continue to one or more modular umbrella systems (e.g., 915, 920 and/or 925) via respective wireless transceivers 916, 921 or 926.

In embodiments, a mobile computing device 905 may communicate (via a wireless transceiver 906) instructions, messages, and/or audio/video/images to a plurality of modular umbrella systems 910, 915, 920 or 925 (via respective wireless transceivers 911, 916, 921 or 926) so that each of the plurality of modular umbrella systems may receive the same instructions, messages, and/or audio/video/images at approximately a same and/or close to same time. In embodiments, a mobile computing device 905 may communicate and/or transfer (via a wireless transceiver 906) different commands instructions, messages, and/or audio/video/images to a plurality of modular umbrella systems 910, 915, 920 or 925 via their respective wireless transceivers 911, 916, 921 or 926. For example, a mobile computing device 905 may communicate one digital music file to a first modular umbrella system 910, a second music file to a second modular umbrella system 915 and a third music file to a third modular umbrella system 920. Similarly, a mobile computing device may transmit commands to move an azimuth motor of a plurality of modular umbrella systems 910 and 915 and/or lights of a different plurality of modular umbrella systems 920 or 926 In another example, a mobile computing device 905 may generate and/or communicate one or more commands (e.g., the same commands to one or more of the plurality of modular umbrella systems 910, 915, 920 or 925) and each of the plurality of modular umbrella systems may receive the command and/or message and act in a similar manner. In embodiments, the mobile computing device 905 may broadcast the command and/or message to each of the plurality of modular umbrella systems 910, 915, 920 or 925 simultaneously and/or almost at the same time. In embodiments, a mobile computing device 905 may communicate the message and/or command to a first modular umbrella system 910 in a plurality of modular umbrella systems, which in turn may communicate the message to a second modular umbrella system 915, which in turn may communicate the message and/or command to a third modular umbrella system 920, and so on.

In embodiments, a mobile computing device 905, executing, on a processor, computer-readable instructions stored in its memory (e.g., SMARTSHADE software), may generate one or more commands for one modular umbrella system 910; one or more commands for a second modular umbrella system 915; and/or one or more commands for a third modular umbrella system 920. In other words, a mobile computing device 905 may communicate different commands to each umbrellas. In embodiments, different commands and/or messages may be communicated to all of the plurality of umbrellas 910, 915, 920, or 925 (e.g., broadcast). In this illustrative embodiment, an identifier may be utilized to identify which modular umbrella system may receive which command and/or message). In embodiments, a mobile computing device 905 may communicate a command and/or message only to a modular umbrella system that is to receive the command and/or message and perform actions based on the command and/or message. In embodiments, for example, a mobile computing device 905 may generate instructions, commands and/or messages to a) turn on lights on a first modular umbrella system 910, b) rotate an azimuth motor of a second modular umbrella system 915 and/or c) extend arm support assemblies to a third modular umbrella system 920. In embodiments, mobile computing devices 905 may communicate instructions, commands and/or messages simultaneously and/or serially to a plurality of modular umbrella systems 910, 915, 920 and/or 925. In embodiments, wireless transceivers 906, 911, 916, 921 and/or 926 may operate according to a WiFi protocol and/or any of the 802.11 wireless communication technology or protocols. In embodiments, wireless transceivers 906, 911, 916, 921 and/or 926 may operate according to personal area network protocols and/or technologies such as infrared, ZigBee, Bluetooth and ultrawideband, or UWB protocols. In embodiments, transceivers 906, 911, 916, 921 and/or 926 may operate according to cellular wireless communication protocols such as GSM, CDMA, LTE, and/or EDGE.

Figure 10:
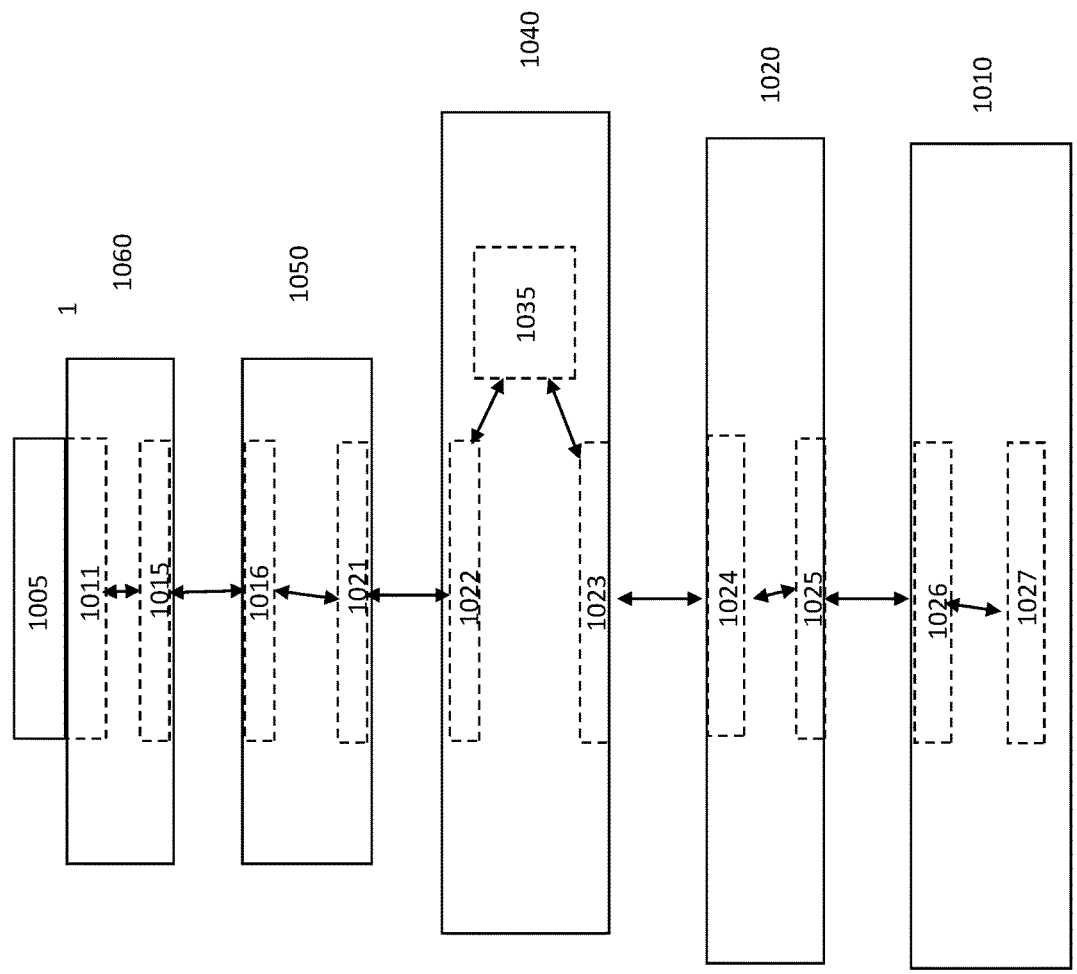
FIG. 10 illustrates a block diagram of a modular umbrella system with induction and/or wireless charging to provide power to components and assemblies according to embodiments.

FIG. 10 illustrates a block diagram of a modular umbrella system with induction and/or wireless charging to provide power to components and assemblies according to embodiments. In embodiments, alternating current may be introduced, connected and/or coupled in a wire loop generated an alternating magnetic field which in turn induced an alternating current in a nearby secondary coil. By attaching a load and/or devices to a secondary coil, the induced AC current could be made to do useful work (for example, charge a battery and/or provide power for other components in a system or device (e.g., a modular umbrella shading system). In embodiments, solar panel cells and/or arrays 1005 may generate electrical power from sunlight and transfer electrical power to a power converter 1011. In embodiments, a power converter 1011 may be coupled and/or connected to an expansion module primary coil 1015 (or induction loop). In embodiments, an expansion module primary coil 1015 may be magnetically coupled to an extension assembly secondary coil 1016 in order to transfer power (e.g., voltage and/or current) to an extension assembly secondary coil 1016. In embodiments, an extension assembly coil (and/or induction loop) may be magnetically coupled to a core assembly coil 1022 (and/or induction loop) and may transfer power (e.g., voltage and/or current) to a core assembly coil 1022) to power components in, for example, a core assembly 1040. In embodiments, a core assembly coil 1022 may be connected to a power source 1035 (e.g., a rechargeable battery 1035). In embodiments, a rechargeable battery 1035 may provide power (e.g., voltage and/or current) to components, assemblies and/or systems of a core assembly 1040 of a modular umbrella system. In embodiments, a rechargeable battery 1035 may be coupled and/or connected to a core assembly coil 1023 (or induction loop) and may transfer power (e.g., voltage and/or current) to a core assembly coil 1023. In embodiments, a core assembly coil 1023 (and/or induction loop) may be magnetically coupled to a first extension module first coil 1024 (and/or induction loop) and transfer power to a first extension module 1020. In embodiments, a first extension module first coil 1024 may be coupled and/or connected to a first extension module second coil 1025 and transfer power (e.g., voltage and/or current) to a base assembly 1010 (e.g, a base assembly coil 1026 or induction loop) and may transfer power to a base assembly coil 1026. In embodiments, a base assembly coil 1026 may be coupled and/or connected to a base battery or power source 1027. In embodiments, power transfer efficiency may be approximately 85 to 95% with minimal power loss. In embodiments, a base induction loop 1026 may be electrically coupled to a rechargeable battery 1027. In embodiments, power that was originally generated by solar cells which is not utilized by components, assemblies, or sensors of a modular umbrella system may be transferred to and stored in one or a plurality of rechargeable batteries 1035 and/or 1027. When solar cells are not providing enough power to operate components, assemblies and/or sensors, power from a rechargeable battery 1035 and/or 1027 may be utilized. In embodiments, for example, power may be transferred from the rechargeable battery 1027 to the base induction loop 1026 to a core induction loop 1023 (via coils and/or induction loops in a first extension assembly if a first extension assembly is utilized) and to a power source 1035, where power (e.g., voltage and/or current) is provided to components, assemblies and/or sensors that need power. In embodiments, for example, where two motors are being utilized at the same time and/or an integrated computing device is communicating video to an external computer server via a wireless transceiver, additional power may be needed because solar panels 1005 may not supply all of the current and/or voltage, a rechargeable battery 1035 and/or 1027 may provide the additional necessary power.

In embodiments, wireless charging power transfer between modules and assemblies may take place utilizing induction loop technology as described above. In embodiments, wireless charging power transfer between modules and assemblies may transfer power between coils operating at resonant or close to resonant frequencies, which may be determined by the coils' distributed capacitance, resistance and inductance. In embodiments, an oscillating magnetic field generated by the primary coil induces a current in the secondary coil but it takes advantage of the strong coupling that occurs between resonant coils (e.g., coils operated at a same resonant frequency—even when a primary coil and a secondary coil may be separated by tens of centimeters. In embodiments, energy from a primary coil "tunnels" from a primary coil to a secondary coil instead of spreading omnidirectionally from the primary coil. In embodiments, although energy may still attenuates to some degree with distance, the primary source of attenuation is the Q factor (gain bandwidth) of the coils. In addition, with resonant couple, energy transfer is not reliant on the coils being in the same orientation (providing that a secondary coil presents a large enough cross section to a primary coil so that in each cycle a secondary coil absorbs more energy than is lost by the primary). In embodiments, a further advantage of the technology is its ability to transfer power between a single primary coil and multiple secondary coils. In embodiments, where a modular umbrella system is utilizing resonant energy transfer, primary coils in one module and/or assembly may be placed at a farther distance from secondary coils in another module or assembly as compared to inductive coupling. Resonant coupling still has the benefit of providing power without utilizing wires and therefore freeing up more space. In addition, more space at connection points may be freed up if resonant coupling or energy transfer is utilized due to resonant energy transfer being able to operate at larger distances. In addition, a core assembly, which comprises many components and/or assemblies benefits from resonant energy transfer's ability to have one primary coil and a number of secondary coils. For example, one secondary coil may provide power for one motor assembly and another secondary coil may provide power for another motor assembly. Resonant wireless charging addresses the main drawback of inductive wireless charging; the requirement to closely couple the coils which demands precise alignment from the user.

In embodiments, a rechargeable battery may be installed and/or resident in a base assembly or module 110. In embodiments, a rechargeable battery in a base assembly or module 110 may generate power to provide voltage and/or current to motors, printed circuit boards, assemblies, components and/or an integrated computing device in a modular umbrella system. In other words, in embodiments, a rechargeable battery in a base assembly 110 may provide power for a majority of components, assemblies, devices and/or motors in a modular umbrella system 100. In embodiments, a base assembly 110 may comprise one or more rechargeable batteries. In embodiments, a rechargeable battery in a base assembly 110 may utilize Lithium-based battery technology, such is Lithium-Ion or Nickel Metal Hydride (NiMH) rechargeable batteries. In embodiments, a weight and/or mass or a rechargeable battery in a base assembly 110 may also provide stability for a modular umbrella system 100. In embodiments, rechargeable batteries may be placed in a uniform manner in a base assembly 110 in order to provide an even distribution of weight. For example, one rechargeable battery may be placed on a left side of a base assembly 110 and a second rechargeable battery may be placed in a symmetrical position on a right side of a base assembly 110. In embodiments, utilization of one or more rechargeable batteries in a base assembly 110 may allow for additional weight (or weights) to be removed from a base assembly 110.

In embodiments, a modular umbrella system may comprise a wind sensor 194 and a surface vent. In embodiments, an upper assembly 140 or a lower assembly 142 of a core assembly or module 130 may be a location for a wind sensor 191 and/or a surface vent. In embodiments, a wind sensor 191 may be located in an interior position of an upper assembly and/or a lower assembly. In embodiments, a surface and/or skin vent may be built into and/or integrated into an outer surface and/or skin of an upper assembly 140 and/or lower assembly 142 and may be positioned as to allow air flow into a wind sensor 191. In this embodiment, other external factors around a modular umbrella system 100 may not be an issue (e.g., rain or snow or smoke) since a wind sensor 191 may be protected from environmental factors. In addition, interior positioning of a wind sensor 191 may keep it being broken and/or hit from objects and/or individuals around a modular umbrella system 100.

In embodiments, a core assembly or module 130 may comprise a DC power charging port 192. In embodiments, a DC charging port 192 may comprise a USB charging port. In embodiments, a DC charging port may be positioned at a 45 degree angle with respect to an outer surface of a core module or assembly 130 (or a first extension module or assembly 120, a base module or assembly 110, a second extension module or assembly 150). In embodiments, a DC charging port 192 may be positioned at between a 10-80 degree angle with respect to an outer surface of a core module assembly 130 in order to protect a DC charging port 192 from rain, snow, moisture and/or other environmental conditions. In other words, by positioning a DC charging port 192 at an angle, moisture and/or other environmental conditions may not enter a DC charging port 192. In embodiments, a plastic plug and/or covering may cover and/or protect a DC charging port 192 and provide further protection from environmental conditions. In embodiments, more than one charging ports 192 may be installed on a modular umbrella system 100.

In embodiments, a modular umbrella system 100 may transfer video, images and/or audio to a mobile communication device. In embodiments, a modular umbrella system 100 may comprise a processor in an integrated computing device 136, a cellular transceiver 195, a local area network wireless or WiFi transceiver 196, a personal area network (e.g., Bluetooth, Zigbee) transceiver 197, a microphone, and/or a camera 137. In embodiments, a camera 137 may capture images, video, and/or audio from an environment surrounding a modular umbrella system 100. In embodiments, a processor may store captured images in a memory of an integrated computing device 136 (e.g., a memory may be a volatile memory and/or non-volatile memory) and may transfer and/or communicate captured images, video and/or audio to a cellular transceiver 195. In embodiments, a cellular transceiver 195 in a modular umbrella system may transfer and/or communicate received images, video and/or audio to a cellular transceiver in one or more mobile computing devices via a cellular communication network. In embodiments, the captured images, video and/or audio may not be transferred via a local area network wireless (e.g., WiFi, 802.11), or via a personal area network (e.g., Bluetooth) and thus may not be limited to only being transmitted to devices within certain geographic areas or distance limitations. This allow remote monitoring of an area surrounding a modular umbrella system 100 like from areas in different building, different cities or other remote areas. In embodiments, images, video and/or audio may be transferred from a cellular transceiver of a mobile device to a display and/or speaker of a mobile computing device. In embodiments, images, video and/or audio may be displayed within a software application being executed by a processor of a mobile computing device. In these embodiments, the captured video, audio and images may not pass through and/or communicated through a packet switched network (e.g., the Internet).

Figure 11:
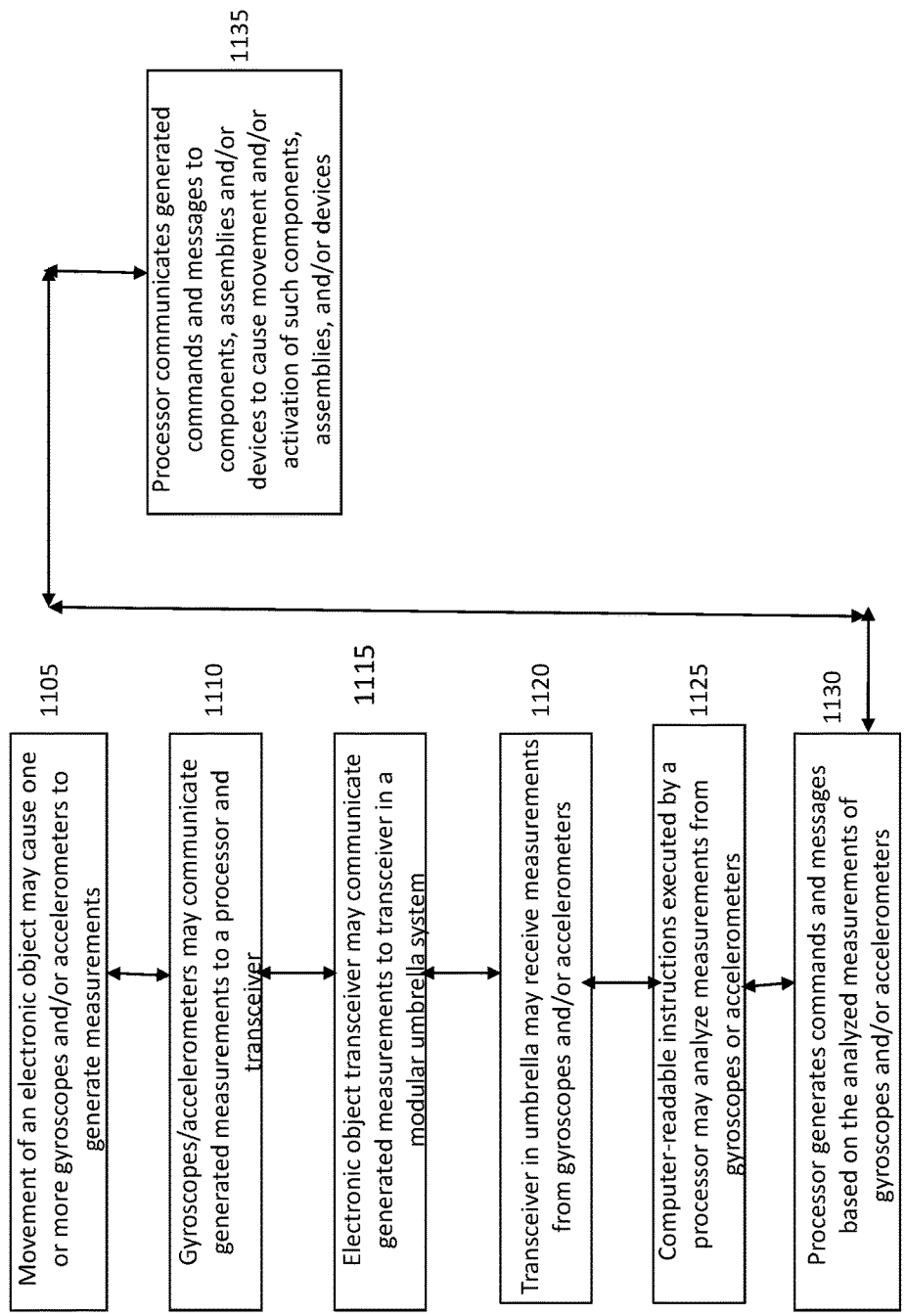
FIG. 11 illustrates a flowchart of a process of controlling a modular umbrella system by an object accordingly to embodiments.

FIG. 11 illustrates a flowchart of a process of controlling a modular umbrella system by an object accordingly to embodiments. In embodiments, a user may be able to move a mobile computing device and a modular umbrella system may move in a same and/or similar fashion. For example, in embodiments, a user may move a mobile computing device to in a left direction at a 45 degree angle and an upper core assembly may move approximately 45 degrees with respect to a lower upper assembly (e.g., utilizing an elevation motor assembly). As another illustrative example, a user may spin and/or rotate a mobile phone approximately 180 degrees, and a core assembly module 130 and/or a first extension module 120 may rotate 180 degrees about a vertical axis with respect to a base assembly. In embodiments, rather than utilizing a mobile computing device, a user may utilize another electronic object to control operation of modular umbrella system by movement of the electronic device. In embodiments, an electronic object may be shaped like a hockey puck, a console, a square, a remote control, or similarly shaped device. In embodiments, a user may move an electronic object in a direction and a modular umbrella system may respond by moving in a same and/or similar direction. In embodiments, for example, a user may move an hockey puck shaped electronic object in an upward swooping direction, and a modular umbrella may respond by deploying arm/spoke support assemblies from a closed to an open position which results in arms/spokes deploying on a modular umbrella system. In embodiments, for example, a user may hit or knock an electronic object twice on a surface, and this movement may result in lighting assemblies being activated and turning on in a modular umbrella system.

In embodiments, a mobile computing device and/or an electronic object may comprise one or more gyroscopes and/or accelerometers, one or more processors or controllers, and a transceiver. In embodiments, a transceiver may be a cellular transceiver, a personal area network (PAN) transceiver (e.g., Bluetooth, Zigbee) and/or a local area network wireless (e.g., WiFi and/or 802.11) transceiver. In embodiments, movement of a mobile computing device and/or electronic object may cause one or more gyroscopes and/or accelerometers to generate 1105 measurements associated with and/or corresponding to the movement of the mobile computing device and/or electronic object. In embodiments, one or more gyroscopes or accelerometers may communicate 1110 generated measurements to a processor which may communicate and transfer the generated measurements associated with a mobile computing device's or an electronic device's movement to a transceiver. In embodiments, a mobile computing device and/or electronic object's transceiver may communicate 1115 generated measurements to a corresponding transceiver in a modular umbrella system. In embodiments, for example, a PAN (e.g., Bluetooth) transceiver in a mobile computing device may communicate with a PAN (e.g., Bluetooth) transceiver in a modular umbrella system. In embodiments, a transceiver in a modular umbrella system may receive 1120 generated measurements from one or more gyroscopes and/or accelerometers in a mobile computing device or electronic device and may communicate generated measurements to a processor and/or controller of a modular umbrella system. In embodiments, computer-readable instructions stored in a memory may be executed by a processor and/or controller and may analyze 1125 received generated measurements from the one or more gyroscopes or accelerometers of, for example, a mobile computing device. In embodiments, computer-readable instructions stored in a memory may be executed by a processor or controller and may generate 1130 commands, messages, signals and/or instructions based on the analyzed received measurements of one or more gyroscopes and/or accelerometers of a mobile computing device and/or electronic object. In embodiments, for example, commands and/or messages may be sent to components, assemblies and/or devices to cause movement of such. In embodiments, a processor and/or controller may communicate 1135 generated commands, messages, signals and/or instructions to components, assemblies and/or devices to cause movement and/or activation of such components, assemblies, and/or devices. For example, if a gyroscope and/or accelerometer generates measurements corresponding to a rotation movement, a processor and/or controller in a modular umbrella system may communicate commands and/or messages to an azimuth motor assembly to rotate a first extension assembly 120 and/or core assembly 130 with respect to a base assembly 110. While the above-described illustration utilizes a PAN transceiver, a WiFi and/or cellular transceiver may also be used to establish communications between a mobile computing device/electronic device and a modular umbrella system. Utilizing an electronic object and/or device may be helpful in outdoor environments where liquids, lotions and/or other substances may be present. In such embodiments, such liquids, lotions and/or substances may spill onto and cause a malfunction of a mobile computing device, wherein an electronic object and/or device may be outfitted or covered by a more durable surface material that may resist environmental conditions (e.g., rain, wind, snow, smoke) as well as liquids, lotions, oils and/or other substances. Thus, a user that has just applied sunscreen and/or suntan oil may be able to utilize an electronic object and/or device to control operation of a modular umbrella system without damaging an electronic device.

Figure 12:
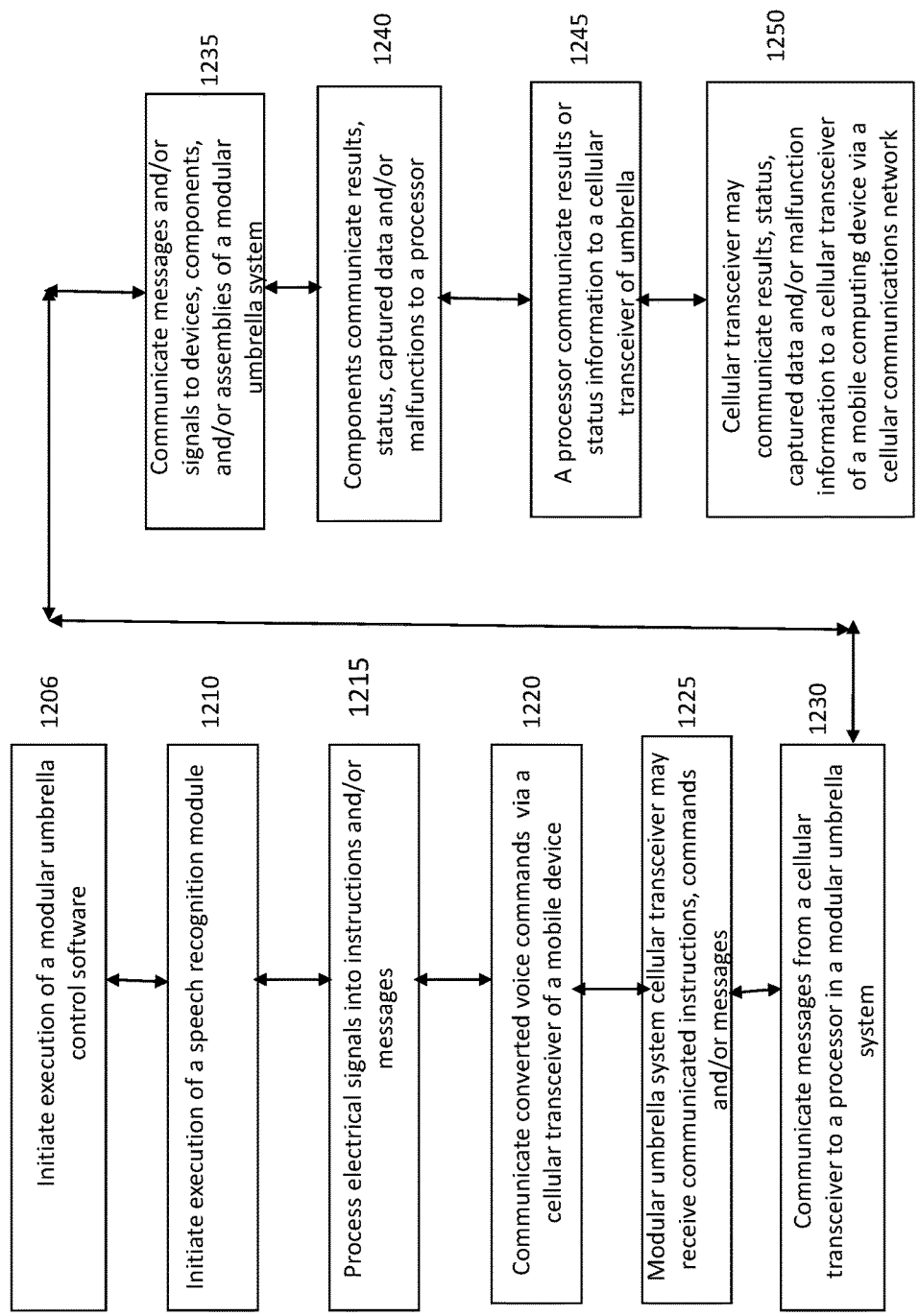
FIG. 12 illustrates remote operation of a modular umbrella system according to embodiments.

In embodiments, a user may be able to operate and/or provide commands to a modular umbrella system 100 from a remote location or another area separate from an environment in which a modular umbrella system may be installed. FIG. 12 illustrates remote operation of a modular umbrella system according to embodiments. In embodiments, a user may initiate execution 1205 of a modular umbrella control software (e.g., computer-readable instructions executable by a processor of a mobile computing device). In embodiments, a user may initiate execution 1210 of a speech recognition module, program or subroutine, in a modular umbrella control software. In embodiments, a user may speak and a mobile computing device microphone may receive voice command, convert voice commands into electrical signals (analog and/or digital), and a voice recognition module may process 1215 the electrical signals into instructions, commands, and/or messages. In embodiments, a voice recognition module may be a third party voice recognition engine running on a mobile computing device (e.g., Dragon voice recognition engine, etc.), a third party voice recognition module running on a separate physical computing device (e.g., Amazon Alexa and Echo), or a voice recognition module running as part of a shading object control application software. In embodiments, for example, commands may be rotate umbrella, open up umbrella spokes, turn on camera, communication video and/or images from camera, and/or activate solar panel cells, etc. In embodiments, a mobile computing device (and/or modular umbrella control software executing on a processor) may communicate 1220 converted voice instructions, commands and/or messages via a cellular transceiver of a mobile device to a cellular transceiver of a modular umbrella system via a cellular communications network. In embodiments, a modular umbrella system cellular transceiver may receive 1225 communicated instructions, commands and/or messages via a cellular communications network. In embodiments, received instructions, commands and/or messages may be communicated 1230 from a cellular transceiver to a processor in a modular umbrella system. In embodiments, a modular umbrella system processor may communicate 1235 commands, instructions, messages and/or signals to devices, components, and/or assemblies of a modular umbrella system (e.g., a camera, an azimuth motor assembly, a solar cell) to perform actions requested in the received voice commands. In embodiments, commands, instructions, messages and/or signals may be communicated through a processor in a motion control board and/or a processor in an integrated computing device. In embodiments, devices, components, and/or assemblies of modular umbrella system may communicate 1240 results, status, captured data and/or malfunctions to a processor of a modular umbrella system. In embodiments, a processor of a modular umbrella system may communicate 1245 results, status, captured data and/or malfunction information to a cellular transceiver of a modular umbrella system. In embodiments, a cellular transceiver may communicate 1250 results, status, captured data and/or malfunction information to a cellular transceiver of a mobile computing device via a cellular communications network. In embodiments, received results, status, captured data and/or malfunction information may be communicated to a mobile application software application. In embodiments, this allows remote operation of a modular umbrella system via a cellular network and cellular communications. In embodiments, a cellular communications network may operate utilizing GSM, CDMA, LTE and/or EDGE wireless network protocols. This allows a user to be in a completely different geographic location and still be able to control operations of a modular umbrella system. A user may be able to not only control operation but also to capture environmental information from a modular umbrella system (e.g., sensors, cameras, etc.) and receive indications of such captured information.

In embodiments, a base assembly 110 may comprise a beach base attachment. In embodiments, a beach base attachment may comprise an activation assembly, a motor assembly, a gearing assembly and a shaft assembly. In embodiments, a user may initiate an activation assembly. In embodiments, an activation assembly may be a button and/or a switch. In embodiments, an activation assembly may turn on and/or activate a motor assembly, which may cause a shaft to rotate and/or turn. In embodiments, a shaft's rotation may cause a gearing assembly to rotate and/or turn. In embodiments, a gearing assembly may rotate one or more shafts and/or prongs and cause one or more shafts and/or prongs to burrow and/or drive deeper into the sand in order to provide stability to a modular umbrella system 100. In embodiments, a base assembly 110 may comprise a grass or ground attachment. In embodiments, a grass or ground attachment or assembly may comprise an activation assembly, a motor assembly, a gearing assembly and/or a stake assembly. In embodiments, a user may initiate or execute an activation assembly. In embodiments, an activation assembly may be a button and/or a switch. In embodiments, an activation assembly may turn on and/or activate a motor assembly, which may cause a shaft to rotate and/or turn. In embodiments, a shaft's rotation may cause a gearing assembly to rotate and/or turn. In embodiments, a gearing assembly may rotate one or more stakes and/or prongs and cause one or more stakes and/or prongs to burrow into a ground surface. In embodiments, burrowing into a ground surface may provide greater stability for a base assembly 110. Prior art umbrella systems may utilize weights, a heavier base and/or a wider base to provide stability. However, the apparatus described herein may adjust to density of a ground surface and/or sand and dig deep enough to provide necessary stability. In embodiments, a grass or ground attachment (or beach attachment) may be adjustable depending on necessary depth needed to provide stability for a modular umbrella system.

Figure 14:
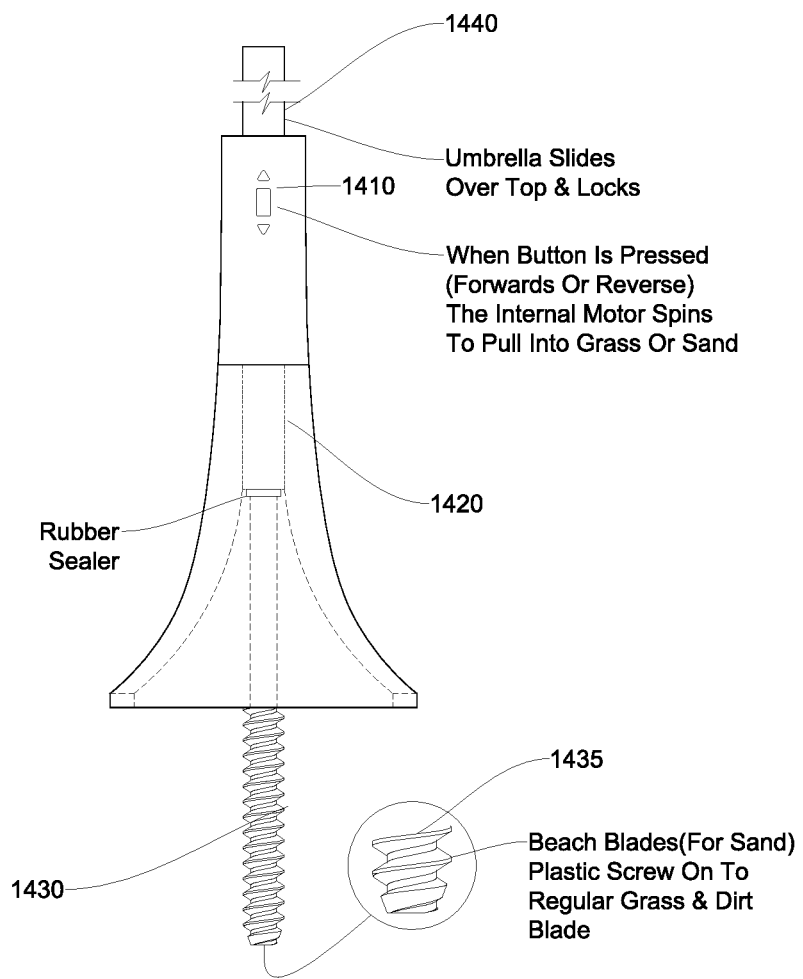
FIG. 14 illustrates a base surface attachment according to embodiments.

FIG. 14 illustrates a base surface attachment according to embodiments. In embodiments, a base attachment 1400 comprises a power activation button 1410, a motor 1420 and one or more blades 1430. In embodiments, a first extension assembly or module 1440 or core assembly or module (not shown) may be inserted and/or placed into an opening of a base surface attachment 1400 and may be placed in a locked position. In embodiments, when a power activation button 1410 is pressed, an individual motor 1420 may be activated and operate in forward and/or reverse. In embodiments, an individual motor 1420 may drive and/or spin blades 1430 to pull into grass and/or a beach (or another ground surface). In embodiments, additional blades 1435 may be screwed into blades 1430 to provide additional support for the base attachment 1400 of a modular umbrella system 100. In embodiments, additional blades 1435 may be a plastic blade (e.g., or screw) that is attached and/or corrected to a bottom portion of a blade 1430 to be utilized to dig into or burrow into a different type for surface (e.g., sand or loose dirt as opposed to grass and/or compact dirt). In embodiments, blades 1430 and/or additional blades 1435 may be comprised of a metal material, a composite materials and/or a plastic material.

In embodiments, a modular umbrella system 100 may comprise an interior umbrella security system. In embodiments, a module or assembly of a modular umbrella system 100 may comprise an interior umbrella security system. In embodiments, for example, a core module or assembly 140 may comprise an interior umbrella security system. In other embodiments, a base module or assembly 110 and/or an expansion sensor module 160 may comprise an interior security system. In embodiments, an interior security system may comprise one or more sensors, one or more cameras and one or more lighting assemblies. In embodiments, if an unauthorized user or operator attempts to open one or more of the umbrella modules (e.g., a base module, a core module and/or an expansion sensor module) by removing a skin and/or housing, a sensor attached to a skin or housing may be tripped and/or activated, and may communicate a signal, command and/or message to a controller and/or processor in a modular umbrella system 100. In embodiments, a controller and/or processor in a modular umbrella system 100 may communicate a command and/or message to a camera to activate a camera. In embodiments, a camera may capture images and/or video and communicate captured images and video to a memory of an integrated computing device in a modular umbrella system or to a remote cloud-based server. In embodiments, a processor and/or controller may communicate a command and/or message to one or more lighting assemblies to place lighting assemblies in an alarm mode. In embodiments, lighting assemblies may begin to blink or display a different color if in alarm mode (indicating that a skin assembly and/or housing has been breached. In embodiments, this allows a manufacturer to void a warranty if unauthorized access occurs. In addition, in embodiments, a user and/or operator may utilize this feature to determine if an individual or company has accessed an interior of a module umbrella system and sabotaged the umbrella. In addition, a manufacturer may also be able, if a camera is utilized, to store information regarding all individuals who have breached an interior of a modular umbrella system.

Figure 15:
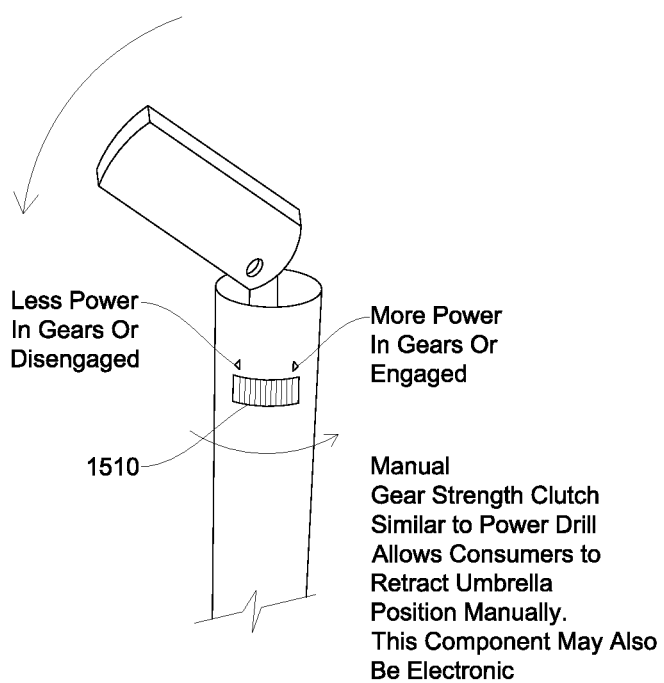
FIG. 15 illustrates a clutch system according to embodiments.

In embodiments, a modular umbrella system 100 may comprise a clutch system for manually operating a modular umbrella system. FIG. 15 illustrates a clutch system according to embodiments. In embodiments, a user and/or operator may desire to manually position a modular umbrella system without utilizing any of the motors (e.g., azimuth motor, elevation motor and/or extension/expansion motor). In embodiments, a user and/or operator may desire to manually position an azimuth location but still allow motors to move a modular umbrella system to an elevation position and/or an expansion/extension position (e.g., in other words, utilize manual movement for one or more positions and motor positioning for other positions and/or elevations). In embodiments, a button may disable utilization of one or more motor assemblies (e.g., or a selection of an item in modular umbrella control software may disable or deactivate motor assemblies in a modular umbrella system). In embodiments where one or more motor assemblies are disabled, a clutch 1500 may be activated and/or utilized to cause a shaft to move, for example, an cause a core module assembly 130 and/or first extension assembly 120 to rotate with regard to a base assembly 110. Similarly, a clutch may be activated and/or utilized to cause a shaft to move an arm/spoke extension support assembly (and thus attached arms and/or spokes from a closed to an open position (or vice versa). FIG. 15 illustrates a clutch assembly according to embodiments. FIG. 15 illustrates a lever or switch 1510 utilized to engage a clutch to manually mechanically adjust, for example, a position of a modular umbrella system. In embodiments, a clutch may electronically adjust a position of a modular umbrella system. For example, in embodiments, a lever or switch 1510 may manually retract arm support assemblies of an expansion sensor module or assembly. In embodiments, for example, a lever or switch 1510 may manually move an upper support assembly 1515 to a rest position from an angled position with respect to a lower support assembly 1520. In embodiments, a lever or switch 1510 may allow multiple positions (e.g., not fully open or closed (e.g., less or more engaged) for different assemblies of a modular umbrella system.

In embodiments, a mobile computing device may be communicatively linked with one or more modular umbrella systems. In embodiments, mobile computing devices may be communicatively coupled to one or more modular umbrella systems directly (e.g., via a personal area network), via wireless local area network wireless communications (e.g., directly, or via access points, and/or via a cloud-based server utilizing WiFi or 802.11 communication protocols) and/or via cellular communication networks. In embodiments, personal area network wireless communication protocols may include Zigbee, Bluetooth, RC-5, SIRCS, RC-6, R-Step, NTC101, etc.).

FIG. 13 illustrates a block diagram of a modular umbrella system according to embodiments. In embodiments, as is illustrated in FIG. 13, a modular umbrella shading system 1300 may comprise a telemetry printed circuit board (PCB) comprising a processor 1305, a weather variable PCB comprising a processor 1310, a voice recognition PCB and/or engine 1315, a rechargeable battery 1320, and one or more solar panels and/or solar panel arrays 1325. In embodiments, a modular umbrella shading system 1300 may comprise a power tracking solar charger 1330, a power input or power source (e.g., AC adapter assembly) 1335, a lighting assembly 1370, an audio system 1375 and/or a computing device 1360. In embodiments, a modular umbrella shading system may include an obstacle detection module 1355, a motion sensor 1345, a proximity sensor 1340, a tilt sensor 1355, a personal area network communications module or transceiver 1365, a first motor controller and motor (azimuth motor and controller) 1380, a second motor controller and motor (elevation motor and controller) 1385, and a third motor controller and motor (an actuator motor and controller) 1390. In embodiments, a weather variable PCB 1310 may be coupled and/or connected to one or more air quality sensors 1311, UV radiation sensors 1312, a digital barometer sensor 1313, a temperature sensor 1314, a humidity sensor 1316, and/or a wind speed sensor 1317. In embodiments, a wind sensor 1317 may be a thermistor. In embodiments, a telemetry PCB 1305 may be coupled and/or connected to a GPS/GNSS sensor 1307 and/or a digital compass 1308. Although at times a modular umbrella shading system, shading object, intelligent umbrella and/or shading charging system may singularly be mentioned, the disclosure herein may be implemented in any of the above-mentioned devices and/or apparatus.

In embodiments, a modular umbrella shading system may comprise one or more printed circuit boards. Although a description may reference a specific printed circuit board, many of features or functions of a modular umbrella shading system may be implemented utilizing components mounted on a single, two or three circuit boards. In addition, one or more components may be mounted on printed circuit boards, which results in a large number of circuit boards within a modular umbrella shading system. In other words, a number of circuit boards may be utilized to provide features and/or functions of a shading object and/or umbrella although embodiments described herein may only describe a specific number. Although the term "circuit board" or "printed circuit board" is utilized, any electronic device allowing installation on and communicate with components may be utilized along with circuit board. As used in this specification, the terms "printed circuit board" and "PCB" are intended to refer generally to any structure used to mechanically support and electrically connect electronic components using conductive pathways, tracks, or signal traces etched from (e.g., copper) sheets laminated onto a non-conductive substrate. Synonyms for printed circuit boards include printed wiring boards and etched wiring boards.

In embodiments, a shading object, umbrella and/or shading charging system may comprise one or more printed circuit boards. In embodiments, a shading object or umbrella 1300 may comprise a movement control PCB 1395, a shading object computing device or computing device PCB 1360, a first motor PCB (azimuth control) 1380, a second motor PCB (elevation control) 1385, a third motor PCB (actuation/deployment control) 1390, a telemetry PCB (location and orientation data/information collection) 1305, and/or a weather variable PCB (environmental sensor data/information collection) 1310.

In embodiments, a telemetry PCB 1305 comprises a processor, a memory, a GPS receiver and/or transceiver and/or a compass (e.g. a digital) compass). The GPS receiver and/or compass provides location and orientation information and/or measurements which may be transferred to a memory utilizing a processor. In embodiments, a telemetry PCB processes and conditions the communicated information and/or measurements. In embodiments, a telemetry PCB 1305 communicates measurements and/or additional information (e.g., in some cases, measurements are conditioned and processed and in some cases, measurements are raw data) to a shading object movement control PCB 1395 which analyzes the received location and/or orientation information and measurements.

In embodiments, a weather variable PCB 1310 comprises a processor, a memory, an air quality sensor, a UV radiation sensor, a barometer, a temperature sensor, a humidity sensor, and/or a wind speed sensor. One or more of the listed sensors may generate environmental and/or weather measurements and/or information, which may be transferred to a memory utilizing a processor. In embodiments, a weather variable PCB 1310 processes and conditions information and measurements from the one ore more sensors. In embodiments, a weather variable PCB 1310 communicates received environmental and/or weather sensor measurements (e.g., in some cases conditioned and processed and in some cases raw data) to a shading object movement control PCB 1395 which analyzes the received location and/or orientation information and measurements.

In embodiments, a core assembly or module 130 may comprise an umbrella movement control PCB 1395, as well as an integrated computing device PCB 1360. In embodiments, a movement control PCB 1395 may also be located in a base assembly or module 110. In embodiments, other terms may be utilized in place of circuit board, such as printed circuit board, a flexible circuit board, and/or an integrated circuit. In embodiments, an umbrella movement control PCB 1395 may consume a low amount of power and may be referred to as a low-power PCB. In embodiments, this may prove to be a benefit as compared to prior-art umbrellas which utilized a large amount of power and thus needed to have power from a power source and could not be powered by an array of solar cells providing power to a solar power charger 1330. In embodiments, a solar array may provide enough provide power to power components on an umbrella movement control PCB 1395. In this case, for example, components and associated activities controlled by an umbrella movement circuit PCB 1395 may not consumer large amounts of power because these activities do not require continuous operation and may only receive information or measurements on a periodic basis. As an example, an intelligent shading object 1300 may not be rotating and/or tilting frequently. Thus, in embodiments, therefore, sensors providing these measurements (e.g., a tilt sensor or sunlight sensor), and a movement control PCB communicating these measurements may not need to be in an active state at all times, which results in significant power usage savings for a shading object and/or controller.

In embodiments, a motion control PCB 1395 may comprise a processor, a non-volatile memory, a volatile memory, and many other components described above and below. In embodiments, for example, computer-readable instructions may be fetched from a non-volatile memory, loaded into a volatile memory, and executed by a processor to perform actions assigned to, controlled and/or commanded a motion control PCB 1395. In embodiments, non-volatile memory may be flash memory, ASIC, ROMs, PROMs, EEPROMs, solid state memory, CD, DVD, persistent optical storage or magnetic storage media.

In embodiments, as a further example, modular umbrella shading system motors, e.g., a first motor (azimuth movement motor), a second motor (elevation movement motor), and/or a third motor (articulation or actuator movement motor) may not be utilized frequently, so there does not need to be a large amount of power utilized by these motors within a shading object. In embodiments, when motors and/or motor assemblies are operating, the motors may require 2 to 3 amps. If system is idle and for example, the shading computer is not operating, an intelligent shading object may only require 180 milliamps. If an audio system is operating, e.g., music is playing and the amplifier and speakers are being utilized, only 400-500 milliamps, In addition, motor controllers may not be utilized frequently since the motor controllers may not be driving and/or sending commands, instructions, and/or signals to motors frequently. Thus, a low-power movement control PCB 1395 may provide a shading object owner with power usage savings and efficiency.

In embodiments, readings and/or measurements from sensors may cause a movement control PCB 1395 to transmit commands, instructions, and/or signals to either a first motor control PCB 1380 (azimuth movement), a second motor control PCB 1385 (elevation movement), and/or a third motor control PCB 1390 (actuation movement), in order to cause specific movements of different assemblies of a modular umbrella shading system. For example, in embodiments, a GPS transceiver 1306 may receive GPS signals and provide GPS measurements (e.g., values representative of a longitude, latitude, and/or an altitude reading) to a movement control PCB 1395. In embodiments, a movement control PCB 1395 may analyze the GPS measurements and determine that a shading object, umbrella, and/or shading charging system should be moved to a specific elevation. In other words, in embodiments, a movement control PCB 1395 may utilize GPS generated measurements to direct a second motor assembly to move to a proper elevation. In embodiments, GPS measurements (coordinates and time) identify a proper elevation of the sun based on a geographic location. In embodiments after a core assembly of module 130 may be moved to a position identified by GPS measurements, arm/spoke support assemblies 163 may be extend and the arms and/or blades 164 may be fully deployed. In embodiments, a movement control PCB 1396 may communicate commands, instructions, and/or signals to a second motor control PCB 1385 to cause an upper core assembly 140 of a core assembly 130 to rotate or move approximately 45 degrees in a downward direction with respect to a lower core assembly 142 of the center support assembly. In embodiments, a movement control PCB 1395 may communicate commands, instructions, and/or signals to a third motor control PCB to fully extend arm/blade support assemblies 163 (e.g. articulating blades/assemblies) and also arms/blades 164.

In embodiments, a digital compass 1307 may generate a heading and/or orientation measurement and a telemetry PCB 1305 may communicate a heading and/or orientation measurement to a movement control PCB 1395. In embodiments, a movement control PCB 1395 may analyze a heading measurement and generate and/or communicate commands, instructions, and/or signals to a first control PCB 880 to rotate a first extension assembly 120 and a core assembly or module 130 to face or move the shading object towards a light source (e.g., a sun). In embodiments, digital compass measurements may be utilized as directional input for an azimuth (or first motor). In embodiments, a movement control PCB 1395 may calculate counts and/or limits for motors to properly orient an intelligent shading object based on GPS measurements and/or digital compass measurements. Continuing with this embodiment, a movement control PCB 1395 may generate and/or communicate commands, instructions, and/or signals to a third motor controller PCB 890 to cause arm support assemblies 163 to be extended or deployed along with arms/blades 164.

In embodiments, a wind speed sensor 1317 may generate measurements and a variable weather PCB 1310 may communicate measurements to a shading object movement control PCB 1395. In embodiments, a movement control PCB 1395 may analyze and/or compare communicated measurements to a threshold in order to determine if unsafe conditions are present. In embodiments, for example, if a wind speed threshold is reached or exceeded, identifying an unsafe condition, a movement control PCB 1395 may communicate commands, instructions, and/or signals to move shading object assemblies to a rest position. Continuing with this illustrative example, a movement control PCB 1395 may communicate commands or instructions or signals to a second movement control PCB to cause an upper core assembly 140 to move to an original position (e.g., at rest position), which may be where an upper core assembly 140 is a vertical extension of a lower assembly 142. In embodiments, a movement control PCB 1395 may communicate instructions, commands and/or signals to a third motor control PCB 1390 to move arm/spoke support assemblies 163 back into an upper assembly and/or retract arm/spoke support assemblies 163 into channels of an upper assembly 140. In embodiments, a movement control PCB 1395 may communicate commands, instructions and/or signals to a sound reproduction system 1375 and/or a display device to warn a user of unsafe wind conditions. Although the description above corresponds to a modular umbrella shading system of FIGS. 1 and 2, the description applies to similar components in the intelligent shading charging system, intelligent umbrellas, and/or shading objects.

In embodiments, a first motor control PCB 1380, a second motor control PCB 1385, a third motor control PCB 1390 and a movement control PCB 1395 may be connected to each other via wires and/or traces and instructions may, commands and/or signals may be communicated via wires and/or traces. In embodiments, the motor control PCBs 1380, 1385 and 1390 may communicate with a movement control PCB 895 via a personal area network communications protocol, e.g., Bluetooth. In embodiments, a weather variable PCB 1310 and/or a telemetry PCB 1305 may communicate with a movement control PCB 1395 via wires, traces, integrated circuits, and/or interfaces and communicate instructions, commands or signals. In embodiments, a weather variable PCB 1310 and a telemetry PCB 1305 may communicate with a movement control PCB 1395 via personal area network protocols (utilizing a PAN transceiver—e.g., a Bluetooth transceiver). In embodiments, motor control PCBs 1380 1385 1390 may communicate directly (either via wires or a wireless communication protocol) with a weather variable PCB 1310 and/or a telemetry PCB 1305 without utilizing a computing device 1360 and/or a movement control PCB 1395.

In embodiments, as described above, a modular umbrella shading system may comprise a computing device PCB (e.g., a single board computer or a system on a chip), which may comprise a computing device 1360 in a shading object, intelligent umbrella and/or shading charging system. In embodiments, a modular umbrella shading system may comprise a computing device 1360 which is not installed and/or mounted on a computing device PCB. In embodiments, a computing device 1360 and/or a computing device PCB may consume a larger amount of power (with respect to movement control PCB 1395) due to activities it is responsible for executing being performed more frequently and/or with a higher data throughput. In embodiments, an integrated computing device 1360 may be responsible for camera control, video and/image processing, external Wi-Fi communication, e.g., such as operating as a hot spot, as well as running various software applications associated with the modular umbrella shading system. The computing device 1360, because of operating and being responsible for more data intensive features and/or functions, may require more processing power due to extended operation and continuous data throughput. In embodiments, a computing device may be integrated into a core assembly or module 130. In embodiments, a computing device may be integrated into a base assembly or module 110. In embodiments, a computing device may be incorporated into an expansion sensor module or assembly 160.

Figure 16:
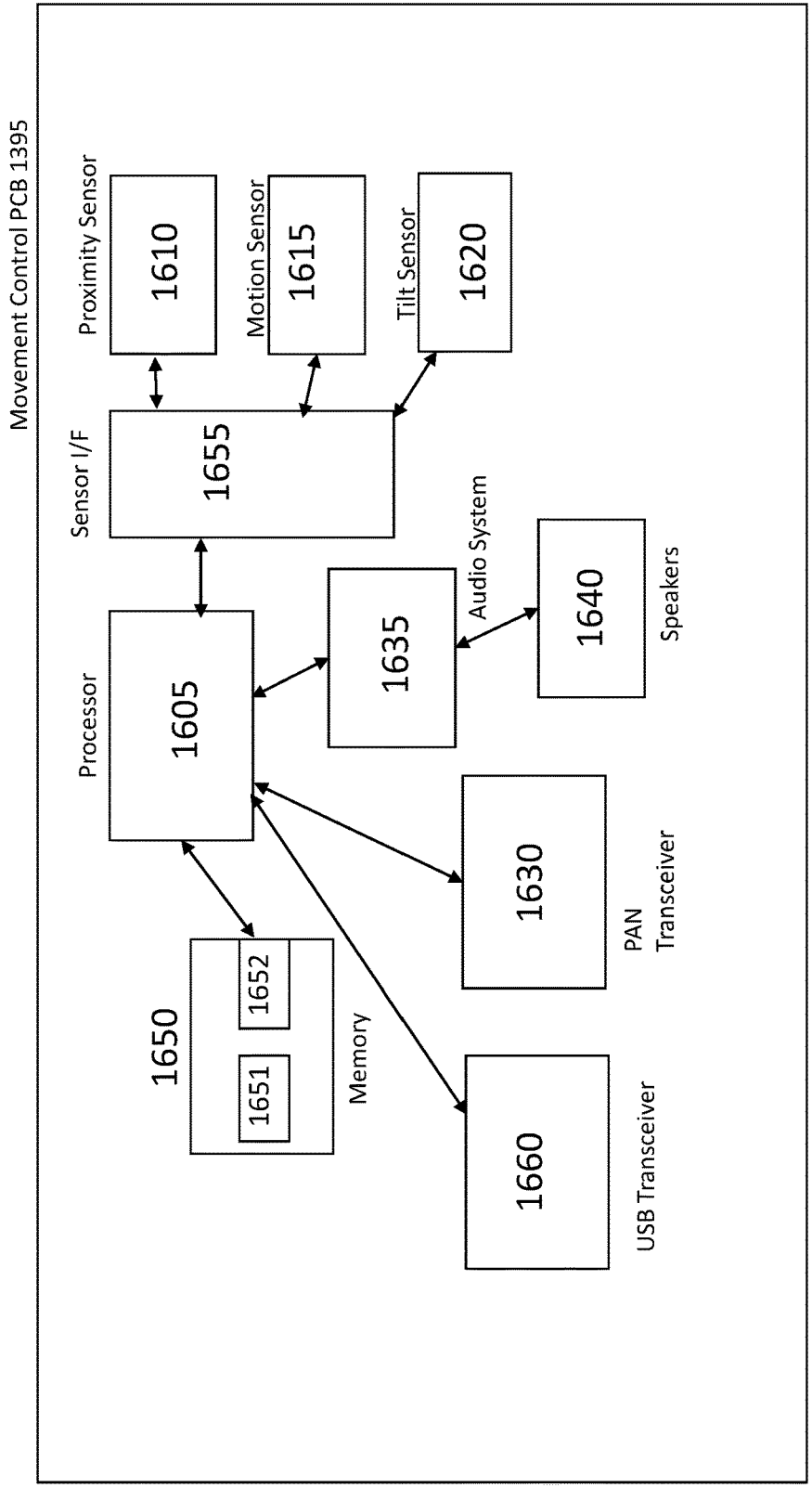
FIG. 16 illustrates a block diagram of a movement control PCB according to embodiments.

FIG. 16 illustrates a block diagram of a movement control PCB according to embodiments. Returning back to discussion of a movement control PCB, in embodiments, a movement control PCB 895 may comprise a processor/controller 1605, a proximity sensor 1610, a motion sensor 1615, a tilt sensor 1620, a personal area network transceiver 1630, an audio receiver 1635 (optional), one or more speakers 1640, and/or a memory 1650 having modular umbrella or shading object control software (e.g., executable instructions stored in a non-volatile memory 1651 and executable by a processor 1605). In embodiments, an umbrella movement control PCB 1395 may comprise a USB transceiver 1360. In embodiments, an umbrella movement control PCB 1395 may comprise sensor interface subsystem 1655 for communicating sensor measurements to an umbrella movement control PCB 1395 and communicate commands and/or signals from and two to external sensors. In embodiments, a sensor interface subsystem 1655 may be located, or may also be located on a telemetry PCB 1305, a weather variable PCB 1310, and/or first, second, or third motor control PCBs 1380, 1385, and 1390. For example, in embodiments, a modular umbrella shading system may also include a signal conditioning subsystem which may also be referred to as a sensor interface system and the terms may be utilized interchangeably throughout the specification. In embodiments, an intelligent shading object, umbrella and/or shading charging system (and the signal conditioning subsystem) may further comprise one or more reference signal modules, one or more signal conditioning modules, and one or more analog-to-digital converters. In an embodiment, one or more sensors (e.g., air quality sensor 1611, UV radiation sensor 1612, wind speed sensor 1617, motion sensor 1645, and/or tilt sensor 1655) may receive communicated analog signals and may transmit analog signals to signal conditioning modules 1655. In embodiments, a signal conditioning module 1655 may process and/or condition communicated analog sensor signals. Although signals are described as being analog, the description herein equally applies to digital signals. In embodiments, one or more signal conditioning modules may communicate and/or transfer processed and/or conditioned signals to one or more A-to-D converters. In embodiments, one or more signal reference modules may be a non-volatile memory, or other storage device, that stores and/or retrieves signal values that the communicated signal values may be compared to in order to determine if threshold conditions may be met. In embodiments, a comparison of communicated signal values to reference signal values may allow the signal conditioning system to understand if normal conditions are being experienced by a modular umbrella shading system or if a modular umbrella shading system may be experiencing abnormal conditions, (e.g., high humidity, high movement, high wind, and/or bad air quality).

FIG. 16 illustrates an umbrella movement control PCB according to embodiments. In embodiments, an umbrella movement control PCB 1395 may comprise a proximity sensor 1340. In embodiments, a proximity sensor 1340 may be able to detect a presence of nearby objects, (e.g., people or other physical objects) without any physical contact between a sensor and an object. In embodiments, a proximity sensor 1340 be located on and/or mounted on a movement control PCB 1395. In embodiments, a proximity sensor 1340 may be located on and/or mounted on other printed circuit boards or may be a standalone component in a shading object system. In embodiments, a proximity sensor 1340 may be located within a core assembly or module 130. In embodiments, a proximity sensor 1340 may generate measurements and/or signals, which may be communicated to a processor/controller 1605 in a movement control PCB 1395. In embodiments, an umbrella movement control board 1605 may store communicated measurements and/or signals, which has instructions stored thereon. In embodiments, proximity sensor software instructions, which are fetched from memory 1650 and executed by a processor 1605, may perform and/or execute a proximity process or method. In embodiments, for example, a proximity process may comprise receiving measurements and/or signals from a proximity sensor 1340 indicating an object and/or person may be located in an area where a shading object is deployed, going to be deployed and/or extended, and/or towards where a component of a shading object may be moving. For example, if an individual is located in an area where arm support assemblies may be deployed and/or extended, a proximity sensor 1340 may transmit a signal or measurement indicating an object may be an obstruction to, for example, a movement control PCB 1395. In embodiments, a processor/controller 1605 in a movement control PCB may receive and/or analyze a proximity measurement and determine an object may be an obstacle. In embodiments, a proximity signal and/or command may also identify a location of an object (e.g., obstacle) in relation to a proximity sensor 1340 and/or some reference location. In embodiments, a processor of a movement control PCB may generate and/or communicate a driving signal, command, and/or instruction that instructs a shading object not to deploy and/or open. In embodiments, for example, a processor/controller 1605 in a movement control PCB 1395 may communicate a signal and/or commands to a third motor controller to cause the third motor to stop moving the arm/blade support assembly 163 due to an obstacle detection. In embodiments, for example, a movement control PCB 81395 may communicate a signal and/or commands to a second motor controller a second motor (articulating and/or elevation motor) to cause a second motor to stop moving an gearbox assembly and/or actuator and prevent an upper core assembly 140 of a core assembly or module from moving into an area where an obstacle is detected. In embodiments, this may also work in the opposite direction, where if a proximity sensor 1340 does not determine that an object is within a modular umbrella shading system area, then a proximity sensor signal may not be communicated to the processor/controller 1605 in a movement control PCB 1395.

In embodiments, an umbrella movement control PCB 1395 may comprise a motion sensor 1345. In embodiments, a motion sensor 1345 may generate a signal and/or measurement indicating that an individual, a living organism, or an object is within an area covered by a motion sensor 1345. For example, a motion sensor 1345 may generate a signal if an individual and/or object is approaching a modular umbrella shading system, is within 5 or 10 feet of an umbrella, or is moving within a shading area. In embodiments, a motion sensor 1345 may be located on and/or mounted on a movement control PCB 1395. In embodiments, a motion sensor 1345 may be located on and/or mounted on other printed circuit boards or may be a standalone component in a shading object system. In embodiments, a motion sensor 1345 may be located within a core assembly or module 130. In embodiments, a motion sensor 1345 may generate measurements and/or signals, which may be communicated to a processor/controller 1605 in a movement control PCB 1395. In embodiments, an umbrella movement control board 905 may store communicated measurements and/or signals, in a memory 1650. In embodiments, motion sensor software instructions, may be fetched from memory 1650 and executed by a processor 1605, and may cause a processor 1605 to perform and/or execute a motion detection process or method.

Figure 17:
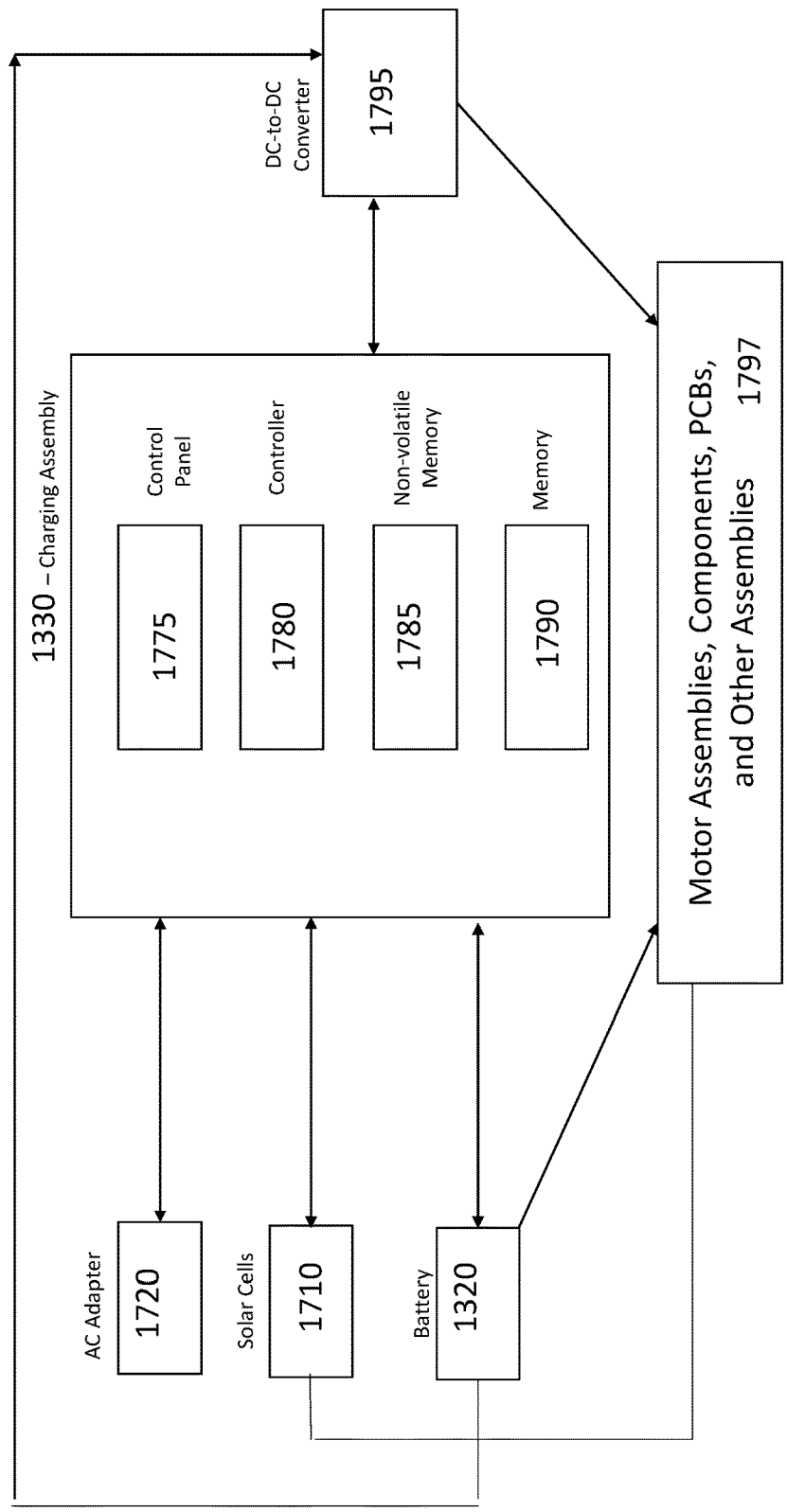
FIG. 17 illustrates a power subsystem in a modular umbrella system according to embodiments.

FIG. 17 illustrates a power subsystem in a modular umbrella system according to embodiments. In embodiments, a modular umbrella shading system may comprise a power tracking solar charger 1330. In embodiments, a core module assembly 130 of a modular umbrella shading system may comprise and/or house a power tracking solar charger 1330. Continuing with this illustrative embodiment, a power tracking solar charger 1330 may be located in and/or on an upper core assembly 140 of a core module assembly 130, or alternatively in or on a bottom core assembly 142 of a core module assembly 130. In embodiments, a power tracking solar charger 1330 may be connected to one or more solar cells 1710, a rechargeable battery 1320, and/or an AC adapter 1335 or 1720. In embodiments, a photovoltaic (PV) cell, or "solar cell" may be a smallest semiconductor element that converts sunlight into electricity. In embodiments, a semiconductor silicon may be treated so that silicon generates a flow of electricity when a light shines on it. In embodiments, a PV array or cells may be an interconnected system of PV cells that may function as a single electricity-producing unit. In embodiments, a PV array 1710 may comprise one of more of the strips of solar cells. In embodiments, a PV array 1710 may comprise one solar cell strip. In embodiments, one or more solar cells 1710 (e.g., a PV array 1710) may provide power directly to a power tracking solar charger 1330 and/or a rechargeable battery 820. In embodiments, one or more solar cells 1710 (or solar arrays) may provide power to motor assemblies, components, printed circuit boards, and/or other assemblies 1797 in a modular umbrella shading system.

In embodiments, a power tracking solar charger 1330 may be coupled and/or connected to a rechargeable battery 1320. In embodiments, a power tracking solar charger 1330 may be coupled and/or connected to an AC adapter 1335 (or DC power adapter), which is coupled and/or connected to a power source. In embodiments, a charging assembly 1330 may be coupled to one or more solar cells 1710 or solar arrays. In embodiments, a power tracking solar charger 1330 may include a control panel 1775, a controller 1780, a non-volatile memory 1785 and a volatile memory 1790, the non-volatile memory 1785 comprising computer-readable and computer-executable instructions, which are fetched and loaded into volatile memory 1790 for execution by a controller or processor 1280 to perform a power monitoring, tracking and distribution process. In embodiments, a power monitoring, tracking and/or distribution process may monitor power levels and/or power conditions of different components of a shading object (e.g., a motion control PCB 1395, arrays of solar cells 1710), a rechargeable battery 1320). In embodiments, a power tracking and monitoring process may communicate information regarding power levels and/or power conditions of a solar charger 1330 (and other shading object components) to a control panel 1775 and/or to a portable electronic device to display to a user and/or owner.

In embodiments, a power tracking solar charger 1330 may transfer incoming power (e.g., voltage and/or current) generated by the solar cells to one or more converters (e.g., a DC-to-DC converters) 1795. In embodiments, a rechargeable battery 1320 may provide power (e.g., voltage and/or current) to a DC-to-DC converter 1795. In embodiments, one or more DC-to-DC converters 1795 may transfer voltage and/or current to one or more PCBs, components, motor assemblies, and/or other assemblies of a shading object. In embodiments, a DC-to-DC converter 1795 may be utilized to provide lower operating voltages, e.g., 3.3 VDC or 5.0 VDC or other voltages, to components, boards and/or assemblies 1797 operating on a lower DC voltage. In embodiments, rechargeable battery 1320 may transfer incoming power (e.g., voltage and/or current) to one or more converters 1795, and a power charger 1330 may monitor power distribution and power levels. In embodiments, a rechargeable battery 1320 may provide power to shading object or umbrella motor assemblies, PCBs, components, and/or assemblies 1797. If high power requirements are existing due to operating conditions (e.g., motors running), a rechargeable battery 1320 and solar cells or solar cell arrays may both provide power to one or more PCBs, components, motor assemblies, and/or other assemblies of a shading object.

In embodiments, a modular umbrella shading system may comprise a voice recognition engine 1315. In embodiments, a shading object motion control PCB 1395 may have a voice recognition engine 1315 mounted and/or located thereon. A voice recognition engine is described in detail in U.S. non-provisional patent application Ser. No. 15/160,856, filed May 20, 2016, entitled "Automated Intelligent Shading Objects and Computer-Readable Instructions for Interfacing With, Communicating With and Controlling a Shading Object," and U.S. non-provisional patent application Ser. No. 15/160,822, filed May 20, 2016, entitled "Intelligent Shading Objects with Integrated Computing Device, the disclosure of both applications being hereby incorporated by reference.

In embodiments, a modular umbrella shading system may comprise one or more digital cameras 1357 and/or other analog-based cameras. In embodiments, one or more cameras 1357 may comprise an optical system and/or an image generation system. In embodiments, digital cameras 1357 may display images on a screen immediately after being captured. In embodiments, one or more digital cameras 1357 may store and/or delete images from a memory associated with a digital camera. In embodiments, one or more digital cameras 857 may capture, record and/or moving videos with or without sound. In embodiments, digital cameras 1357 may also incorporate computer-readable and computer-executable instructions which, which when retrieved from a non-volatile memory, loaded into a memory, and executed by a processor, may crop and/or stitch pictures, and/or potentially perform other image editing on captured images. For example, image stitching or photo stitching is the process of combining multiple photographic images with overlapping fields of view to produce a segmented panorama and/or high-resolution image. In embodiments, image stitching may be performed through the use of computer software embodied within a digital camera. In embodiments, a digital camera may also internally perform video stitching. In embodiments, other devices, components and/or assemblies may perform image stitching, video stitching, cropping and/or other photo editing. In embodiments, computer-readable instructions loaded into a memory of a movement control PCB 1395 and/or integrated computing device 1360, may be executable by a processor to perform image stitching, video stitching, cropping and/or other photo editing. In embodiments, computer-readable instructions may be loaded into a memory located within a modular umbrella shading system and executable by a processor to perform the above-identified photo editing.

In embodiments, cameras may capture images of an area around, surrounding, and/or adjacent to shading objects, intelligent umbrellas, and/or intelligent shading charging systems. In embodiments, a stem assembly 106 and/or a central support assembly 107 may comprise a camera 857. In embodiments, a stem assembly 106 and/or center support assembly 107 may rotate (e.g., up to 360 degrees) about a vertical axis with respect to a base assembly 105—FIGS. 1A and 1B) (or a lower support assembly 187 and/or an upper support assembly 191 may rotate about and/or around a housing and/or enclosure 182—FIG. 1C) and this may allow a camera to capture images, videos and/or sound corresponding to 360 degrees of an area surrounding, around and/or adjacent to a shading object, intelligent umbrella and/or intelligent shading charging system. In embodiments, a camera 857 and/or other components or assemblies (as discussed above) may stich or combine images and/or videos to provide a panoramic image of the area. The ability of a shading object to rotate allows a benefit of panoramic image capture and not just an area where a camera is initially oriented. In embodiments, a camera 857 may have one or more images resolutions (e.g., 1 Megapixel (MP), 3 MP, 4 MP, 8 MP, 13 MP and/or 38 MP) that are selectable and/or adjustable.

Figure 18:
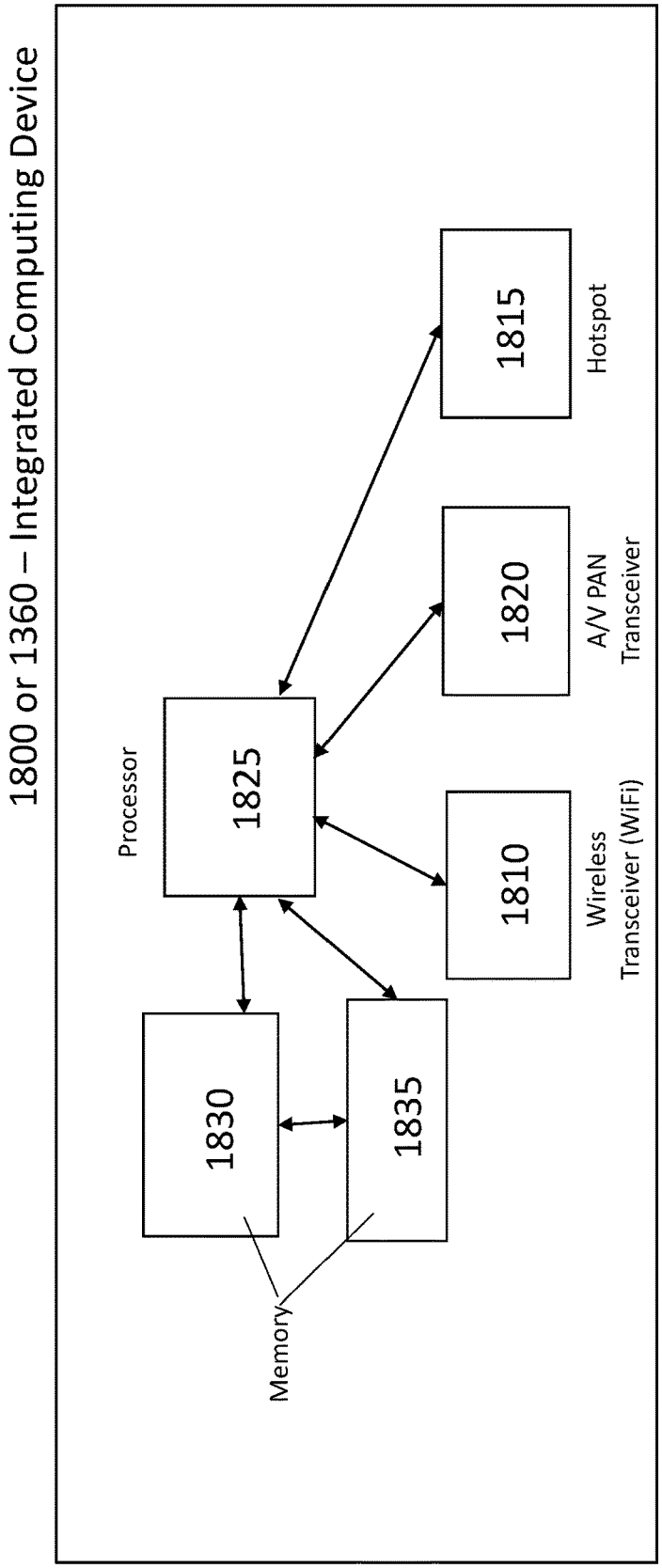
FIG. 18 illustrates a shading object or umbrella integrated computing device in a modular umbrella system according to embodiments.

FIG. 18 illustrates a shading object or umbrella integrated computing device in a modular umbrella system according to embodiments. In embodiments, an integrated computing device PCB 1800 may comprise a wireless WiFi or LAN wireless transceiver 1810 (which may or may not operate as a wireless hotspot and/or router), a separate wireless hotspot device 1015, one or more audio/video transceivers 1820 (e.g., PAN transceivers), one or more processors 1825, one or more non-volatile memories 1830 and one or more memory components 1835. In embodiments, many of the components may reside on a computing device PCB. In embodiments, a separate PCB may house or have some of the above-listed components (e.g., local area network or WiFi transceiver 1810, wireless hotspot device 1815) mounted thereon and a shading object computing device may comprise non-volatile memory 1830 (e.g., a flash drive, a hard drive, a removable disk drive), and a volatile memory 1835 such as RAM, and on or more processors 1825.

In embodiments, computer-readable and/or computer-executable instructions may be stored in non-volatile memory, fetched by one or more processors 1825, loaded into RAM 1835, and executed by one or more processors 1825 to perform data intensive functions, execute processes such as a healthcare process (e.g., selecting a healthcare option from a dashboard of a mobile application), a security process (e.g., selecting a security option from a dashboard of a mobile application), an energy process or application (e.g., selecting an energy option from a dashboard of a mobile application), a weather application or processor (e.g., selecting a weather option from a dashboard of a mobile application), and/or communicating with external devices (e.g., wireless access points, portable electronic devices, servers, networks). In embodiments, an integrated computing device 860 and/or a computing device PCB may consume more power due to higher data throughput and higher utilization time. Having a computing device integrated into an intelligent shading object or umbrella, provides a benefit, as to prior art shading objects or umbrellas, of allowing an intelligent shading object to run software applications, communicate with data intensive devices, such as cameras and/or audio system, utilize WiFi or other wireless communication transmissions, operate as a WiFi hotspot (or other wireless communication hub) and communicate with external computing devices to transfer data obtained by the intelligent shading object.

In embodiments, an integrated computing device 1800 may communicate with application servers, mobile applications servers, proxy servers, and/or other computing devices on a global communications network (e.g., the Internet). In embodiments, a computing device may handle data and/or command communications between external devices and a shading object. In embodiment, an integrated computing device 1360 may handle intra-shading object communications requiring more extensive processing power and/or higher data transfer rates. In embodiments, a core module assembly 130 may house an integrated computing device. In embodiments, a core module assembly 130 may also house a computing device PCB to which a computing device 1360 may be attached to and/or connected.

In embodiments, an integrated computing device 1360 or 1800 may be a Linux-based computing device (e.g., Raspberry PI) although other operating systems and/or other processor types may be utilized. In embodiments, a shading object may comprise one or more transceivers to communicate with wireless access points utilizing a wireless communication protocol. In embodiments, one or more wireless transceivers may communicate voice and/or data communications to an access point, which in turn may communicate received voice and/or data communications to a packet-switched network (e.g., a global communications network such as the Internet, an intranet, or a private network) or a circuit-switched network (such as existing telecommunications system).

In embodiments, an integrated computing device may comprise a WiFi (or wireless LAN) transceiver 1810 which may also operate as a hotspot and/or personal wireless access point. In embodiments, an integrated computing device 860 may comprise a separate and/or additional wireless hotspot 1815. In embodiments, a wireless hotspot may be operate as an wireless access point providing network and/or Internet access to portable electronic devices (e.g., smartphones, music players) or other electronic devices (personal computers and/or laptops) in public locations, where other wireless access points are not located (or being utilized for different purposes). If a computing device 1360 comprises a wireless hotspot 1815 (or a wireless transceiver 1810 is operating as a hotspot), wireless communication devices (e.g., laptops, tablets, smartphones) may utilize a shading object as a communications hub. This may be beneficial in remote locations where no wireless access points are located, or in locations where wireless data or voice communications have been interrupted. In addition, if a shading object computing device and thus a shading object includes a wireless hotspot, image or video streaming, face-timing, application downloads, or other data intensive functions and/or applications may execute and be completed in a shorter amount of time then when using a PAN transceiver 1365.

In embodiments, an integrated computing device 1360 or 1800 may store and/or execute shading object or umbrella application software, which may be referred to as SMARTSHADE and/or SHADECRAFT application software. In embodiments, shading object or umbrella application software may be run and/or executed on a variety of computing devices including a computing device integrated within a shading object or umbrella. In embodiments, for example, shading object or modular umbrella application software may include computer-readable instructions being stored in non-volatile memories of a computing device, a portable electronic device (e.g., a smart phone and/or a tablet), an application server, and/or a web application server, all which interact and communicate with each other. In embodiments, computer-readable instructions may be retrieved from memories (e.g., non-volatile memories) of these above-identified computing devices, loaded into volatile memories and executed by processors in the computing device, portable electronic device, application server, and/or mobile application server. In embodiments, a user interface (and/or graphical user interface) for a modular umbrella software application may be presented on a portable electronic device, although other computing devices could also execute instructions and present a graphical user interface (e.g., dashboard) to an individual. In embodiments, modular umbrella application software may generate and/or display a dashboard with different application (e.g., process) selections (e.g., weather, health, storage, energy, security processes and/or application processes). In embodiments, modular umbrella application software may control operation of a modular umbrella, communicate with and receive communications from modular umbrella assemblies and/or components, analyze information obtained by assemblies and/or components of a modular umbrella, integrate with existing home and/or commercial software systems, and/or store personal data generated by the modular umbrella, and communicate with external devices.

In embodiments, a portable electronic device may also comprise a mobile application stored in a non-volatile memory. In embodiments, a mobile application may be referred to as a SHADECRAFT or a SMARTSHADE mobile application. In embodiments, a mobile application (mobile app) may comprise instructions stored in a non-volatile memory of a portable electronic device, which can be executed by a processor of a portable electronic device to perform specific functionality. In embodiments, this functionality may be controlling of, interacting with, and/or communicating with a shading object. In embodiments, mobile apps may provide users with similar services to those accessed and may be individual software units with limited or specific function. In embodiments, applications may be available for download from mobile application stores, such as Apple's App Store. In embodiments, mobile apps may be known as an app, a Web app, an online app, an iPhone app or a smartphone app. In embodiments, a sensor device (or other IoT device) may communicate to a server computing device via a cellular communications network, a wireless communication network, a wired communication network and/or other communication network. In embodiments, a sensor device and/or assembly device may capture sensor measurements, data and/or conditions and may communicate sensor measurements, data and/or conditions to an IoT enabled server, which may analyze, store, route, process and/or communicate such sensor measurements, data and/or conditions. In embodiments, an Internet of Things (IoT) may be a network of physical objects—sensors, devices, vehicles, buildings, and other electronic devices. In embodiments, the IoT may sense and/or control objects across existing wireless communication network infrastructure, an existing cellular communication network, and/or a global communications network infrastructure. In embodiments, integrating of devices via IoT may create opportunities for more direct integration of a physical world into computer-based systems, which may result in improved efficiency, accuracy and economic benefit. In addition, when an IoT device or server is augmented with sensors and actuators, IoT may be integrated or enabled with a more general class of cyber-physical systems, e.g., smart grids, smart homes, intelligent transportation and smart cities. In embodiments, in IoT, for example, may be uniquely identifiable through its embedded computing system but is able to interoperate within the existing Internet infrastructure. In embodiments, a device may have a specific IP address in order to be addressed by other IoT enabled systems and/or devices. In embodiments, an IP address may be provided and/or established by routers and/or Internet service providers. For example, a modular umbrella enabled with IoT capability, because it may incorporate cameras, may be able to communicate with or be integrated into a home or office security system. Further, if an individual has a smart home, an individual may be able to control operation of, or communicate with a modular umbrella shading system as part of an existing smart home software application (either via a smart phone, mobile communication device, tablet, and/or computer). In addition, a modular umbrella shading system, if part of IoT, may be able to interface with, communicate with and interact with an existing home security system. Likewise, a modular umbrella shading system may be able to be an additional sound reproduction device (e.g., via speaker(s)) for a home audio and/or video system that is also on the IoT. In addition, a modular umbrella system may be able to integrate itself with an electronic calendar (stored on a computing device) and become part of a notification or alarm system because it will identify when upcoming meetings are occurring.

In embodiments, a modular umbrella system may be a device on an Internet of Things (IoT). In embodiments, an IoT-enabled device may be one or more cameras, one or more environmental sensors, one or more directional sensors, one or more movement sensors, one or more motor assemblies, one or more lighting assemblies and/or one or more solar panels or cells. These objects and/or IoT-enabled devices may comprise items and/or device may be embedded with electronics, software, sensors, and network connectivity, which enables these physical objects to detect, collect, process and/or exchange data with each other and/or with computing devices, Shadecraft IoT-enabled servers, and/or third-party IoT enabled servers connected to a modular umbrella system via a global communications network (e.g., an Internet).

In embodiments, IoT devices (e.g., servers, sensors, appliances, motor assemblies, outdoor shading systems, cameras, lighting assemblies, microphones, computing devices, etc.) may communicate with each other utilizing an Internet Protocol Suite. In embodiments, IoT devices may be assigned an IP address and may utilize IPv6 communication protocol. In embodiments where security is important, authentication may be established utilizing OAUTH (e.g., version 2.0) and Open ID Connect protocols (e.g., version 1.0). In addition, in embodiments, the IEEE 802.15.4 radio standard may allow for reduction in power consumption by IoT devices utilizing RF communications. In embodiments where power consumption may need to be decreased, e.g., as in sensors, modular umbrella shading systems, shading systems, cameras, processors), communication with IoT devices may utilize Message Queuing Telemetry Transport (MQTT) which utilizes TCP for its transport layer and utilizes a central MQTT broker to manage and/or route messages among a MQTT network's nodes. In embodiments, communication with IoT devices may utilize Constrained Application Protocol (CoAP) which utilizes UDP as its transport protocol. In embodiments, CoAP may be a client/server protocol and allows a one-to-one report/request instruction model. In embodiments, CoAP also may have accommodations for multi-cast transmission of messages (e.g., one to many report/request instruction model).

Figure 22:
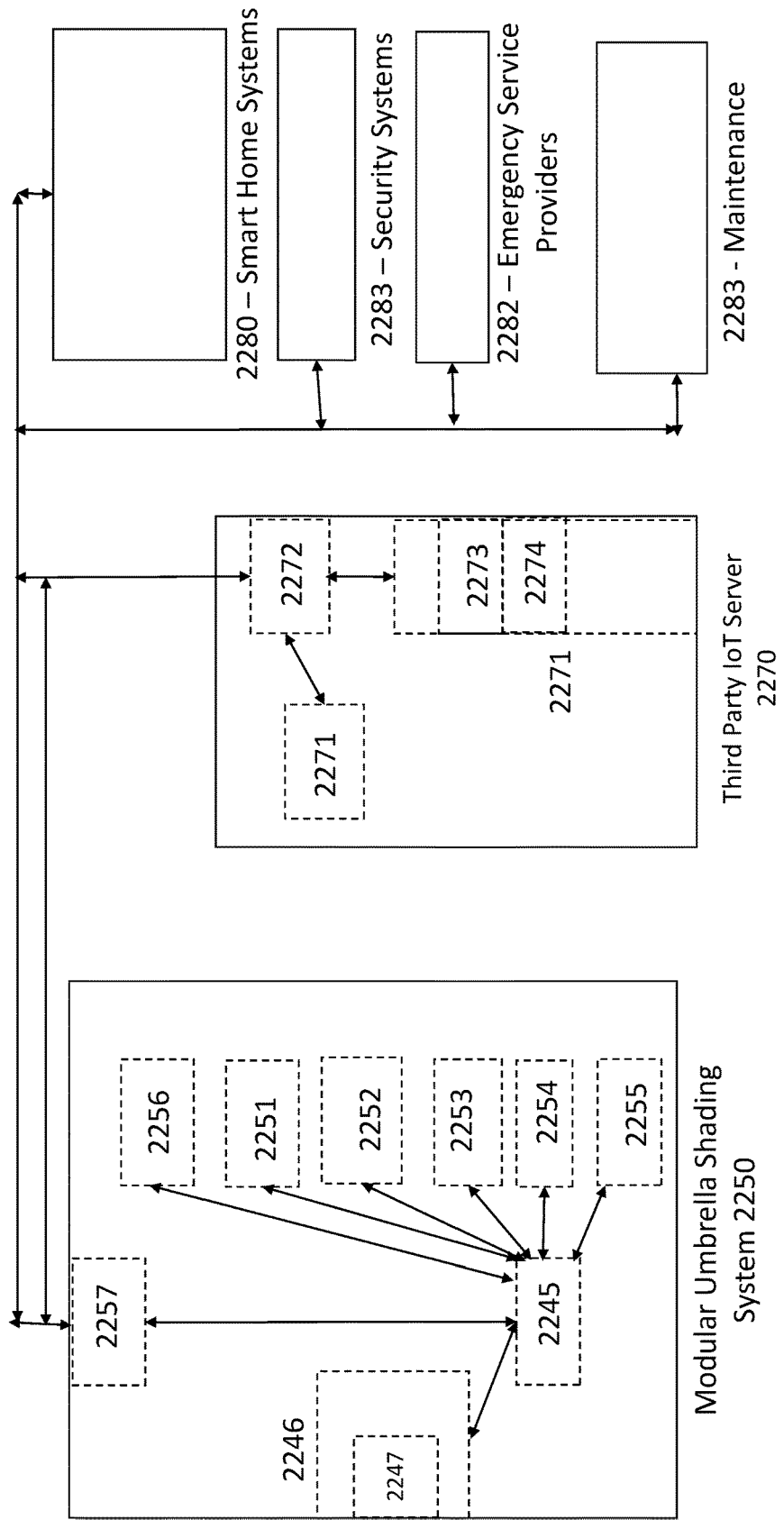
FIG. 22 illustrate a modular umbrella shading system communicating with an IoT-enabled server or computing device according to embodiments.

FIG. 22 illustrates a modular umbrella shading system communicating with an IoT-enabled server or computing device according to embodiments. If a modular umbrella system is integrated into IoT, for example, a modular umbrella system 2250 and/or IoT-enabled devices integrated or installed thereon may be part of a smart home, a smart office and/or a smart city. For example, a smart home may already include one or more IoT-servers 2270 (e.g., a NEST server may have a computing device and/or server) for controlling operations of IoT devices (alarms, appliances, lights) installed within a smart home, office or building. In embodiments, one or more modular umbrella systems 2250 (and one or more IoT-enabled devices) may be incorporated into such a smart home, office or building. For example, one or more environmental sensors (e.g., temperature, humidity, air quality, UV radiation, wind speed sensors, and/or a digital barometer) may capture and communicate measurements and/or status readings to an IoT-enabled smart home server 2270. In embodiments, measurements and/or status readings may be communicated using a smart home API 2247 (instructions executed by a processor) through a modular umbrella system transceiver 2257 (e.g., local area network wireless (or WiFi) transceiver, cellular transceiver, PAN transceiver) to an IoT-enabled smart home server 2270. In embodiments, temperature and/or humidity measurements from a temperature and/or humidity sensor 2251 may be communicated to the IoT-enabled smart home server, where the IoT-enabled smart home server 2270 may analyze the temperature and/or humidity measurements and may adjust commands, instructions and messages transmitted to cooling and/or heating systems 2280 in a smart home. In embodiments, UV radiation sensor measurements and/or air quality sensor measurements from a radiation sensor or air quality sensor 2252 may be communicated to an IoT-enabled smart home server 2270, the UV measurements may be utilized as input for a personal health software application 2273 (e.g., recommend sunscreen or period of sun exposure recommended for a home resident) and/or may be stored for later reporting and/or analyzation. In embodiments, air quality sensor measurements may be utilized 1) as input for a personal health software application (e.g., recommend whether to take asthma medication, whether to where mask due to large amount of allergens in air); 2) to trigger alarm conditions within a smart home (e.g., carbon monoxide or other gas readings too high); and/or 3) by the smart home server to communicate with emergency service provider servers or computing devices 2282 (e.g., utility companies, fire departments, police departments) due to over threshold and dangerous sensor measurements. In embodiments, barometer measurements from a barometer 2253 may be utilized by IoT-enabled smart home servers 2270 as input for a weather software application 2274 as one of a plurality of factors utilized for determining and/or predicting weather conditions.

In embodiments, solar cells and/or cells 2254 (and/or a solar charger assembly) may communicate solar panel status and/or solar power measurements to a smart home server 2270 via a smart home application programming interface (API) 2247 utilizing a transceiver 2257. In embodiments, a smart home server 2270 may receive solar panel (or cell) status and determine whether to alert a solar cell maintenance computing device as to a potential service call. In embodiments, a smart home server 2270 may receive solar panel or cell power generation measurements and utilize these to identify solar power generated by user of smart home (e.g., add it to any green power generated by smart home). In embodiments, a smart home server 2250 may receive solar power generation measurements as well as unused solar power measurements and identify whether or not to draw excess power from a modular shading umbrella system.

In embodiments, sensors on one or more motor assemblies (or motor assemblies themselves (if IoT enabled)) 2255 may communicate motor assembly status and/or motor assemblies failure codes to an IoT-enabled smart home server 2270 via a smart home API 2247 utilizing a transceiver 2257. In embodiments, a smart home server 2270 may receive communicated motor assembly status and/or failure codes and may contact a maintenance computing device 2283 to set up a service call and/or order parts.

In embodiments, one or more IoT-enabled motion sensors 2256 may communicate motion sensor status and/or motion sensor measurements through a smart home/office API 2247 resident within one or more memory modules 2246 on a modular umbrella system. In embodiments, a smart home server 2270 may receive communicated motion sensor status and/or motion sensor measurements and analyze status and/or measurements to identify when and/or where motion has been detected in the area around the smart home and/or office. In embodiments, for example, in response to motion detection measurements, a smart home server 2270 may communicate signals, messages, instructions and/or commands to other assemblies 2280 connected via IoT to a smart home. For example, a smart home server may communicate a message and/or command to one or more lighting assemblies in a smart home in an area where a smart umbrella motion sensor has detected movement. Similarly, in embodiments, a smart home server may communicate a message and/or instruction to an audio receiver and/or speaker 2280 to emit an alarm and/or spoken phrase in an area where motion has been detected. In embodiments, a smart home server 2270 may communicate a message, instruction, and/or messages to a modular umbrella system via a smart home API 2247 to initiate and/or activate one or more cameras to capture video, images and/or audio from an area where motion has been detected. In such embodiments, for example, one or more cameras may transmit and/or communicate video, audio and/or images to a smart home server via a smart home API. In embodiments, a smart home server 2270 may communicate received images, video and/or audio to a home or office security system or computing device 2283 for monitoring by security personnel or residents of a smart home, office and/or building. In embodiments, received images, video and/or audio may be stored in memory 2271 of a smart home server 2270. In embodiments, a smart home server 2270 may be located within a smart home or office, or may be located in a remote and/or third-party location (e.g., a cloud-based server).

Figure 23:
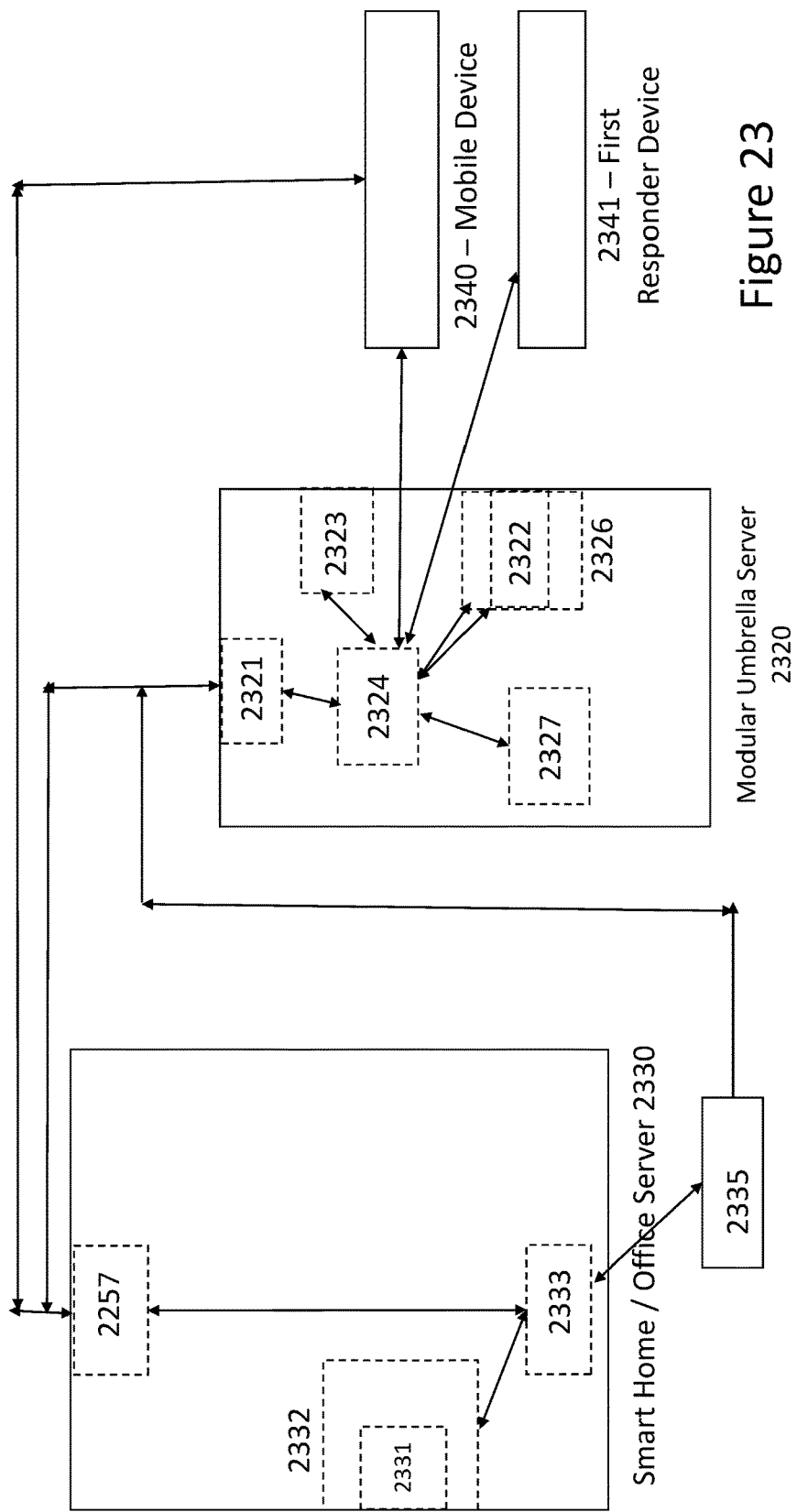
FIG. 23 illustrates a smart home or smart office IoT-enabled server communicating and transferring information to a modular umbrella shading system according to embodiments.

FIG. 23 illustrates a smart home, smart office or smart building IoT-enabled server communicating and transferring information to a modular umbrella shading system according to embodiments. In embodiments, a smart home, office and/or building IoT-enabled server 2330 may also communicate with an IoT-enabled modular umbrella system 2320 and/or one or more IoT-enabled devices within a modular umbrella system 2320. For example, in embodiments, a smart home, office or building server and/or computing device 2330 software application (e.g., computer-readable instructions 2331 stored in one or more memory modules 2332 executable by one or more processors 2333) may communicate audio files or streams, video files or streams, executable software files, software updates and/or revisions, and/or alarm/emergency conditions to a modular umbrella system 2320. For example, a smart home or office server or computing device 2330 and/or software application may receive a selection from a user to play a specific digital music playlist from a the smart home or smart office server 2330 or a third party cloud-based server (e.g., such as iTunes) or a digital music repository 2335. In embodiments, digital and/or audio files may be communicated and/or transferred from a third-party cloud-based server and/or from a smart home server to a modular umbrella system 2320 via a transceiver 2321 (and/or smart home application programming interface (API) or digital music API 2322). In embodiments, one or more processors 2324 may communicate audio and/or video files to an audio receiver and/or speaker 2323. In embodiments, a modular umbrella system 2320 audio receiver and/or speaker 2323 may reproduce sound communicated and/or streamed in digital and/or analog audio from a smart home server 2330 and/or cloud-based server 2335. In embodiments, video files and/or images files may also be communicated to a modular umbrella shading system 2320 and presented on a display and/or monitor of a modular umbrella shading system 2320.

In embodiments, a smart home, office and/or building server 2330 and/or application software stored in one or more memory modules 2332 may transfer and/or communicate software updates and/or revisions to a computing device, a circuit board, a microcontroller, a processor and/or electronic computer assemblies 2327 in a modular umbrella shading system 2320. In embodiments, the software revisions and/or updates may be communicated via a smart home, office or building API 2322 resident in memory 2326 of a modular umbrella shading system 2320.

In embodiments, a modular umbrella system 2320 may also be an additional node of a smart, office or building that may be utilized to communicate with emergency service providers and/or first responders in case of emergency. For example, in embodiments, if a smart home, office or building API 2322 does not receive communications and/or messages from a smart home server 2330 for a predetermined period of time (e.g., one minute, 30 minutes, and/or one hour), a smart home, office and/or building API 2322 may generate a message to be communicated to a mobile communication device 2340 associated with an owner or dweller of a smart home, office or building. In embodiments, a smart home API 2322 may utilize whichever modular umbrella shading system transceiver 2321 may still be operational, e.g., (utilize one or more of a cellular transceiver, a PAN transceiver and/or a local area network (WiFi or 802.11) transceiver 2321 to communicate message). In embodiments, if a mobile computing device 2340 of an owner and/or dweller does not respond to the smart home, office or building API 2322 (and/or processor 2324) within a predetermined period of time, a smart home, office or building API 2322 (and/or processor 2324) may transmit and/or communicate an alert message to an internal or third party security server (or computing device) and/or emergency service provider servers and/or computing devices (e.g., police department, or fire department) 2341 in order to notify of a potential emergency situation. In embodiments, an emergency and/or crime may be occurring in a certain area of a home and a certain part of a smart home or smart office system may not be accessible. For example, a robbery may be occurring and a user may not want to utilize devices inside an office or residence to communicate with emergency service personnel. In these situations, for example, a user may communicate with a smart home server 2330 (utilizing a mobile computing device, a remote device, and/or other electronic devices 2340) which may communicate with a smart home, office or building API 2322 in a modular umbrella system 2320 and request a message and/or command be communicated to an emergency service provider via a cellular transceiver, a local area network wireless (WiFi) transceiver, and/or a PAN transceiver. Further, a user may communicate with a smart home/office API 2322 in a modular umbrella shading system to turn on and/or activate components and/or assemblies 2327 of a modular umbrella system 2320 (e.g., a speaker may be activated and/or utilized to generate an alarm; a lighting system may be activated to surprise or startle an intruder; a camera may be activated to capture videos from an outside of an office, home or building).

Figure 24:
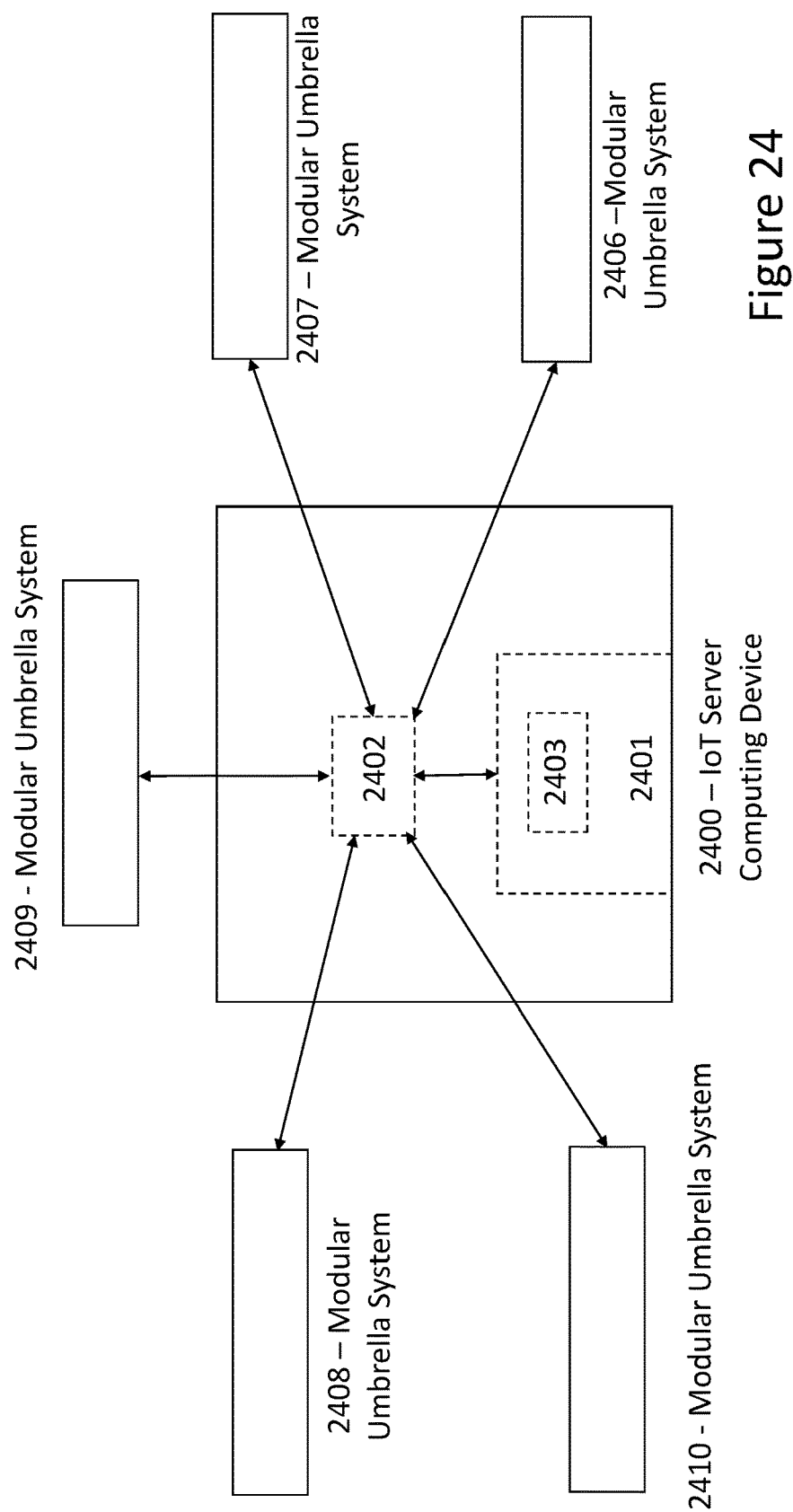
FIG. 24 illustrates a IoT software application communication with a plurality of modular shading umbrella systems according to embodiments

FIG. 24 illustrates an IoT software application communication with a plurality of modular shading umbrella systems according to embodiments. In embodiments, one or more people or entities may communicate with a plurality of modular shading systems located within a specified geographic area (e.g., a neighborhood, a city, a county, a state and/or a region). In embodiments, an IoT software application (e.g., computer-readable instructions 2403 stored in one or more memory modules 2401 and executed by one or more processors 2402 on a network server, a cloud-based server and/or a Shadecraft distributor server 2400 may communicate with a plurality of geographically distributed IoT-enabled modular umbrella shading systems 2406 2407 2408 2409 and/or 2410 and may receive information, status and measurements from a modular umbrella shading systems 2406 2407 2408 2409 and 2410 and/or IoT enabled sensors, devices and/or assemblies. For example, an owner, renter and/or user of modular shading systems may communicate with a number of modular umbrella shading systems (e.g., 2-150 modular umbrella shading systems) that may be coupled and/or connected as IoT nodes or devices. In embodiments, for example, a server or computing device 2400 executing IoT instructions and/or software 2403 may request and/or receive information from sensors located on one or more modular umbrella systems. The server or computing device 2400 executing IoT instructions and/or software 2403 may store received environmental sensor measurements for the one or more modular umbrella shading systems 2406 2407 2408 2409 and 2410. Additional analysis instructions executing on the server or computing device 2400 may generate reports presenting sensor readings, geographic locations for the one or more modular umbrella shading systems 2406 2407 2408 2409 and 2410; may identify environmental sensor measurements exceeding specified thresholds; or lack of sensor measurements (or out-of-range sensor measurements) which may identify sensor malfunctions.

In embodiments, a server and/or computing device 2400 executing IoT instructions (or software application 2403) may receive captured barometer measurements from barometers installed on and/or integrated into more than one modular umbrella shading systems 2406 2407 2408 2409 and 2410. In embodiments, weather reporting/predicting instructions executed by a processor 2402 of a server and/or a computing device 2400 may analyze received barometer measurements and location measurements or orientations and utilize these measurements in determining and/or predicting weather for geographic locations near and/or surrounding the more than one modular umbrella shading systems 2406 2407 2408 2409 and 2410.

In embodiments, a server and/or computing device 2400 executing IoT instructions or software 2403 may receive captured solar power generation measurements, solar cells or solar panels status, and/or solar power consumption measurements for more than one modular umbrella shading systems. In embodiments, solar panels and/or cells and/or a modular umbrella shading system may be IoT enabled. In embodiments, reporting instructions executed by one or more processors 2402 of a server and/or computing device 2400 may present solar power generation measurements and/or solar power consumption measurements for a selected number of modular umbrella shading systems. In addition, instructions executed by one or more processors 2402 of a server and/or computing device 2400 may compare and analyze solar power generation measurements and/or solar power generations measurements between different modular umbrella shading systems and may identify, for example, if certain modular umbrella shading systems 2406 2407 2408 2409 and 2410 are not operating at peak capacity and/or consuming larger amounts of solar power. In addition, instructions executed by one or more processors 2402 of a server and/or computing device 2400 may receive solar panel status indicators and assist in identifying whether solar panels or cells are malfunctioning. In embodiments, instructions executed by one or more processors of a server and/or computing device may also analyze whether a number or a group of solar panels or cells are experiencing a same failure and/or malfunction.

In embodiments, a server and/or computing device 2400 executing IoT instructions or software 2403 may receive captured shading system motor assembly status indicators and/or operating parameters and/or captured shading system computing device status indicators and/or operating parameters for more than one modular umbrella shading systems 2406 2407 2408 2409 and 2410. In embodiments, motor assemblies and/or computing devices (e.g., a Raspberry Pi), or a modular umbrella shading system may be IoT enabled. In embodiments, reporting instructions executed by one or more processors 2402 of a server and/or computing device 2400 may present 1) motor assembly status indicators and/or operating parameters along with a geographic location for a selected number of modular umbrella shading systems 2406 2407 2408 2409 and 2410 and/or 2) computing device status indicators and/or operating parameters along with a geographic location for a selected number of modular umbrella shading systems 2406 2407 2408 2409 and 2410. In addition, instructions executed by one or more processors 2402 of a server and/or computing device 2400 may receive motor assembly status indicators and/or operating parameters, and/or computing device status indicators and/or operating parameters to and assist in identifying whether motor assemblies and/or computing devices in a group of modular umbrella shading systems 2406 2407 2408 2409 and 2410 are malfunctioning. In embodiments, instructions executed by one or more processors 2402 of an IoT server and/or computing device 2400 may also analyze whether a number of motor assemblies and/or computing devices are experiencing a same failure and/or malfunction.

In embodiments, instructions executed by one or more processors 2402 on a server and/or computing device 2400 may be utilized to provide software updates, fixes and/or new versions to assemblies, devices and/or other components of one or more modular umbrella shading system. In embodiments, assemblies, devices and/or other components (e.g., computing devices, microcontrollers, processors, sensors, printed circuit boards) and/or a modular umbrella shading system may be IoT-enabled. In embodiments, instructions 2403 executed by the one or more processors 2402 on a server and/or computing device 2400 may transfer and/or communicate a software update to selected components on all of a number of modular shading systems. In embodiments, instructions executed by the one or more processors 2402 on a server and/or computing device 2400 may transfer and/or communicate software revisions to selected assemblies on a selected number of modular umbrella shading systems. This feature may allow a modular umbrella shading system to quickly provide software revisions and/or modifications to owners of modular umbrella shading systems 2406 2407 2408 2409 and 2410. In addition, additional software-based features, e.g., such as image recognition, may be provided quickly to purchasers.

In embodiments, a modular umbrella system 100 may comprise a backup battery and/or also a memory. In embodiments, a modular umbrella system may further comprise a power sensor. If a sensor (e.g., a voltage sensor, a current sensor, a fuse, or other power sensor) determines that a power outage has occurred and/or power has been discontinued from a modular umbrella system 100, a sensor may communicate a signal, message and/or command to a backup battery to provide power to components and/or assemblies of a modular umbrella system 100. In embodiments, a backup battery may provide power (e.g., voltage and/or current) to a processor and/or controller, and the processor and/or controller may communicate commands, messages, instructions and/or signals to shut down and/or retract components and/or assemblies to an original and/or storage position. In embodiments, a memory may also receive a signal from a sensor and/or backup battery, and a memory may load and/or communicate emergency shutdown computer-readable instructions to a processor and/or a controller for execution. For example, emergency shutdown computer-readable instructions may cause a processor and/or controller to communicate commands and/or instructions to first, second and/or third motor assemblies to move rotate to a starting position, retract arm support assemblies and/or move an upper support assembly to a vertical position (or rest position) with respect to a lower support assembly. In embodiments, shutdown computer-readable instructions may cause a processor and/or controller to communicate commands and/or instructions to a camera and/or sensors to turn off and/or deactivate these components.

Figure 19A:
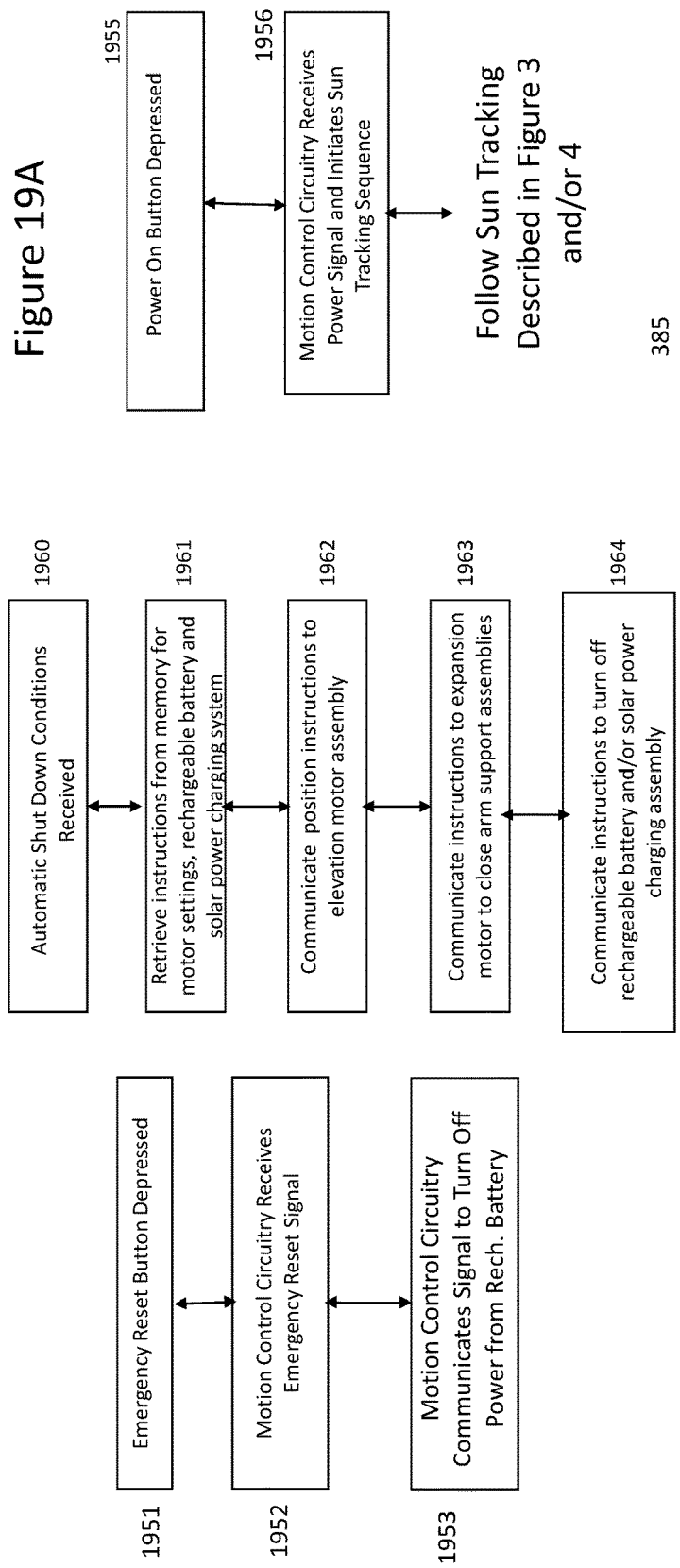
FIG. 19A illustrates a block diagram illustrating a power down sequences according to embodiments.
Figure 19B:
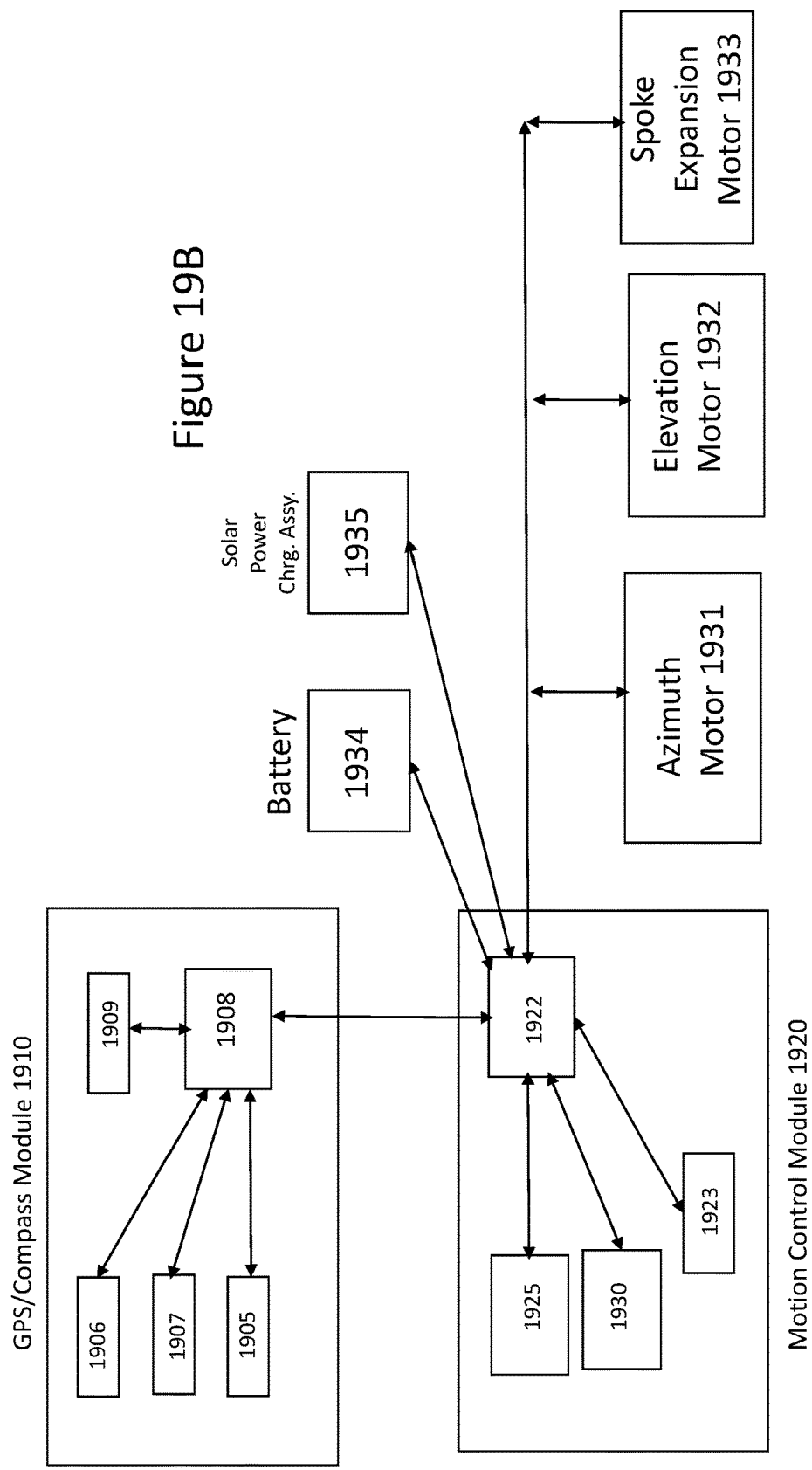
FIG. 19B illustrates a dataflow diagram illustrating power down sequences according to embodiments.

FIG. 19A illustrates a block diagram illustrating a power down sequences according to embodiments. FIG. 19B illustrates a dataflow diagram illustrating power down sequences according to embodiments. In embodiments, a core housing 130 may also comprise a gyroscope 1925 and an accelerometer 1930. In embodiments, an upper core housing 140 may comprise a gyroscope and/or an accelerometer. In embodiments, as illustrated in FIG. 19B, a motion control module 1920 (e.g., a motion control PCB) in a modular core housing 130 may comprise a processor/controller 1922, a memory 1923, one or more accelerometer 1925 and/or one or more gyroscopes 1930. In embodiments, directional measuring devices may refer to accelerometers, gyroscopes, compasses, magnetometers and/or GPS devices. In embodiments, a sensor module 1910 may comprise a compass, a digital compass and/or a magnetometer 1906, a GPS transceiver 1905, a clock 1907, a microcontroller 1908, and/or microcontroller memory 1909.

In embodiments, an emergency shut down button may be depressed 1951 to quickly and/or immediately shut down an umbrella shading system. In embodiments, motion control circuitry or module 1920 (e.g., a motion control PCB) may receive 1952 an emergency shut down signal or message communicated via an emergency shut down button. In embodiments, motion control circuitry or module 1920 may communicate 1953 instructions to a rechargeable battery and/or solar power charging assembly to turn off power to components, assemblies, circuitry and parts of a modular umbrella shading system. In embodiments, on next power activation of a modular shading umbrella system, motion control circuitry or module 1920 may communicate instructions, commands, messages and/or signals to an elevation motor assembly to a specified motor position and/or communicate instructions, commands, messages and/or signals to an expansion to close arm support assemblies (and arms) and to begin initiation of a sun tracking sequence (as described above with respect to FIGS. 3 and/or 4 of the present application.

In embodiments, a power button may communicate and/or transmit 1955 a signal to motion control circuitry or module 1920 to initiate a power on sequence of a modular umbrella shading system. In embodiments, motion control circuitry and/or module 1920 may initiate 1956 a default and/or beginning sun tracking sequence. In embodiments, a sun tracking sequence may operate according to a method or process describe in FIGS. 3 and 4.

In embodiments, motion control circuitry or module 1920 may receive 1961 automatic shut-down conditions from one or more assemblies and/or sensors. In embodiments, for example, motion control circuitry or module 1920 may receive a high wind sensor measurement from a wind sensor and/or sensor module. In embodiments, for example, motion control circuitry may receive a high and/or extreme temperature measurement from a temperature sensor and/or sensor module. In embodiments, for example, motion control circuitry 1920 may receive an unacceptable air quality measurement from an air quality sensor and/or sensor module. In embodiments, for example, motion control circuitry may receive a lower than threshold power reading from a rechargeable battery 1934 and/or solar power charging assembly 1935. In embodiments, motion control circuitry or module 1920 may retrieve 1962 automatic shut-down conditions from a memory of motion control circuitry (or another memory of a modular shading system). In embodiments, these instructions and/or position measurements may be for an elevation motor, an azimuth motor and/or an expansion motor. In embodiments, these instructions may be to communicate with a rechargeable battery 1934 and/or a solar power charging assembly 1935. In embodiments, motion control circuitry (or module) 1920 may communicate 1963 instructions, commands, signals and/or messages to an elevation motor assembly to cause a modular umbrella shading system to move to a specified safe position (e.g., such as a 90 degree elevation). In embodiments, motion control circuitry (or module) 1920 may communicate 1964 instructions, commands, signals and/or messages to an expansion motor assembly to move arm support assemblies (and arms) to a specified position (e.g., a closed position) that is safe in extreme weather and/or power situations. In embodiments, motion control circuitry (or module 1920) may communicate 1965 instructions, commands, signals, and/or messages to a rechargeable battery 1934 and/or a solar power charging assembly 1935 to turn off power (and/or shut down power) to assemblies, components and/or devices of a modular umbrella shading system. In embodiments, motion control circuitry (or module 1920) may communicate instructions, commands, signals and/or messages to an azimuth motor assembly to move to a safe position although this may be optional. This is an improvement over existing umbrella systems which are not able to move a modular umbrella shading system to a safe elevation motor setting and to close arms utilizing an expansion motor assembly when dangerous and/or threatening conditions are occurring.

Figure 20A:
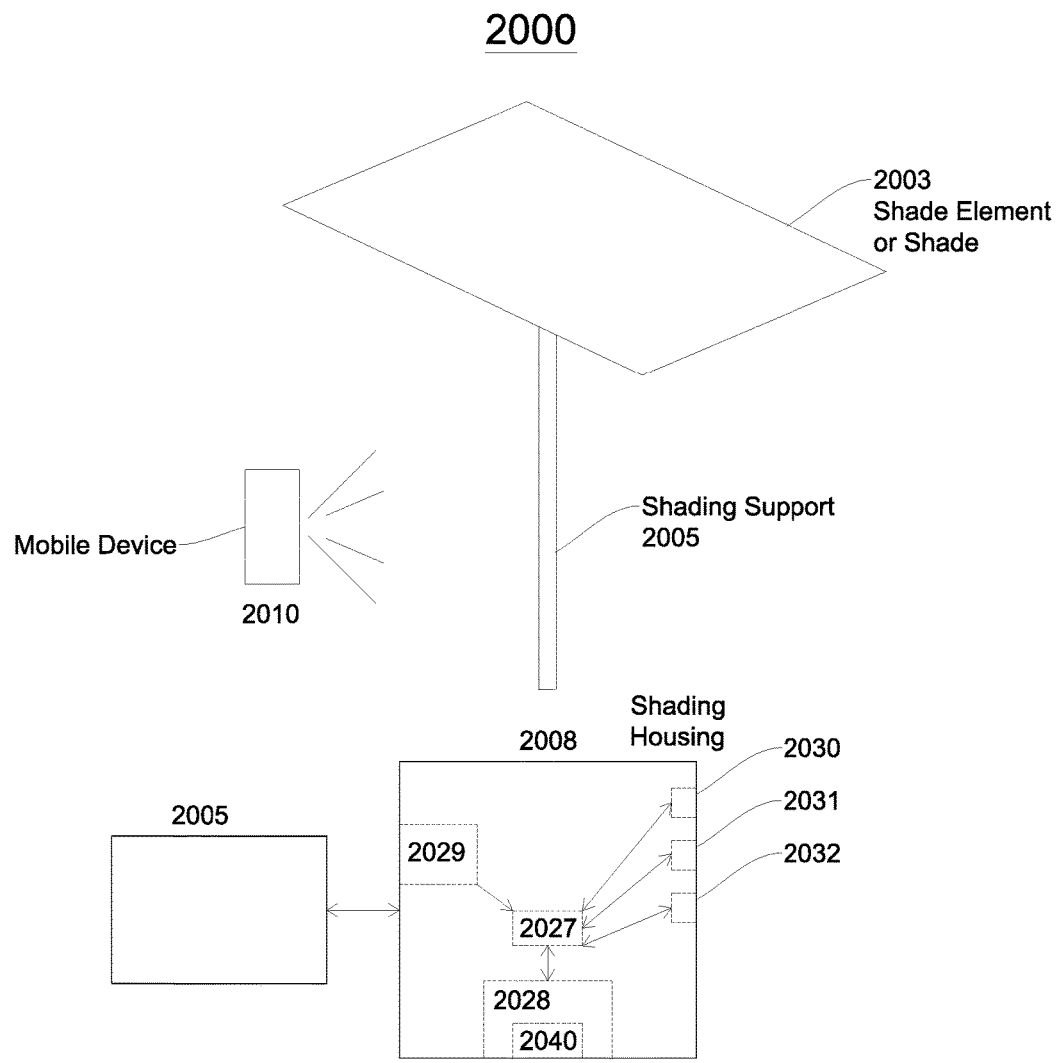
FIG. 20A illustrates a shading system including an artificial intelligence engine and/or artificial intelligence interface.

FIG. 20A illustrates a shading system including an artificial intelligence engine and/or artificial intelligence interface. A shading system including artificial intelligence (AI) 2000 include a shading element or shade 2003, a shading support 2005 and a shading device housing 2008. In embodiments, a shading element or shade 2003 may provide shade to keep a shading device housing 2008 from overheating. In embodiments, a shading device housing 2008 may be coupled and/or connected to a shading support 2005. In embodiments, a shading support 2005 may be coupled to a shading device housing 2008. In embodiments, a shading support 2005 may support a shade or shading element 2003 and move it into position with respect to a shading device housing 2008. In this illustrative embodiment of FIG. 20, a shading device housing 2008 may be utilized as a base, mount and/or support for a shading element or shade 2003. In embodiments, a shading support may be simplified and may not have a tilting assembly (as in FIGS. 1 and 2 where an upper housing of a core module assembly is rotated about (or moved about) a lower housing of a core module assembly). In embodiments, a shading support may be simplified and not have a core assembly. In embodiments, a shading support 2005 may also not include an expansion and sensor assembly. Illustratively, in embodiments, a shading support 2005 may not comprise an integrated computing device and/or may not have sensors. In embodiments, a shading element or shade 2003 or a shade support 2005 may comprise one or more sensors (e.g., environmental sensors). For example, in embodiments, sensors may be a temperature sensor, a wind sensor, a humidity sensor, an air quality sensor, and/or an ultraviolet radiation sensor. In embodiments, a shading support may not include an audio system (e.g., a speaker and/or an audio/video transceiver) and may not include lighting assemblies. In embodiments, a shading housing 2008 may not include one or more lighting assemblies.

In embodiments, a shading device housing 2008 may comprise a computing device 2020. In embodiments, a shading device housing 2008 may comprise one or more processors/controllers 2027, one or more memory modules 2028, one or more microphones (or audio receiving devices) 2029, one or more PAN transceivers 2030 (e.g., Bluetooth transceivers), one or more wireless transceivers 2031 (e.g., WiFi or other 802.11 transceivers), and/or one or more cellular transceivers 2032 (e.g., EDGE transceiver, 4G, 3G, CDMA and/or GSM transceivers). In embodiments, the processors, memory, transceivers and/or microphones may be integrated into a computing device 2020, where in other embodiments, a single-board computing device may not be utilized. In embodiments, one or more memory modules 2028 may contain computer-readable instructions, the computer-readable instructions being executed by one or more processors/controllers 2027 to perform certain functionality. In embodiments, the computer-readable instructions may comprise an artificial intelligence API 2040. In embodiments, an artificial intelligence API 2040 may allow communications between a shading device housing 2008 and a third party artificial intelligence engine housed in a local and/or remote server and/or computing device 2050. In embodiments, an AI API 2040 may be a voice recognition AI API, which may be able to communicate sound files (e.g., analog or digital sound files) to a third party voice recognition AI server. In embodiments, a voice recognition AI server may be an Amazon Alexa, Echo, Echo Dot and/or a Google Now server. In embodiments, a shading device housing 2008 may comprise one or more microphones 2029 to capture audio (and specifically) audible and/or voice commands spoken by users and/or operators of shading systems 2000. In embodiments, computer-readable instructions executed by one or more processors 2027 may receive captured sounds and create analog and/or digital audio files corresponding to spoken audio commands (e.g., open shading system, rotate shading system, elevate shading system, select music to play on shading system, turn one lighting assemblies). In embodiments, an AI API 2040 may communicate audio files to an external AI server 2050. In embodiments, a shading device housing 2008 may communicate generated audio files to external AI servers 2050 via or utilizing one or more PAN transceivers 2030, one or more wireless local area network transceivers 2031, and/or one or more cellular transceivers 2032. In other words, communications with an external AI server 2050 may occur utilizing PAN transceivers 2030 (and protocols). Alternatively, communications with an external AI server 2050 may occur utilizing a local area network (802.11 or WiFi) transceiver 2031. Alternatively, or in combination with, communications with an external AI server 2050 may occur utilizing a cellular transceiver 2032 (e.g., utilizing 3G and/or 4G or other cellular communication protocols). In embodiments, a shading device housing 2008 may utilize more than one microphone 2029 to allow capture of voice commands from a number of locations and/or orientations with respect to a shading system 2000 (e.g., in front of, behind a shading system, and/or at a 45 degree angle with respect to a support assembly 2005).

Figure 20B:
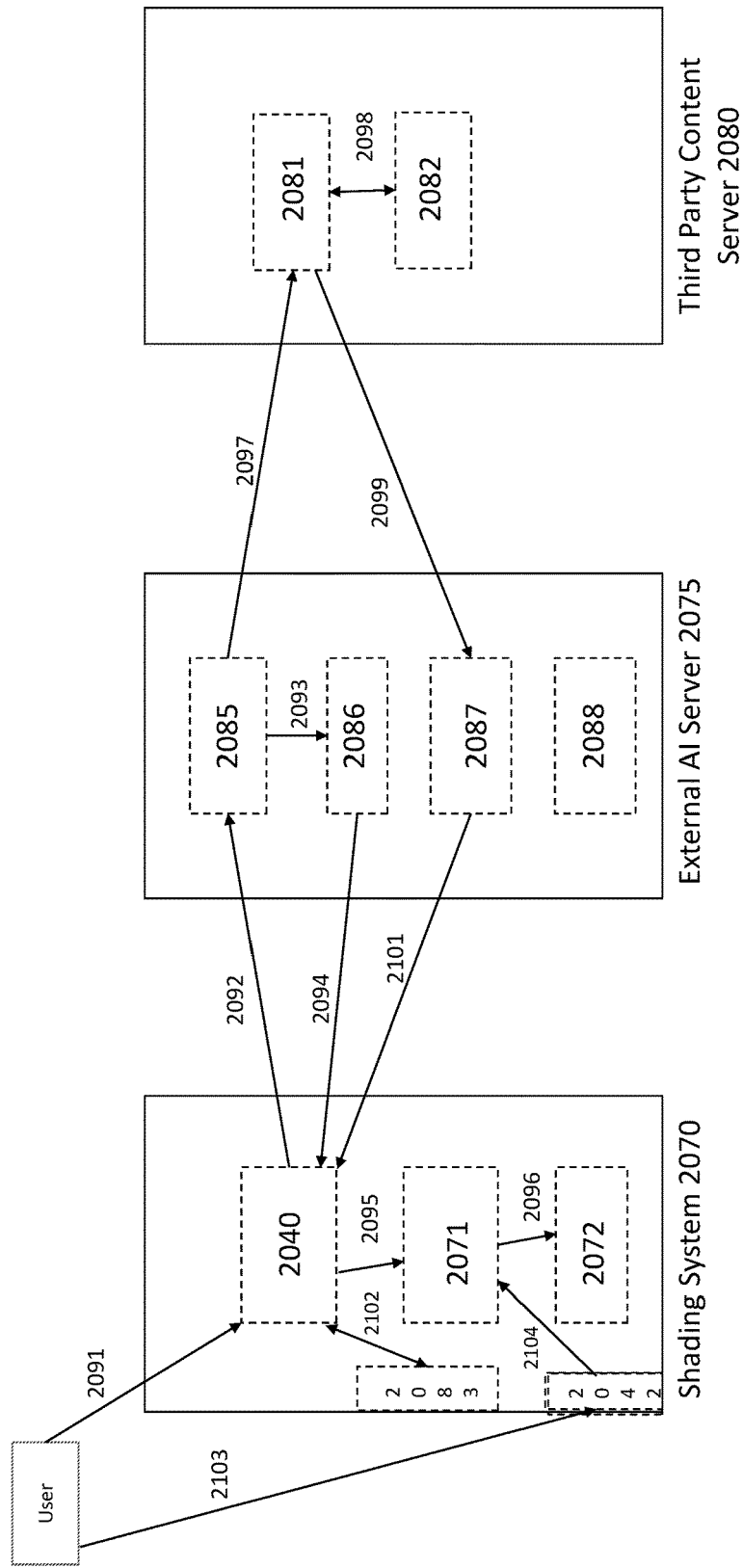
FIG. 20B illustrates a block and dataflow diagram of communications between a shading system and/or one or more external AI servers according to embodiments.

FIG. 20B illustrates a block and dataflow diagram of communications between a shading system and/or one or more external AI servers according to embodiments. A shading system 2070 may communicate with an external AI server 2075 and/or additional content servers 2080 via wireless and/or wired communications networks. In embodiments, a user may speak 2091 a command (e.g., turn on lights, or rotate shading system) which is captured as an audio file and received. In embodiments, an AI API 2040 may communicate and/or transfer 2092 an audio file (utilizing a transceiver—PAN, WiFi/802.11, or cellular) to an external or third-party AI server 2075. In embodiments, an external AI server 2075 may comprise a voice recognition engine or module 2085, a command engine module 2086, a third party content interface 2087 and/or third party content formatter 2088. In embodiments, an external AI server 2075 may receive 2092 one or more audio files and a voice recognition engine or module 2085 may convert received audio file to a device command (e.g., shading system commands, computing device commands) and communicate 2093 device commands to a command engine module or engine 2086. In embodiments, if a voice command is for operation of a shading system 2000, a command engine or module 2086 may communicate and/or transfer 2094 a generated command, message, and/or instruction to a shading system 2000. In embodiments, a shading system 2000 may receive the communicated command, communicate and/or transfer 2095 the communicated command to a controller/processor 2071. In embodiments, the controller/processor 2071 may generate 2096 a command, message, signal and/or instruction to cause an assembly, component, system or devices 2072 to perform an action requested in the original voice command (open or close shade element, turn on camera, activate solar panels).

In embodiments, a user may request actions to be performed utilizing a shading system's microphones and/or transceivers that may require interfacing with third party content servers (e.g., NEST, e-commerce site selling sun care products, e-commerce site selling parts of umbrellas or shading systems, communicating with online digital music stores (e.g., iTunes), home security servers, weather servers and/or traffic servers). For example, in embodiments, a shading system user may request 1) traffic conditions from a third party traffic server; 2) playing of a playlist from a user's digital music store accounts; 3) ordering a replacement skin and/or spokes/blades arms for a shading system. In these embodiments, additional elements and steps may be added to previously described method and/or process.

For example, in embodiments, a user may speak 2091 a command or desired action (execute playlist, order replacement spokes/blades, and/or obtain traffic conditions from a traffic server) which is captured as an audio file and received at an AI API 2040 stored in one or more memories of a shading system housing 2070. As discussed above, in embodiments, an AI API 2040 may communicate and/or transfer 2092 an audio file utilizing a shading system's transceiver to an external AI server 2075. In embodiments, an external AI server 2075 may receive one or more audio files and a voice recognition engine or module 2085 may convert 2093 received audio file to a query request (e.g., traffic condition request, e-commerce order, retrieve and stream digital music playlist).

In embodiments, an external AI server may communicate and/or transfer 2097 a query request to a third party server (e.g., traffic conditions server (e.g., SIGALERT or Maze), an e-commerce server (e.g., a RITE-AID or SHADECRAFT SERVER, or Apple iTunes SERVER) to obtain third party goods and/or services. In embodiments, a third party content server 2080 (a communication and query engine or module 2081) may retrieve 2098 services from a database 2082. In embodiments, a third party content server 2080 may communicate services queried by the user (e.g., traffic conditions or digital music files to be streamed) 2099 to an external AI server 2075. In embodiments, a third party content server 2080 may order requested goods for a user and then retrieve and communicate 2099 a transaction status to an external AI server 2075. In embodiments, a content communication module 2087 may receive communicated services (e.g., traffic conditions or streamed digital music files) or transaction status updates (e.g., e-commerce receipts) and may communicate 2101 the requested services (e.g., traffic conditions or streamed digital music files) or the transaction status updates to a shading system 2070. Traffic services may be converted to an audio signal, and an audio signal may be reproduced utilizing an audio system 2083. Digital music files may be communicated and/or streamed directed to an audio system 2083 because there is no conversion necessary. E-commerce receipts may be converted and communicated to speaker 2083 for reading aloud. E-commerce receipts may also be transferred to computing device in a shading system 2070 for storage and utilization later.

In embodiments, computer-readable instructions in a memory module of a shading system may be executed by a processor and may comprise a voice recognition module or engine 2042 and in this embodiment, voice recognition may be performed at an intelligent shading system 2000 without utilizing a cloud-based server. In embodiments, a shading system 2070 may receive 2103 the communicated command, communicate and/or transfer 2104 the communicated command to a controller/processor 2071. In embodiments, the controller/processor 2071 may generate and/or communicate 2096 a command, message, signal and/or instruction to cause an assembly, component, system or device 2072 to perform an action requested in the original voice command Referring back to FIG. 20A, in embodiments, a mobile computing device 2010 may communicate with a shading system with an artificial intelligence capabilities. In embodiments, a user may communicate with a mobile computing or communications device 2010 by a spoken command into a microphone. In embodiments, a mobile computing or communications device 2010 communicates a digital or analog audio file to a processor 2027 and/or AI API 2040 in a shading device housing. In embodiments, a mobile computing or communications device 2010 may also convert the audio file into a textual file for easier conversion from an external or integrated AI server or computing device 2050.

FIGS. 20A and 20B describe a shading system having a shading element or shade, shading support and/or shading housing. A shading housing such as the one described above may be attached to any shading system and may provide artificial intelligence functionality and services. In embodiments, a shading system may be an autonomous and/or automated shading system having an integrated computing device, sensors and other components and/or assemblies, and may have artificial intelligence functionality and services provided utilizing an AI API stored in a memory of a shading housing.

Figure 21:
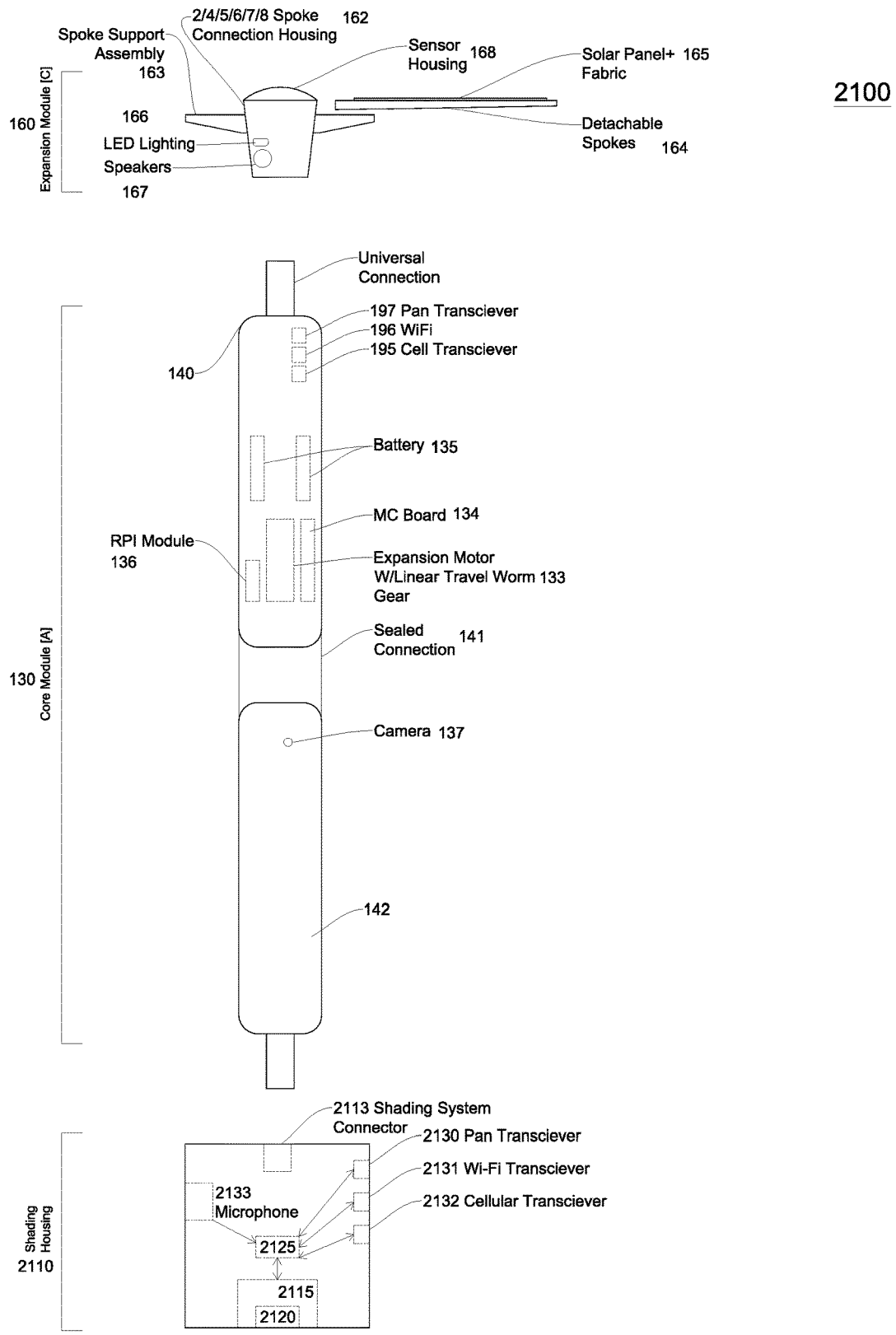
FIG. 21 illustrates an intelligence shading system comprising a shading housing wherein a shading housing comprises an AI API.

FIG. 21 illustrates an intelligent shading system comprising a shading housing wherein a shading housing comprises an AI API. In embodiments, a shading system 2100 comprises an expansion module 160, a core module 130 and a shading housing 2110. In embodiments, an expansion module 160 may comprise one or more spoke support assemblies 163, one or more detachable arms/spokes 164, one or more solar panels and/or fabric 165, one or more LED lighting assemblies 166 and/or one or more speakers 167. In embodiments, an expansion module 160 may be coupled and/or connected to a core assembly module 130. In embodiments, a coupling and/or connection may be made via a universal connection. In embodiments, a core module assembly 130 may comprise an upper assembly 140, a sealed connection 141 and/or a lower assembly 142. In embodiments, a core module assembly 130 may comprise one or more rechargeable batteries 135, a motion control board 134, an expansion motor 133 and/or an integrated computing device 136. In embodiments, a core module assembly 130 may comprise one or more transceivers (e.g., a PAN transceiver 197, a WiFi transceiver 196 and/or a cellular transceiver). In embodiments, a core module assembly 130 may be coupled and/or connected to a shading housing 2110. In embodiments, a universal connector may be a connector and/or coupler between a core module assembly 130 and a shading housing 2110.

In embodiments, a shading housing 2110 may comprise a shading system connector 2113, one or more memory modules 2115, one or more processors/controllers 2125, one or more microphones 2133, one or more transceivers (e.g., a PAN transceiver 2130, a wireless local area network (e.g., WiFi) transceiver 2131, and/or a cellular transceiver 2132), and an artificial intelligence ("AI") Application programming interface ("API") 2120. In embodiments, one or more microphones 2133 receives a spoken command and captures/converts the command into a digital and/or analog audio file. In embodiments, one or more processors/controllers 2125 interacts and executes AI API 2120 instructions (stored in one or more memory modules 2115) and communicates and/or transfers audio files to a third party AI server (e.g., an external AI server or computing device). In embodiments, an AI API 2120 may communicate and/or transfer audio files via and/or utilizing a PAN transceiver 2130, a local area network (e.g., WiFi) transceiver 2131, and/or a cellular transceiver 2132. In embodiment, an AI API may receive communications, data, measurements, commands, instructions and/or files from an external AI server or computing device (as described in FIGS. 21 and 22) and perform and/or execute actions in responses to these communications.

In embodiments, a shading system and/or umbrella may communicate via one or more transceivers. This provides a shading system with an ability to communicate with external computing devices, servers and/or mobile communications device in almost any situation. In embodiments, a shading system with a plurality of transceivers (e.g., a PAN transceiver, a local area network (e.g., WiFi) transceiver, and/or a cellular transceiver) may communicate when one or more communication networks are down, experiencing technical difficulties, inoperable and/or not available. For example, a WiFi wireless router may be malfunctioning and a shading system with a plurality of transceivers may be able to communicate with external devices via a PAN transceiver and/or a cellular transceiver. In addition, an area may be experiencing heavy rains or weather conditions and cellular communications may be down and/or not available (and thus cellular transceivers may be inoperable). In these situations, a shading system with one or more transceivers may communicate with external computing devices via the operating transceivers. Since most shading systems may not have any communication transceivers, the shading systems described herein is an improvement over existing shading systems that have no communication capabilities and/or limited communication capabilities.

In embodiments, a base assembly or module may also a base motor controller PCB, a base motor, a drive assembly and/or wheels. In embodiments, a base assembly may move to track movement of the sun, wind conditions, and/or an individual's commands. In embodiments, a shading object movement control PCB may send commands, instructions, and/or signals to a base assembly identifying desired movements of a base assembly. In embodiments, a shading computing device system (including a SMARTSHADE and/or SHADECRAFT application) or a desktop computer application may transmit commands, instructions, and/or signals to a base assembly identifying desired movements of a base assembly. In embodiments, a base motor controller PCB may receive commands, instructions, and/or signals and may communicate commands and/or signals to a base motor. In embodiments, a base motor may receive commands and/or signals, which may result in rotation of a motor shaft. In embodiments, a motor shaft may be connected, coupled, or indirectly coupled (through gearing assemblies or other similar assemblies) to one or more drive assemblies. In embodiments, a drive assembly may be one or more axles, where one or more axles may be connected to wheels. In embodiments, for example, a base assembly may receive commands, instructions and/or signal to rotate in a counterclockwise direction approximately 15 degrees. In embodiments, for example, a motor output shaft would rotate one or more drive assemblies rotate a base assembly approximately 15 degrees. In embodiments, a base assembly may comprise more than one motor and/or more than one drive assembly. In this illustrative embodiment, each of motors may be controlled independently from one another and may result in a wider range or movements and more complex movements.

In embodiments, a base assembly 110 and/or first extension assembly 120 may be comprised of stainless steel. In embodiments, a base assembly 110 and/or first extension assembly 120 may be comprised of a plastic and/or a composite material, or a combination of materials listed above. In embodiments, a base assembly 110 and/or first extension assembly 120 may be comprised and/or constructed by a biodegradable material. In embodiments, a base assembly 110 and/or first extension assembly 120 may be tubular with a hollow inside except for shelves, ledges, and/or supporting assemblies. In embodiments, a base assembly 110 and/or first extension assembly 120 may have a coated inside surface. In embodiments, a base assembly 110 and/or first extension assembly 120 may have a circular circumference or a square circumference.

In embodiments, a core module assembly 130 may be comprised of stainless steel. In embodiments, a core module assembly 130 may be comprised of a metal, plastic and/or a composite material, or a combination thereof. In embodiments, a core module assembly 130 may be comprised of wood, steel, aluminum or fiberglass. In embodiments, a shading object center support assembly may be a tubular structure, e.g., may have a circular or an oval circumference. In embodiments, a core module assembly 130 may be a rectangular or triangular structure with a hollow interior. In embodiments, a hollow interior of a core module assembly 130 may have a shelf or other structures for holding or attaching assemblies, PCBs, and/or electrical and/or mechanical components. In embodiments, for example components, PCBs, and/or motors may be attached or connected to an interior wall of a shading object center assembly.

In embodiments, a plurality of spokes/arms/blades 164 and/or spoke/arm support assemblies 163 may be composed of materials such as plastics, plastic composites, fabric, metals, woods, composites, or any combination thereof. In an example embodiment, spokes/arms/blades 164 and/or spoke/arm support assemblies 163 may be made of a flexible material. In an alternative example embodiment, spokes/arms/blades 164 and/or spokes/arm support assemblies 163 may be made of a stiffer material.

Some discussions may be focused on single shading objects, intelligent umbrellas, and/or intelligent shading charging systems. However, descriptions included herein may be applicable to multiple shading objects, intelligent umbrellas and/or intelligent shading charging systems. In addition, while discussions may be directed to a software application or process executing on a computing device of a shading object, intelligent umbrella and/or intelligent shading charging system and controlling one shading object, intelligent umbrella and/or intelligent shading charging system, the descriptions also apply to controlling and/or communicating with multiple shading objects, intelligent umbrellas and/or intelligent charging systems.

A computing device may be a server, a computer, a laptop computer, a mobile computing device, a mobile communications device, and/or a tablet. A computing device may, for example, include a desktop computer or a portable device, such as a cellular telephone, a smart phone, a display pager, a radio frequency (RF) device, an infrared (IR) device, a Personal Digital Assistant (PDA), a handheld computer, a tablet computer, a laptop computer, a set top box, a wearable computer, an integrated device combining various features, such as features of the forgoing devices, or the like.

Internal architecture of a computing device includes one or more processors (also referred to herein as CPUs), which interface with at least one computer bus. Also interfacing with computer bus are persistent storage medium/media, network interface, memory, e.g., random access memory (RAM), run-time transient memory, read only memory (ROM), etc., media disk drive interface, an interface for a drive that can read and/or write to media including removable media such as floppy, CD-ROM, DVD, etc., media, display interface as interface for a monitor or other display device, keyboard interface as interface for a keyboard, mouse, trackball and/or pointing device, and other interfaces not shown individually, such as parallel and serial port interfaces, a universal serial bus (USB) interface, and the like.

Memory, in a computing device and/or a modular umbrella shading system, interfaces with computer bus so as to provide information stored in memory to processor during execution of software programs such as an operating system, application programs, device drivers, and software modules that comprise program code or logic, and/or computer-executable process steps, incorporating functionality described herein, e.g., one or more of process flows described herein. CPU first loads computer-executable process steps or logic from storage, storage medium/media, removable media drive, and/or other storage device. CPU can then execute the stored process steps in order to execute the loaded computer-executable process steps. Stored data, e.g., data stored by a storage device, can be accessed by CPU during the execution of computer-executable process steps.

Non-volatile storage medium/media is a computer readable storage medium(s) that can be used to store software and data, e.g., an operating system and one or more application programs, in a computing device or storage subsystem of an intelligent shading object. Persistent storage medium/media also be used to store device drivers, such as one or more of a digital camera driver, monitor driver, printer driver, scanner driver, or other device drivers, web pages, content files, metadata, playlists and other files. Non-volatile storage medium/media can further include program modules/program logic in accordance with embodiments described herein and data files used to implement one or more embodiments of the present disclosure.

A computing device or a processor or controller may include or may execute a variety of operating systems, including a personal computer operating system, such as a Windows, iOS or Linux, or a mobile operating system, such as iOS, Android, or Windows Mobile, Windows Phone, Google Phone, Amazon Phone, or the like. A computing device, or a processor or controller in an intelligent shading controller may include or may execute a variety of possible applications, such as a software applications enabling communication with other devices, such as communicating one or more messages such as via email, short message service (SMS), or multimedia message service (MMS), including via a network, such as a social network, including, for example, Facebook, LinkedIn, Twitter, Flickr, or Google+, to provide only a few possible examples. A computing device or a processor or controller in an intelligent shading object may also include or execute an application to communicate content, such as, for example, textual content, multimedia content, or the like. A computing device or a processor or controller in an intelligent shading object may also include or execute an application to perform a variety of possible tasks, such as browsing, searching, playing various forms of content, including locally stored or streamed content. The foregoing is provided to illustrate that claimed subject matter is intended to include a wide range of possible features or capabilities. A computing device or a processor or controller in an intelligent shading object may also include imaging software applications for capturing, processing, modifying and transmitting image files utilizing the optical device (e.g., camera, scanner, optical reader) within a mobile computing device.

Network link typically provides information communication using transmission media through one or more networks to other devices that use or process the information. For example, network link may provide a connection through a network (LAN, WAN, Internet, packet-based or circuit-switched network) to a server, which may be operated by a third party housing and/or hosting service. For example, the server may be the server described in detail above. The server hosts a process that provides services in response to information received over the network, for example, like application, database or storage services. It is contemplated that the components of system can be deployed in various configurations within other computer systems, e.g., host and server.

For the purposes of this disclosure a computer readable medium stores computer data, which data can include computer program code that is executable by a computer, in machine-readable form. By way of example, and not limitation, a computer-readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

For the purposes of this disclosure a system or module is a software, hardware, or firmware (or combinations thereof), process or functionality, or component thereof, that performs or facilitates the processes, features, and/or functions described herein (with or without human interaction or augmentation). A module can include sub-modules. Software components of a module may be stored on a computer readable medium. Modules may be integral to one or more servers, or be loaded and executed by one or more servers. One or more modules may be grouped into an engine or an application.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client or server or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all implementations falling within the scope of the appended claims, and equivalents thereof.

The invention claimed is:
1. An intelligent umbrella system, comprising:
one or more shading elements;
a support assembly, coupled to the one or more shading elements, to provide support for the one or more shading elements;
a base assembly, coupled to the support assembly, to provide contact with a surface;
one or more microphones to capture spoken or audio commands;
one or more processors;
one or more memory modules;
one or more wireless communication transceivers;

wherein computer-readable instructions stored in the one or more memory modules are executable by the one or more processors to:
convert the captured audio commands into audio files; and
perform voice recognition on the converted audio files to generate instructions or commands based, at least in part, on the converted audio files; and
one or more environmental sensors, wherein the audio command requests sensor measurements from the one or more environmental sensors, and the computer-readable instructions are executable by the one or more processors to generate and communicate the instructions or commands to the one or more environmental sensors to capture sensor measurements and receive the captured sensor measurements from the one or more environmental sensors.

2. The intelligent umbrella system of claim 1, wherein the base assembly comprises the one or more processors, the one or more memory modules, and the computer-readable instructions.

3. The intelligent umbrella system of claim 1, further comprising an audio receiver and a speaker, wherein the computer-readable instructions are executable by the one or more processors to retrieve digital music files and to communicate the retrieved digital musical files to the audio receiver and speaker for playback.

4. The modular umbrella system of claim 1, further comprising one or more motor assemblies to move the support assembly or the shading element, wherein the audio command requests movement of the one or more motor assemblies, and wherein the computer-readable instructions are executable by the one or more processors to generate and communicate the instructions or commands to the one or more motor assemblies to move the support assembly or the shading element to adjust a position or orientation of the support assembly or shading element.

5. The modular umbrella system of claim 1, further comprising one or more motor assemblies to move the support assembly or the shading element, wherein the audio command requests initiation of a sun tracking routine, and wherein the computer-readable instructions are executable by the one or more processors to generate and communicate the instructions or commands to the one or more motor assemblies to move the support assembly or the shading element to adjust a position or orientation of the support assembly or shading element.

6. The intelligent umbrella system of claim 1, further comprising one or more imaging devices, wherein the audio command requests activation of the one or more imaging devices, and computer-readable instructions are executable by the one or more processors to generate and communicate the instructions or commands to the one or more imaging devices to capture images or video of an area surrounding the intelligent umbrella system, to receive the images or video from the one or more imaging devices and to store the images or video in the one or more memory devices.

7. The intelligent umbrella system of claim 1, further comprising one or more lighting assemblies, wherein the audio command requests the one or more lighting assemblies to be activated, and wherein the computer-readable instructions are executable by the one or more processors to generate and communicate the instructions or commands to the one or more lighting assemblies to activate the one or more lighting assemblies.

8. An intelligent umbrella system, comprising:
one or more shading elements;
a support assembly, coupled to the one or more shading elements, to provide support for the one or more shading elements;
a base assembly, coupled to the support assembly, to provide contact with a surface;
one or more microphones to capture spoken or audio commands;
one or more processors;
one or more memory modules;
one or more wireless communication transceivers;
wherein computer-readable instructions stored in the one or more memory modules are executed by the one or more processors to:
convert the captured audio commands into audio files; and
perform voice recognition on the converted audio files to generate instructions or commands based, at least in part, on the converted audio files; and
an audio transceiver and a speaker, wherein the audio command requests an alarm be generated, and wherein the computer-readable instructions are executable by the one or more processors to generate and communicate the instructions or commands to the audio transceiver to play an alarm file, where the audio transceiver converts the alarm file to an alarm sound which is reproduced by the speaker.

9. The intelligent umbrella of claim 8, wherein the computer-readable instructions are further executable by the one or more processors to retrieve digital music files and to communicate the retrieved digital musical files to the audio transceiver and speaker for playback.

10. The intelligent umbrella of claim 8, wherein the base assembly comprises the one or more processors, the one or more memory modules, and the computer-readable instructions.

11. The intelligent umbrella of claim 8, further comprising one or more environmental sensors, wherein the audio command requests sensor measurements from the one or more environmental sensors, and the computer-readable instructions are executable by the one or more processors to generate and communicate the instructions or commands to the one or more environmental sensors to capture sensor measurements and receive the captured sensor measurements from the one or more environmental sensors.

12. The intelligent umbrella of claim 8, further comprising one or more motor assemblies to move the support assembly or the shading element, wherein the audio command requests movement of the one or more motor assemblies, and wherein the computer-readable instructions are executable by the one or more processors to generate and communicate the instructions or commands to the one or more motor assemblies to move the support assembly or the shading element to adjust a position or orientation of the support assembly or shading element.

13. The intelligent umbrella of claim 8, further comprising one or more motor assemblies to move the support assembly or the shading element, wherein the audio command requests initiation of a sun tracking routine, and wherein the computer-readable instructions are executable by the one or more processors to generate and communicate the instructions or commands to the one or more motor assemblies to move the support assembly or the shading element to adjust a position or orientation of the support assembly or shading element.

14. The intelligent umbrella of claim 8, further comprising one or more imaging devices, wherein the audio command requests activation of the one or more imaging devices, and computer-readable instructions are executable by the one or more processors to generate and communicate the instructions or commands to the one or more imaging devices to capture images or video of an area surrounding the intelligent umbrella system, to receive the images or video from the one or more imaging devices and to store the images or video in the one or more memory devices.

15. The intelligent umbrella of claim 8, further comprising one or more lighting assemblies, wherein the audio command requests the one or more lighting assemblies to be activated, and wherein the computer-readable instructions are executable by the one or more processors to generate and communicate the instructions or commands to the one or more lighting assemblies to activate the one or more lighting assemblies.

\* \* \* \* \*